US008795693B2

(12) United States Patent
Tamarkin et al.

(10) Patent No.: US 8,795,693 B2
(45) Date of Patent: Aug. 5, 2014

(54) COMPOSITIONS WITH MODULATING AGENTS

(75) Inventors: Dov Tamarkin, Maccabim (IL); Meir Eini, Ness Ziona (IL); Doron Friedman, Karmei Yosef (IL); Tal Berman, Rishon LeZiyyon (IL); David Schuz, Moshav Gimzu (IL)

(73) Assignee: Foamix Ltd., Rehovot (IL)

( * ) Notice: Subject to any disclaimer, the term of this patent is extended or adjusted under 35 U.S.C. 154(b) by 1051 days.

(21) Appl. No.: 11/947,751

(22) Filed: Nov. 29, 2007

(65) Prior Publication Data

US 2008/0206159 A1 Aug. 28, 2008

Related U.S. Application Data

(63) Continuation-in-part of application No. 10/835,505, filed on Apr. 28, 2004, now Pat. No. 7,820,145, and a continuation-in-part of application No. 11/430,599, filed on May 9, 2006, now Pat. No. 7,704,518.

(60) Provisional application No. 60/492,385, filed on Aug. 4, 2003, provisional application No. 60/530,015, filed on Dec. 16, 2003, provisional application No. 60/679,020, filed on May 9, 2005, provisional application No. 60/784,793, filed on Mar. 21, 2006, provisional application No. 60/861,620, filed on Nov. 29, 2006.

(51) Int. Cl.
*A61K 8/02* (2006.01)
*A61K 9/12* (2006.01)
*A61K 31/56* (2006.01)

(52) U.S. Cl.
CPC ............... *A61K 31/56* (2013.01); *A61K 9/122* (2013.01)
USPC ........................................................ 424/401

(58) Field of Classification Search
None
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brighttenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,867 A | 8/1966 | Lehmann |
| 3,263,869 A | 8/1966 | Corsette |
| 3,298,919 A | 1/1967 | Charles et al. |
| 3,301,444 A | 1/1967 | Wittke |
| 3,303,970 A | 2/1967 | Breslau et al. |
| 3,330,730 A | 7/1967 | Hernaadez |
| 3,333,333 A | 8/1967 | Noack |
| 3,334,147 A | 8/1967 | Brunelle et al. |
| 3,346,451 A | 10/1967 | Collins et al. |
| 3,366,494 A | 1/1968 | Bower |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Warren |
| 3,401,849 A | 9/1968 | Weber, III |
| 3,419,658 A | 12/1968 | Amsdon |
| 3,456,052 A | 7/1969 | Gordon |

(Continued)

FOREIGN PATENT DOCUMENTS

| | | |
|---|---|---|
| AU | 198780257 | 9/1986 |
| AU | 782515 | 12/2005 |

(Continued)

OTHER PUBLICATIONS

Alcohol SDA 40B.http://www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, http://www.arisankimya.com/kozmetik.htm Accessed Dec. 10, 2008, 8 pages.
Barry, B.W. et al, Comparative bio-availability and activity of proprietary topical corticosteroid preparations: vasoconstrictor assays on thirty-one ointments, British Journal of Dermatology, 93, 563-571, 1975.

(Continued)

*Primary Examiner* — Anand Desai
*Assistant Examiner* — Melissa Mercier
(74) *Attorney, Agent, or Firm* — Fish & Richardson P.C.

(57) ABSTRACT

The present invention relates to a waterless composition and foam as a vehicle in which an active pharmaceutical or cosmetic agent, when added is stable or stabilized by or its destabilization is impeded by the presence of a modulating agent. The pharmaceutical or cosmetic composition and foam, includes: a waterless solvent, a modulating agent and one or more active pharmaceutical or cosmetic agents. The present invention also relates to a method of treatment administering the waterless composition and foam.

63 Claims, No Drawings

(56) References Cited

U.S. PATENT DOCUMENTS

| | | | |
|---|---|---|---|
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borocki |
| 3,563,098 A | 2/1971 | Weber, III |
| 3,574,821 A | 4/1971 | Pfirrmann and Geitlich |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackes |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom et al. |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,052,513 A | 10/1977 | Kaplan |
| 4,083,974 A | 4/1978 | Turi |
| 4,100,426 A | 7/1978 | Baranowski et al. |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A * | 1/1984 | Ofuchi et al. .......... 514/174 |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves et al. |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |

(56) References Cited

U.S. PATENT DOCUMENTS

| | | |
|---|---|---|
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs et al. |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |

(56) References Cited

U.S. PATENT DOCUMENTS

| | | | |
|---|---|---|---|
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A * | 7/1999 | Gopalkrishnan et al. ... 514/772.1 |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret et al. |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,261,544 B1 | 7/2001 | Coury et al. |
| 6,270,781 B1 | 8/2001 | Gehlsen |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,532 B1 | 11/2002 | Kamimura et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy et al. |
| 6,682,726 B2 | 1/2004 | Marchesi et al. |

(56) References Cited

U.S. PATENT DOCUMENTS

| | | |
|---|---|---|
| 6,682,750 B2 | 1/2004 | Loeffler et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,946,120 B2 | 9/2005 | Wai-Chiu et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram et al. |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,960,416 B2 | 6/2011 | Sato et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,375 B2 | 7/2013 | Tamarkin et al. |
| 8,518,376 B2 | 8/2013 | Tamarkin et al. |
| 8,618,081 B2 | 12/2013 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1* | 8/2002 | Vishnupad .................... 510/130 |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |

(56) References Cited

U.S. PATENT DOCUMENTS

| | | |
|---|---|---|
| 2005/0031547 A1 | 2/2005 | Tamarkin et al. |
| 2005/0042182 A1 | 2/2005 | Arkin |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0017696 A1 | 1/2007 | Lin et al. |
| 2007/0020213 A1 | 1/2007 | Tamarkin |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0224143 A1 | 9/2007 | Konis |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0053290 A1 | 2/2009 | Sand et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0266510 A1 | 10/2010 | Tamarkin et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0212033 A1 | 9/2011 | Tamarkin et al. |
| 2011/0268665 A1 | 11/2011 | Tamarkin et al. |
| 2012/0064136 A1 | 3/2012 | Baker, Jr. et al. |

(56) References Cited

U.S. PATENT DOCUMENTS

| | | | |
|---|---|---|---|
| 2012/0087872 A1 | 4/2012 | Tamarkin et al. |
| 2012/0128598 A1 | 5/2012 | Trumbore et al. |
| 2012/0148503 A1 | 6/2012 | Tamarkin et al. |
| 2012/0156144 A1 | 6/2012 | Tamarkin et al. |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0295022 A1 | 11/2013 | Friedman et al. |
| 2014/0050673 A1 | 2/2014 | Tamarkin et al. |

FOREIGN PATENT DOCUMENTS

| | | | |
|---|---|---|---|
| AU | 2010219295 | | 9/2012 |
| CA | 2154438 | | 1/1996 |
| CA | 2422244 | | 9/2003 |
| CA | 2502986 | | 8/2011 |
| CA | 2534372 | | 1/2012 |
| CA | 2536482 | | 7/2012 |
| CH | 639913 | | 12/1983 |
| DE | 1 882 100 | | 11/1963 |
| DE | 1926796 | | 11/1965 |
| DE | 4140474 | | 6/1993 |
| DE | 10009233 | | 8/2000 |
| DE | 10138495 | | 2/2003 |
| DE | 102004016710 | | 10/2005 |
| DE | 2 608 226 | | 9/2007 |
| EP | 0 156 507 | | 10/1985 |
| EP | 0156507 | A1 | 10/1985 |
| EP | 0186453 | | 7/1986 |
| EP | 211550 | | 2/1987 |
| EP | 0214865 | A2 | 3/1987 |
| EP | 0 216 856 | | 4/1987 |
| EP | 0270316 | | 6/1988 |
| EP | 297436 | | 1/1989 |
| EP | 0 326 196 | | 8/1989 |
| EP | 0 336 812 | | 10/1989 |
| EP | 0 391 124 | | 10/1990 |
| EP | 0404376 | | 12/1990 |
| EP | 414920 | | 3/1991 |
| EP | 0 485 299 | | 5/1992 |
| EP | 0484530 | A1 | 5/1992 |
| EP | 0488089 | A1 | 6/1992 |
| EP | 0 504 301 | | 9/1992 |
| EP | 0 528 190 | | 2/1993 |
| EP | 0535327 | | 4/1993 |
| EP | 0 552 612 | | 7/1993 |
| EP | 0569773 | A2 | 11/1993 |
| EP | 0598412 | | 11/1993 |
| EP | 0 662 431 | | 7/1995 |
| EP | 0676198 | | 10/1995 |
| EP | 0738516 | | 10/1996 |
| EP | 0 757 959 | | 2/1997 |
| EP | 0824911 | | 2/1998 |
| EP | 0 829 259 | | 3/1998 |
| EP | 0 928 608 | | 7/1999 |
| EP | 0979654 | A1 | 2/2000 |
| EP | 0993827 | A1 | 4/2000 |
| EP | 1 025 836 | | 8/2000 |
| EP | 1055425 | A2 | 11/2000 |
| EP | 0 506 197 | | 7/2001 |
| EP | 1215258 | | 6/2002 |
| EP | 1287813 | | 3/2003 |
| EP | 1 308 169 | | 5/2003 |
| EP | 1 375 386 | | 1/2004 |
| EP | 1428521 | | 6/2004 |
| EP | 1438946 | | 7/2004 |
| EP | 1189579 | | 9/2004 |
| EP | 1475381 | | 11/2004 |
| EP | 1 483 001 | | 12/2004 |
| EP | 1500385 | | 1/2005 |
| EP | 1 537 916 | | 6/2005 |
| EP | 1 600 185 | | 11/2005 |
| EP | 1 734 927 | | 12/2006 |
| EP | 1 758 547 | | 3/2007 |
| EP | 1584324 | | 11/2007 |
| EP | 1 889 609 | | 2/2008 |
| EP | 2422768 | | 2/2012 |
| EP | 2494959 | | 9/2012 |
| FR | 2 591 331 | | 6/1987 |
| FR | 2 640 942 | | 6/1990 |
| FR | 2 736 824 | | 1/1997 |
| FR | 2774595 | A | 8/1999 |
| FR | 2 789 371 | | 8/2000 |
| FR | 2 793 479 | | 11/2000 |
| FR | 2 814 959 | | 4/2002 |
| FR | 2 833 246 | | 6/2003 |
| FR | 2 840 903 | | 12/2003 |
| FR | 2 843 373 | | 2/2004 |
| FR | 2 845 672 | | 4/2004 |
| FR | 2 848 998 | | 6/2004 |
| FR | 2 860 976 | | 4/2005 |
| FR | 2915891 | | 11/2008 |
| GB | 808104 | | 1/1959 |
| GB | 808105 | | 1/1959 |
| GB | 922930 | | 4/1963 |
| GB | 933486 | * | 8/1963 |
| GB | 998 490 | | 7/1965 |
| GB | 1026831 | | 4/1966 |
| GB | 1 033 299 | | 6/1966 |
| GB | 1 081 949 | | 9/1967 |
| GB | 1121358 | | 7/1968 |
| GB | 1 162 684 | | 8/1969 |
| GB | 1 170 152 | | 11/1969 |
| GB | 1 201 918 | | 8/1970 |
| GB | 1 347 950 | | 2/1974 |
| GB | 1 351 761 | | 5/1974 |
| GB | 1 351 762 | | 5/1974 |
| GB | 1 353 381 | | 5/1974 |
| GB | 1 376 649 | | 12/1974 |
| GB | 1397285 | | 6/1975 |
| GB | 1 408 036 | | 10/1975 |
| GB | 1 457 671 | | 12/1976 |
| GB | 1 489 672 | | 10/1977 |
| GB | 2 004 746 | | 4/1979 |
| GB | 1 561 423 | | 2/1980 |
| GB | 2114580 | | 8/1983 |
| GB | 2 153 686 | | 8/1985 |
| GB | 2 172 298 | | 9/1986 |
| GB | 2 206 099 | | 12/1988 |
| GB | 2166651 | | 5/1996 |
| GB | 2337461 | | 11/1999 |
| GB | 2 367 809 | | 4/2002 |
| GB | 2 406 330 | | 3/2005 |
| GB | 2 406 791 | | 4/2005 |
| GB | 2 474 930 | | 7/2012 |
| IL | 49491 | | 9/1979 |
| IL | 0152486 | | 5/2003 |
| JP | 60001113 | | 4/1978 |
| JP | 55069682 | | 5/1980 |
| JP | 57044429 | | 3/1982 |
| JP | 56039815 | | 4/1984 |
| JP | 61275395 | | 12/1986 |
| JP | 62241701 | | 10/1987 |
| JP | 63119420 | | 5/1988 |
| JP | 01100111 | | 4/1989 |
| JP | 01156906 | | 6/1989 |
| JP | 2184614 | | 7/1990 |
| JP | 2255890 | | 10/1990 |

(56) References Cited

FOREIGN PATENT DOCUMENTS

| | | |
|---|---|---|
| JP | 04282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 8501529 | 2/1996 |
| JP | 2008040899 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000/017174 | 1/2000 |
| JP | 2000080017 | 3/2000 |
| JP | 2000128734 | 5/2000 |
| JP | 2000191429 | 7/2000 |
| JP | 2000/239140 | 9/2000 |
| JP | 2000/354623 | 12/2000 |
| JP | 2000351726 | 12/2000 |
| JP | 2001/002526 | 1/2001 |
| JP | 2001019606 | 1/2001 |
| JP | 2001072963 | 3/2001 |
| JP | 2002012513 | 1/2002 |
| JP | 2002047136 | 2/2002 |
| JP | 2002/524490 | 8/2002 |
| JP | 2002/302419 | 10/2002 |
| JP | 2003/012511 | 1/2003 |
| JP | 2003055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005350378 | 12/2005 |
| JP | 2006008574 | 1/2006 |
| JP | 2006/036317 | 2/2006 |
| JP | 2006/103799 | 4/2006 |
| JP | 2006525145 | 11/2006 |
| JP | 2007131539 | 5/2007 |
| JP | 2007326996 | 12/2007 |
| JP | 4892282 | 3/2012 |
| KR | 143232 | 7/1998 |
| KR | 2001/003063 | 1/2001 |
| NZ | 520014 | 5/2005 |
| NZ | 540166 | 6/2007 |
| RU | 2277501 | 6/2006 |
| UA | 66796 | 6/2004 |
| WO | 82/01821 | 6/1982 |
| WO | WO-86/05389 | 9/1986 |
| WO | 88/01502 | 3/1988 |
| WO | WO-88/01863 | 3/1988 |
| WO | 88/08316 | 11/1988 |
| WO | WO-89/06537 | 7/1989 |
| WO | WO-90/05774 | 5/1990 |
| WO | WO91/11991 | * 8/1991 |
| WO | WO9111991 | * 8/1991 |
| WO | WO-92/00077 | 1/1992 |
| WO | 92/05142 | 4/1992 |
| WO | 92/05763 | 4/1992 |
| WO | WO-92/11839 | 7/1992 |
| WO | 93/25189 | 12/1993 |
| WO | 94/06440 | 3/1994 |
| WO | WO-96/03115 | 2/1996 |
| WO | WO-96/19921 | 7/1996 |
| WO | 96/24325 | 8/1996 |
| WO | 96/26711 | 9/1996 |
| WO | WO-96/27376 | 9/1996 |
| WO | WO-96/39119 | 12/1996 |
| WO | 97/03638 | 2/1997 |
| WO | WO-97/39745 | 10/1997 |
| WO | 98/17282 | 4/1998 |
| WO | WO-98/18472 | 5/1998 |
| WO | WO-98/19654 | 5/1998 |
| WO | WO-98/21955 | 5/1998 |
| WO | WO-98/23291 | 6/1998 |
| WO | WO-98/36733 | 8/1998 |
| WO | 98/52536 | 11/1998 |
| WO | WO-99/08649 | 2/1999 |
| WO | WO-99/20250 | 4/1999 |
| WO | WO-99/37282 | 7/1999 |
| WO | 99/53923 | 10/1999 |
| WO | WO-00/09082 | 2/2000 |
| WO | WO-00/15193 | 3/2000 |
| WO | 00/23051 | 4/2000 |
| WO | WO 00/62776 | 4/2000 |
| WO | 00/33825 | 6/2000 |
| WO | 00/38731 | 7/2000 |
| WO | WO-00/61076 | 10/2000 |
| WO | WO 00/72805 | 12/2000 |
| WO | WO-00/76461 | 12/2000 |
| WO | 01/05366 | 1/2001 |
| WO | 01/10961 | 2/2001 |
| WO | WO-01/08681 | 2/2001 |
| WO | 01/53198 | 7/2001 |
| WO | 01/54212 | 7/2001 |
| WO | 01/62209 | 8/2001 |
| WO | WO-01/54679 | 8/2001 |
| WO | WO-01/70242 A2 | 9/2001 |
| WO | 01/82890 | 11/2001 |
| WO | 01/85102 | 11/2001 |
| WO | 01/85128 | 11/2001 |
| WO | WO-01/82880 | 11/2001 |
| WO | 01/95728 | 12/2001 |
| WO | WO 02/00820 | 1/2002 |
| WO | WO 02/07685 | 1/2002 |
| WO | 02/015860 | 2/2002 |
| WO | 02/15873 | 2/2002 |
| WO | WO-02/28435 | 4/2002 |
| WO | WO-02/41847 A1 | 5/2002 |
| WO | WO-02/43490 | 6/2002 |
| WO | WO-02/062324 | 8/2002 |
| WO | WO 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | WO-03/051294 | 6/2003 |
| WO | 03/055454 | 7/2003 |
| WO | WO 03/053292 | 7/2003 |
| WO | WO-03/055445 | 7/2003 |
| WO | 03/070301 | 8/2003 |
| WO | 03/071995 | 9/2003 |
| WO | WO-03/075851 | 9/2003 |
| WO | 03/097002 | 11/2003 |
| WO | WO-03/092641 | 11/2003 |
| WO | 2004/017962 | 3/2004 |
| WO | 2004/037197 | 5/2004 |
| WO | WO-2004/037225 | 5/2004 |
| WO | 04/03284 | 8/2004 |
| WO | 2004/064769 | 8/2004 |
| WO | WO-2004/064833 | 8/2004 |
| WO | WO-2004/071479 A1 | 8/2004 |
| WO | 2004/078158 | 9/2004 |
| WO | WO-2004/078896 | 9/2004 |
| WO | 2004/093895 | 11/2004 |
| WO | WO-2004/0112780 | 12/2004 |
| WO | WO 2005/011567 | 2/2005 |
| WO | WO-2005/011567 A2 | 2/2005 |
| WO | WO-2005/018530 | 3/2005 |
| WO | WO-2005/018530 A2 | 3/2005 |
| WO | WO-2005/032522 | 4/2005 |
| WO | WO-2005/044219 | 5/2005 |
| WO | 2005/063224 | 7/2005 |
| WO | WO-2005/065652 | 7/2005 |

(56) References Cited

FOREIGN PATENT DOCUMENTS

| WO | WO-2005/076697 | 8/2005 |
|---|---|---|
| WO | WO-2005/097068 | 10/2005 |
| WO | 2005/102282 | 11/2005 |
| WO | WO-2005/102539 A | 11/2005 |
| WO | WO 2005/117813 | 12/2005 |
| WO | WO-2005/117813 | 12/2005 |
| WO | WO-2006/003481 A2 | 1/2006 |
| WO | 2006/011046 | 2/2006 |
| WO | 2006/020682 | 2/2006 |
| WO | WO-2006/010589 | 2/2006 |
| WO | 2006/028339 | 3/2006 |
| WO | WO-2006/031271 | 3/2006 |
| WO | 2006/045170 | 5/2006 |
| WO | 2006/079632 | 8/2006 |
| WO | 2006/081327 | 8/2006 |
| WO | WO-2006/091229 | 8/2006 |
| WO | WO-2006/100485 | 9/2006 |
| WO | 2006/121610 | 11/2006 |
| WO | 2006/122158 | 11/2006 |
| WO | WO-2006/120682 | 11/2006 |
| WO | WO-2006/129161 | 12/2006 |
| WO | WO-2006/131784 | 12/2006 |
| WO | WO-2007/007208 | 1/2007 |
| WO | WO 2007/010494 | 1/2007 |
| WO | WO-2007/012977 | 2/2007 |
| WO | WO-2007/023396 | 3/2007 |
| WO | WO-2007/031621 A2 | 3/2007 |
| WO | WO-2007/039825 | 4/2007 |
| WO | WO-2007/050543 | 5/2007 |
| WO | WO-2007/054818 | 5/2007 |
| WO | WO-2007/072216 | 6/2007 |
| WO | WO 2007/082698 | 7/2007 |
| WO | WO-2007/085899 | 8/2007 |
| WO | WO-2007/085902 | 8/2007 |
| WO | WO-2007/099396 | 9/2007 |
| WO | 2007/111962 | 10/2007 |
| WO | 2008/010963 | 1/2008 |
| WO | WO-2008/008397 | 1/2008 |
| WO | 2008/041045 | 4/2008 |
| WO | WO-2008/038147 | 4/2008 |
| WO | WO-2008/075207 | 6/2008 |
| WO | WO-2008/087148 | 7/2008 |
| WO | WO 2008/110872 | 9/2008 |
| WO | WO-2008/110872 A2 | 9/2008 |
| WO | 2008/152444 | 12/2008 |
| WO | WO-2009/007785 A2 | 1/2009 |
| WO | WO-2009/069006 A2 | 6/2009 |
| WO | WO-2009/072007 A2 | 6/2009 |
| WO | WO-2009/087578 A2 | 7/2009 |
| WO | WO-2009/090495 A2 | 7/2009 |
| WO | WO-2009/090558 A2 | 7/2009 |
| WO | WO-2009/098595 A2 | 8/2009 |
| WO | 2011/039637 | 4/2011 |
| WO | 2011/039638 | 4/2011 |
| WO | WO 2011/039637 | 4/2011 |
| WO | WO 2011/138678 | 11/2011 |
| WO | WO 2013/136192 | 9/2013 |

OTHER PUBLICATIONS

Benet, et al., Application of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Carbowax 1000MSDS; http://www.sciencelab.com/xMSDS-Polyethylene_glycol_1000-9926622. Accessed Dec. 13, 2008, 6 pages.
Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Denatonium Benzoate http://www.newdruginfo.com/pharmaceopeia/usp28/v28230/usp28nf23s0_m22790.htm Accessed Dec. 9, 2008, 2 pages.
Edirisinghe, et al., "Effect of fatty acids on endothelium-dependent relaxation in the rabbit aorta", Clin Sci (Lond). Aug. 2006; 111(2): 145-51.
Emulsifiers with HLB values. http://www.theherbarie.com/files/resources-center/formulating/Emulsifiers_HLB_Values.pdf accessed Aug. 5, 2009 (3 pps).
Encyclopedia of Pharmaceutical Technology, Second Edition, vol. 3, Copyright 2002.
Ethanol, Accessed http://www.sigmaaldrich.com/catalog/ProductDetail.do?N4=E7023SIAL&N5=SEARCH_CONCAT_PNOBRAND_KEY&F=SPEC Dec. 9, 2008, 2 pages.
European Patent Application No. 06831721, Official Action, Feb. 3, 2009, 9 pages.
Flick, Cosmetic and Toiletry Formulations, vol. 5, 2nd Edition, Copyright 1996.
Fontana, Anthony, J., "Water Activity: Why it is Important for Food Safety," International Conference on Food Safety, Nov. 16-18, 1998, 9 pages.
Galligan, John et al., "Adhesive Polyurethane Liners for Anterior Restorations," J. Dent. Res., Jul.-Aug. 1968, pp. 629-632.
Gill, A.M, et al., "Adverse Drug Reactions in a Paediatric Intensitve Care Unit," Acta Paediatr 84:438-441, 1995.
Hall, Karla, "Diaper Area Hemanglomas: A Unique Set of Concerns," http://members.tripod.com/~Michelle_G/diaper.html, Dec. 1, 2008, 8 pages.
http://ibabydoc.com/online/diseaseeczema.asp., Atopic Dermatitis, Copyright 2000.
http://www.agworkshop.com/p3.asp, AG&Co. Essential oil workshop.
International Search Report and Written Opinion, International Application No. PCT/IB2006/003628, Foamix Ltd., Dec. 7, 2007, 15 pages.
International Search Report and Written Opinion, International Application No. PCT/US2007/004459, Foamix Ltd., Dec. 9, 2008, 2 pages.
International Search Report for International Application No. PCT/IB2006/003974, Feb. 25, 2008 (7 pages).
International Search Report, International Patent Application No. PCT/IB2007/003463, Foamix, Ltd., Jul. 18, 2008, 6 pages.
International Search Report, International Patent Application No. PCT/IB2007/003759, Foamix Ltd., Jul. 8, 2008 (7 pages).
Kanamoto, et al., "Pharmacokinetics of two rectal dosage forms of ketoprofen in patients after anal surgery," J Pharmacobiodyn., Mar. 1998; 11(3):141-5.
Kathon ™CG (product information sheet by Rohm and Haas, Jun. 2006).
Kinnunen, Contact Dermatitis Sep. 1989; 21(3): 154-8, 2 pages.
Koerber, S., "Humectants and Water Activity," Water Activity News, 2000, ISSN No. 1083-3943, 8 pages.
Licking Vaginal Dryness without a Prescription. Accessed http://www.estronaut.com/a/vag_dryness.htm on Dec. 14, 2008.
Machine Translation of JP-08165218 (1996).
MMP Inc. International Development and Manufacturing, "Formulating specialities," http://mmpinc.com.
Pendergrass, "The shape and dimensions of the human vagina as seen in three-dimensional vinyl polysiloxane casts," Gynecol Obstet. Invest. 1996:42(3):178-82 (abstract).
Progesterone MSDS. http://www.usp.org.pdf.EN/referenceStandards/msds/1568007.pdf on Dec. 14, 2002, 5 pages.
Psoriasis. http://www.quickcare.org/skin/causes-of-psoriasis.html. Accessed Sep. 9, 2010.
Rosacea. http://clinuvel.com/skin-conditions/common-skin-conditions/rosacea#h0-6-prevention. Accessed Sep. 9, 2010.
Scott as Published in Pharmaceutical Dosage Forms; Disperse Systems, vol. 3, Copyright 1998.
Seborrheic Dermatitis. http://www.cumc.columbia.edu/student/health/pdf/R-S/Seborrhea%20Dermatitis.pdf. Access Sep. 9, 2010.

(56) References Cited

OTHER PUBLICATIONS

Shear, et al., "Pharmacoeconomic analysis of topical treatments for tinea infections," Pharmacoeconomics. Mar. 1995; 7(3); pp. 251-267 (abstract only).
Sigma Aldrich, "HLB-Numbers in Lithography Nanopatterning," http://www.sigmaaldrich.com/materials-science/micro-and-nanoelectronics/lithography-nanopatterning/hlb-numbers.html, accessed: Feb. 2, 2009, pp. 1-3.
Simovic. International Journal of Cosmetic Science. vol. 2 (2): abstract only.
Skin Biology, CP Serum—Copper-Peptide Serum for Skin Regeneration and Reducing Wrinkles, Skin Biology, http;//web.archive.org/web/20030810230608/http://www.skinbio.com/cpserum.html, Dec. 1, 2008, 21 pages.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).
Tan et al., "Effect of Carbopol and Polyvinylpyrrolidone on the Mechanical, Rheological, and Release Properties of Bioadhesive Polyethylene Glycol Gels," AAPS PharmSciTech, 2000; 1 (3) article 24 (2000), 10 pages.
Tarumoto, et al., Studies on toxicity of hydrocortisone 17-butyrate 21-propionate -1. Acute toxicity of hydrocortisone 17-butyrate 21-propionate and its analogues in mice, rats and dogs (author's trans), J Toxicol Sci., Jul. 1981; 6 Suppl: 1-16.
Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008.
Wormser et al., Early and topical treatment with povidone-iodine ointment reduces, and sometimes prevents, skin damage following heat stimulus, Letters to the Editor, Burns, 1998, 24, 383.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
Ethanol, Accessed http://www.sigmaaldrich.com/catalog/ProductDetail.do?N4=E7023SIAL&N5=SEAR-CH.sub.—CONCAT.sub.—PNOBRAND.sub.—KEY&F=SPEC Dec. 9, 2008, 2 pages.
Graves, S. et al. "Structure of Concentrated Nanoemulsions." The Journal of Chemical Physics . . . 122 America Institute of Physics. Published Apr. 1, 2005. 6 pages.
Karasu, T.B. et al. "Treatment of Patients with Major Depressive Disorder, Second Edition," pp. 1-78, 2000.
Kumar, J. et ak., "Application of Broad Spectrum Antiseptic Povidone Iodine as Powerful Action: A Review," Journal of Pharmaceutical Science and Technology vol. 1(2), 2009, 48-58.
Martindale. 33 ed. London, Bath Press, 2002. pp. 1073 and 1473.
Metronidazole. www.usp.org/pdf/EN/veterinary/metronidazole.pdf. accessed Sep. 10, 2009, 4 pages.
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Prescription Information for Aldara, Mar. 2007 (29 pages).
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Seborrheic Dermatitis, http://www.cumc.columbia.edu/student/health/pdf/R-S/Seborrhea%20Dermatitis.pdf. Access Sep. 9, 2010, 2 pages.
Sigma Aldrich, "HLB-Numbers in Lithography Nanopatterning," http://www.sigmaaldrich.com/materials-science/micro-and-nanoelectronics/l-ithography-nanopatterning/hlb-numbers.html, accessed: Feb. 2, 2009, pp. 1-3.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 2010, 3 pages.
Wormser, Early topical treatment with providone-iodine ointment reduces, and sometimes prevents, skin damage following heat stimulus, Letter to the Editor, Burns 24, pp. 383, 1998.
Glaser, et al., Hyperhidrosis: A Comprehensive and Practical Approach to Patient Management, Expert Rev. Dermatol. 1(6), 773-775 (2006).
Merck index, 10th edition, Merck & Co., Inc.: Rahway, NJ, 1983, pp. 39 (entry 242 for allantoin).
Hall, Karla, "Diaper Area Hemangiomas: A Unique Set of Concerns," http://members.tripod.com/.about.Michelle.sub.—G/diaper.html, Dec. 1, 2008, 8 pages.
Hallstar. Retrieved online on Jun. 4, 2011. <URL:http://www.hallstar.com/pis.php?product=1H022>. 1 page.
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Hashim, et al. "Tinea versicolor and visceral leishmaniasis," Int J Dermatol., Apr. 1994; 33(4), pp. 258-259 (abstract only).
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
Hormones. Http://www.greenwillowtree.com/Page.bok?file=libido.html. Jan. 2001.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
Hydroxyethylcellulose. Http: //terpconnect.umd.edu/-choi/MSDS/Sigma-Aldrich/Hydroxyethyl%20Cellulose, 5 pages, Jan. 14, 2004.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

(56) References Cited

OTHER PUBLICATIONS

Izquierdo, P. et al. "Formation and Stability of Nano-Emulsions Prepared Using the Phase Inversion Temperature Method." University of Barcelona. Sep. 17, 2001. 1 page.

Jan. "Troubled Times: Detergent Foam." http://zetatalk.com/health/theall7c.htm. Accessed Feb. 9, 2012. 2 pages.

Kalkan, et al., The Measurement of Sweat Intensity Using a New Technique, Tr. J. of Medical Sciences 28, 515-517 (1998).

Kanamoto, et al., "Pharmacokinetics of two rectal dosage forms of ketoprofen in patients after anal surgery," J Pharmacobiodyn., Mar. 1988; 11(3):141-5.

Kathon.TM. CG (product information sheet by Rohm and Haas, Jun. 2006).

Kim, "Stability of Minoxidil in Aqueous Solution", Yakhak Hoechi, 30(5):228-231 (1986)—Abstract, 1 page.

Kinnunen, "Skin reactions to hexylene glycol," Contact Dermatitis Sep. 1989; 21(3): 154-8.

Kleber, M.D., H.D. et al., "Treatment of Patients with Substance Use Disorders, Second Edition," pp. 1-276, 2006.

Kreuter, J. "Nanoparticles and microparticles for drug and vaccine delivery," J. Anat. (1996) 189, pp. 503-505.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." J. Am. Acad. Dermatol. 45:487-498. Oct. 2001.

Lebwohl et al., "A randomized, double-blind, placebo-controlled study of clobestasol propionate 0.05% foam in the treatment of nonscalp psoriasis," International Journal of Dermatology, 2002, 41(5): 269-274.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Leung, et al., "Bioadhesive Drug Delivery in Water-Soluble Polymers," American Chemical Society, Chapter 23, 1991, pp. 350-366.

Licking Vaginal Dryness without a Prescription. Accessed http://www.estronaut.com/a/vag.sub.—dryness.htm on Dec. 14, 2008, 3 pages.

Lippacher, A. et al. "Liquid and Semisolid SLN Dispersions for Topical Application" Rheological Characterization. European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Martindale, The extra pharmacopoeia [28th] edition, Eds.: Reynolds, J.E.F. and Prasad, A.B., The Pharmaceutical Press, London, pp. 862-864, 1982.

Material Safety Data Sheet, Science Lab.com, Polyethylene Glycol 1000, MSDS, Nov. 6, 2008, 6 pages.

Merck index, 14th edition, O'Neill, ed., 2006, entry for p-amino benzoic acid.

Merck index, 14th edition, O'Neill, ed., 2006, entry for zinc oxide.

Merck Index, An Encyclopedia of Chemicals, Drugs, and Biologicals. 13th Edition. O'Neil et al eds. Entries 1058, 2350, 6143, and 8803. 2001. 7 pages.

Messenger, et al., "Minoxidil: Mechanisms of Action on Hair Growth", British Journal of Dermatology, 150:186-194 (2004).

Metz, et al., "A Phase I Study of Topical Tempol for the Prevention of Alopecia Induced by Whole Brain Radiotherapy", Clinical Cancer Research, 10:6411-6417 (2004).

Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.

Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.

Nietz, "Molecular orientation at surfaces of solids," J. Phys. Chem., 1928, 32(2): 255-269.

No Author Listed. "Opitmization of Nano-Emulsions Production by Microfluidization." European Food Research and Technology. vol. 225, No. 5-6. Sep. 2007. Abstract. 1 page.

Office Action for U.S. Appl. No. 11/430,437, Tamarkin et al., May 9, 2008, 27 pages.

Office Action received from the U.S. Appl. No. 11/430,599, Jul. 28, 2008 (59 pages).

Pendergrass, "The shape and dimension of the human vagina as seen in three-dimensional vinyl polysiloxane casts," Gynecol Obstet. Invest. 1996:42(3):178-82.

Prevent. (2007). In the American Heritage Dictionary of the English Language. Retrieved from http://www.credoreference.com/entry/hmdictenglang/prevent. 1 page.

Psoriasis, http://www.quickcare.org/skin/causes-of0psoriasis.html. Accessed Sep. 9, 2010—3 pages.

Purcell, Hal C. "Natural Jojoba Oil Versus Dryness and Free Radicals." Cosmetics and Toiletries Manufacture Worldwide. 1988. 4 pages.

Savin, et al., "Tinea versicolor treated with terbinafine 1% solution," Int J. Dermatol, Nov. 1999; 38(11), pp. 863-865.

Schulze, M.D., Harry "Iodine and Sodium Hypochlorite as Wound Disinfectants," The British Medical Journal, pp. 921-922, 1915.

Scientific Discussion for the approval of Aldara, EMEA 2005 (10 pages).

Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.

Shim, et al., "Transdermal Delivery of Mixnoxidil with Block Copolymer Nanoparticles", J. Control Release, 97(3):477-484 (2004)—Abstract, 1 page.

Silicone. Definition. Retrieved Apr. 19, 2011 from http://www.oxforddictionaries.com/definition/silicone?view=uk. 1 page.

Simovic, S. et al., "The influence of Processing Variables on Performance of O/W Emulsion Gels Based on Polymeric Emulsifier (Pemulen ÒTR-2NF)," International Journal of Cosmetic Science, vol. 2(2): abstract only. Dec. 24, 2001, 1 page.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Sreenivasa, et al., "Preparation and Evaluation of Minoxidil Gels for Topical Application in Alopecia", Indian Journal of Pharmaceutical Sciences, 68(4):432-436 (2006), 11 pages.

Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.

Sweetman, Sean C. Martindale: The Complete Drug Reference. 33rd Edition. London. Pharmaceutical Press. Jun. 21, 2002. pp. 1073 and 1473. 5 pages.

Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Tanhehco, "Potassium Channel Modulators as Anti-Inflammatory Agents", Expert Opinion on Therapeutic Patents, 11(7):1137-1145 (2001)—Abstract, 3 pages.

Tarumoto, et al., Studies on toxicity of hydrocortisone 17-butyrate 21-propionate -1. Accute toxicity of hydrocortisone 17-butyrate 21-propionate and its analogues in mice, rats and dogs (author's trans), J Toxicol Sci., Jul. 1981; 6 Suppl: 1-16 (Abstract only).

Tata, et al., "Penetration of Minoxidil from Ethanol Propylene Glycol Solutions: Effect of Application Volume on Occlusion", Journal of Pharmaceutical Sciences, 84(6):688-691 (1995).

Third Party Submission for U.S. Appl. No. 12/014,088, filed Feb 4, 2009, 4 pages.

Tones-Rodriguez, JM., "New topical antifungal drugs," Arch Med Res. 1993 Winter; 24(4), pp. 371-375 (abstract).

(56) References Cited

OTHER PUBLICATIONS

Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Yamada and Chung, "Crystal Chemistry of the Olivine-Type $Li(Mn_yFe_{1-y})PO_4$ and $(Mn_yFe_{1-y})PO_4$ as Possible 4 V Cathode Masterials for Lithium Batteries," J. Elecytrochemical Soc., 2001, 148(8): A960-967.
Gill, A.M, et al., "Adverse Drug Reactions in a Paediatric Intensive Care Unit," Acta Paediatr 84:438-441, 1995.
Gladkikh, "Ascorbic Acid and Methods of Increasing its Stability in Drugs", Translated from Khimiko-Farmatsevticheskii Zhurnal, 4(12):37-42 (1970)-1 page.
Groveman, et al., "Lack of Efficacy of Polysorbate 60 in the Treatment of Male Pattern Baldness", Arch Intern Med, 145:1454-1458 (1985).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hargreaves, "Chemical Formulation, An Overview of Surfactant-Based Preparations Used in Everyday Life", *The Royal Society of Chemistry*, pp. 114-115 (2003).
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).
Kang,et al., "Enhancement of the Stability and Skin Penetration of Vitamin C by Polyphenol", Immune Netw., 4(4):250-254 (2004)—Abstract, 1 page.
Koerber, S., "Humectants and Water Activity," Water Activity News, 2000, ISSN No. 1083-3943.
Li, et al., "Solubility Behavior of Imiquimod in Alkanoic Acids", Abstract 3029, Pharmaceutical Research, vol. 14, No. 11 Supplemental (November), p. S475 (1997), 2 pages.
Material Safety Data Sheet, Progesterone, Apr. 26, 2006, 5 pages.
Merriam Webster Online Dictionary [online] retrieved from http://www.merriam-webster.com/cgi-bin/dictionary?book=dictionary &va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," J. Electrochemical Soc., 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.
Ravet et al., "Electroactivity of natural 503-507 and synthetic triphylite," J. of Power Sources, 2001, 97-98: 503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Rosacea, http://clinuvel.com/skin-conditions/common-skin-conditions/rosacea#h0-6-prevention. Accessed Sep. 9, 2010, 5 pages.
Schmidt A., "Malassezia furfur: a fungus belonging to the physiological skin flora and its relevance in skin disorders," Curtis., Jan. 1997; 59(1), pp. 21-24 (abstract).
Scott as Published in Pharmaceutical Dosage Forms; Disperse Systems, vol. 3, Copyright 1998, 120 pages.
Shrestha et al., Forming properties of monoglycerol fatty acid esters in nonpolar oil systems, *Langmuir*, 2006, 22: 8337-8345.
Sigma-Aldrich, Material Safety Data Sheet, Hydroxyethyl Cellulose, Mar. 3, 2004, 5 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Stehle et al., Uptake of minoxidil from a new foam formulation devoid of propylene glycol to hamster ear hair follicles, J. Invest. Dermatol., 2005, 124(4), A101.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tata, et al., "Relative Influence of Ethanol and Propylene Glycol Cosolvents on Deposition of Minoxidil into the Skin", Journal of Pharmaceutical Sciences, 83(10):1508-1510 (1994).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Tsai, et al., "Effect of Minoxidil Concentration on the Deposition of Drug and Vehicle into the Skin", International Journal of Pharmaceutics, 96(1-3):111-117 (1993)—Abstract, 1 page.
Wermuth, C.G. "Similarity in drugs: reflections on analogue design," Drug Discovery Today, vol. 11, Nos. 7/8, Apr. 2006, pp. 348-354.
"Coal tars and coal-tar pitches," *Report on Carcinogens, Twelfth Edition*, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," J. Surg. Res., 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," J. Med. Chem., 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.

(56) References Cited

OTHER PUBLICATIONS

Ebadi et al., "Healing effect of topical nifedipine on skin wounds of diabetic rats," *DARU*, 2003, 11(1):19-22.
Effendy and Maibach. "Surfactants and Experimental Irritant Contact Dermatitis." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluhr et al., "Glycerol accelerates recovery of barrier function in vivo," *Acta Derm. Venereol,*. 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990.
Hwang et al. "Isolation and identification of mosquito repellents in *Artemisia vulgaris*," *J. Chem. Ecol.*, 11: 1297-1306, 1985.
Knight et al., "Topical diltiazem ointment in the treatment of chronic anal fissure," *Br. J. Surg.*, 2001, 88(4):553-6.
Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem,. Toxic.*, 1986, 24:495-196.
Osborne and Henke, "Skin Penetration Enhancers Cited in the Technical Literature," *Pharm. Technology*, Nov. 1997, pp. 58-86.
Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.
Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3,4-dehydroretinoic acid in human keratinoacytes are similar and correlate with receptor affinities and transactivation properties," *J. Invest. Dermatology*, 1994, 102: 49-54.

USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. Am. Acad. Dermatol.*,1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3):190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No. 2003 (See Directive 67/548/EEC OJ 196, 16.8, 1967, p. 1.
Tzen et al., Lipids, proteins and structure of seed oil bodies from diverse species; *Plant Physiol.*, 1993, 101:267-276.
Brown et al. "Structural dependence of flavonoid interactions with $Cu^{2+}$ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its protoprotection of skin," *J Invest Dermatol*, 2005, 125:826-32.
International Preliminary Report on Patentability from PCT/IB2007/004628, dated Jun. 3, 2009, 6 pages; International Search Report, dated May 6, 2009, 4 pages.
"Arquad HTL8-MS," *AkzoNobel Functional Applications*, retrieved on Mar. 18, 2013, Retrieved from the Internet: <URL: http://sc.akzonobel.com/en/fa/Pages/product-detail.aspx?prodID=8764>, 1 page.
"Burn patients need vitamin D supplements." *Decision News Media*, Jan. 23, 2004, http://www.nutraingredients.com/Research/Burn-patients-need-vitamin-D-supplements, Accessed: May 5, 2010.
"Can tuberous sclerosis be prevented?," *Sharecare*, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
"Crohn's Disease," *Merch Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
"Dacarbazine," *Chemical Book*, 2010, retrieved on Oct. 18, 2013, <URL: http://www.chemicalbook.com/ChemicalProductProperty_EN_CB7710656.htm>, 2 pages.
"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.
"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.
"Gas Gangrene," Merch Manual Home Edition, 2008, retrieved on Jan. 16, 2013, <http://www.merckmanuals.com/home/infections/bacterial_infections/gas_gangrene.html?qt=gasgangrene&alt=sh>1 page.
"HLB Systems", http://pharmcal.tripod.com/ch17.htm, Accessed Sep. 17, 2010, pp. 1-3.
"Human Immunodeficiency Virus Infection," Merch Manual Home Edition, 2008, retrieved on Jan. 16, 2013, <http://www.merckmanuals.com/home/infections/human_immunodeficiency_virus_hiv_

(56) References Cited

OTHER PUBLICATIONS infection/human_immunodeficiency_virus_infection. html?qt=human immunodeficiency virus infection&alt=sh>, 11 pages.
"Minocycline (DB01017)," *DrugBank*, Feb. 8, 2013, retrieved on Aug. 15, 2013, <http://www.drugbank.ca/drugs/DB01017>, 10 pages.
"Minocycline" accessed on Oct. 21, 2011 at en.wikipedia.org/wiki/Minocycline, 7 pages.
"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.
"Product Data Sheet for Meclocycline," *bioaustralis fine chemicals*, Jun. 28, 2013, 1 page.
"Reaction Rate" Accessed at en.wikipedia.org/wiki/Reaction_rate on Dec. 18, 2011, 6 pages.
"Shear," Vocabulary.com, retrieved on Aug. 23, 2013, <URL: https://www.vocabulary.com/dictionary/shear>, 3 pages.
"Sheer," Vocabulary.com, retrieved on Aug. 23, 2013, <URL: https://www.vocabulary.com/dictionary/sheer>, 3 pages.
"View of NCT01171326 on Dec. 7, 2010," ClinicalTrials.gov archive, Dec. 7, 2010, retrieved on Sep. 9, 2013, <http://clinicaltrials.gov/archive/NCT01171326/2010_12_07>, 4 pages.
"View of NCT01362010 on Jun. 9, 2011," ClinicalTrials.gov archive, Jun. 9, 2011, retrieved on Sep. 9, 2013, <http://clinicaltrials.gov/archive/NCT01362010/2011_06_09>, 3 pages.
"What is TSC?," *Tuberous Sclerosis Alliance*, Jan. 1, 2005, retrieved on Feb. 6, 2014, <URL: http://www.tsalliance.org.pages.aspx?content=2>, 3 pages.
'Niram Chemicals' [online]. Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Abrams et al., "Ciclopirox gel treatment of scalp seborrheic dermatitis," *Hydroxy-Piridones as Antifungal Agents with Special Emphasis on Onychomycosis*, 1999, Chapter 8, 45-50.
Adachi, Shuji. "Storage and Oxidative Stability of O/W/ Nano-emulsions." Foods Food Ingredients. J. Jpn. vol. 209, No. 11. 2004. 1 page.
Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)-Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology*, 1978, 1:33-36.
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blaney and Cook, "Topical use of tetracycline in the treatment of acne," *Arch Dermatol*, Jul. 1976, 112:971-973.
Blute, "Phase behavior of alkyl glycerol ether surfacants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)-Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).
Burton, et al., "Hypertrichosis Due to Minoxidil", British Journal of Dermatology, 101:593-595 (1979).
Campos, et al., "Ascorbic Acid and Its Derivatives in Cosmetic Formulations", Cosmetics and Toiletries, 115(6):59-62 (2000)-Abstract, 1 page.
Carelli, et al., "Effect of Vehicles on Yohimbine Permeation Across Excised Hairless Mouse Skin", Pharm Acta Helv, 73(3):127-134 (1998)-Abstract, 1 page.
Cetearyl Alcohol, Natural Wellbeing, Copyrigh 2001-2012, retrieved on Apr. 10, 2014, http://www.naturalwellbeing.com/learning-center/Cetearyl_Alcohol, 3 pages.
Chebil, et al., "Soulbility of Flavonoids in Organic Solvents", J. Chem. Eng. Data, 52(5):1552-1556 (2007)-Abstract, 1 page.
Chevrant-Breton, et al., "Etude du Traitement Capillaire <<Bioscalin>> dans les Alopecies Diffuses de la Femme", Gazette Medicale, 93(17):75-79 (1986) [English abstract].
Chiang, et al., "Bioavailability Assessment of Topical Delivery Systems: In Vitro Delivery of Minoxidil from Prototypical Semi-Solid Formulations", Int. J. Pharm, 49(2):109-114 (1989)-Abstract, 1 page.
Chinnian, et al., "Photostability Profiles of Minoxidil Solutions", PDA J. Pharm Sci Technol., 50(2):94-98 (1996)-Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.
Croda. Aracel 165 Product Summary. 2011 (no month given). 1 page.
Cunha, "Minocycline versus Doxycycline in the treatment of Lyme Neuroborreliosis," *Clin. Infect. Diseases*, 2000, 30: 237-238.
Dawber, et al., "Hypertrichosis in Females Applying Minoxidil Topical Solution and in Normal Controls", JEADV, 17:271-275 (2003).
Dentinger, et al., "Stability of Nifedipine in an Extemporaneously Compounded Oral Solution", American Journal of Health-System Pharmacy, 60(10):1019-1022 (2003)-Abstract, 1 page.
disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224.
Durian et al., "Scaling behavior in shaving cream," The Americal Physical Society, Dec. 1991, 44(12):R7902-7905.
Edens, et al., "Storage Stability and Safey of Active Vitamin C in a New Dual-Chamber Dispenser", Journal of Applied Cosmetology, 17(4):136-143 (1999)-Abstract, 1 page.
Edwards, "Imiquimod in Clinical Practice", J. Am Acad Dermatol., 43(1, Pt 2):512-517 (2000)-Abstract, 1 page.
Esposito, E. et al. "Nanosystems for Skin Hydration: A Comparative Study." International Journal of Cosmetic Science. 29. 2007. pp. 39-47.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)-Abstract, 1 page.

(56) References Cited

OTHER PUBLICATIONS

Final Office Action for U.S. Appl. No. 11/430,437, Tamarkin et al., Dec. 16, 2008, 24 pages.

Fontana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Gelbard et al. "Primary Pediatric Hyperhidrosis: A Review of Current Treatment Options." Pediatric Dermatology. 2008. 25 (6). pp. 591-598.

Google search strategy for minocycline solubility, retrieved on Aug. 15, 2013, <http://www.googl.com/search?rls=com.microsoft%3Aen-us%3AIE-SearchBox&q-melocycline+solubility>, 1 page.

Harry, "Skin Penetration," The British Journal of Dermatology and Syphillis, 1941, 53:65-82.

Joseph, "Understanding foams & foaming," University of Minnesota (1997), at http://www.aem.umn.edu/people/faculty/joseph/archive/docs/understandingfoams.pdf, pp. 1-8.

Lee et al., "Historical review of melanoma treatment and outcomes," Clinics in Dermatology, 2013, 31: 141-147.

Livingstone and Hubel, "Segregation of form, color, movement, and depth: Anatomy, physiology, and perception," Science, May 1988, 240:740-749.

Merck Manual Home Edition. "Excessive Sweating: Sweating Disorders." Accessed Apr. 14, 2011 at www.merckmanuals.com/home/print/sec18/ch206/ch206c.html. 2 pages.

*Molins PLC v. Textron Inc.*, 48 F.3d 1172, 33 USPQ2d 1823 (Fed. Cir. 1995), 19 pages.

Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.

Neves et al., "Rheological Properties of Vaginal Hydrophilic Polymer Gels," Current Drug Delivery, 2009, 6:83-92.

Prud'homme et al., Foams: theory, measurements and applications, Marcel Dekker, Inc., 1996, 327-328.

Purdy et al., "Transfusion-transmitted malaria: unpreventable by current donor exclusion guidelines?" Transfusion, Mar. 2004, 44:464.

Reregistration Eligibility Decision for Pyrethrins, EPA, Jun. 7, 2006, 108 pages.

Schmolka, "A review of block polymer surfactants," *Journal of the American Oil Chemists Society*, Mar. 1977, 54: 110-116.

Schott, "Rheology," *Remington's Pharmaceutical Sciences*, 17th Edition, 1985, 330-345.

Sciarra, "Aerosol Technology," Kirk-Othmer Encyclopedia of Chemical Technology, Jul. 2012, 20 pages.

Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.

Sehgal, " Ciclopirox: a new topical pyrodonium antimycotic agent: A double-blind study in superficial dermatomycoses," British Journal of Dermatology, 1976, 95:83-88.

Softemul-165: Product Data Sheet, Mohini Organics PVT LTD, retrieved Apr. 10, 2014, http://www.mohiniorganics.com/Softemul165.html#, 1 page.

Sonneville-Aubrun, O. et al. "Nanoemulsions: A New Vehicle for Skincare Products." Advances in Colloid and Interface Science. 108-109.. 2004. pp. 145-149.

*Sun Pharmaceutical Industried Ltd.* v. *Eli Lilly and Co.*, 611 F.3d 1381, 95 USPQ2d 1797 (Fed. Cir. 2010),7 pages.

Surfactant. Chemistry Glossary. Http://chemistry.about.com/od/chemistryglossary/g/surfactant.htm, 2012, 1 page.

Tavss et al., "Anionic detergent-induced skin irritation and anionic detergent-induced pH rise of bovine serum albumin," J. Soc. Cosmet. Chem., Jul./Aug. 1988, 39:267-272.

Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.

\* cited by examiner

US 8,795,693 B2

COMPOSITIONS WITH MODULATING AGENTS

CROSS REFERENCE TO RELATED APPLICATIONS

This application claims priority under 35 U.S.C. §119(e) of U.S. Provisional Application Ser. No. 60/861,620, filed on Nov. 29, 2007, which is hereby incorporated by reference.

This application is a continuation-in-part application of co-pending U.S. patent application Ser. No. 10/835,505, filed on Apr. 28, 2004, which claims the benefit of priority under 35 U.S.C. §119(e) to U.S. Patent Application Ser. No. 60/530,015, filed on Dec. 16, 2003, and U.S. Patent Application Ser. No. 60/492,385, filed on Aug. 4, 2003, all hereby incorporated in their entirety by reference.

This application is a continuation in part of U.S. patent application Ser. No. 11/430,599, filed on May 9, 2006, which claims the benefit under 35 U.S.C. §119(e) of U.S. Provisional Patent Application No. 60/784,793, filed on Mar. 21, 2006, and of U.S. Provisional Patent Application No. 60/679,020, filed on May 9, 2005, which are herein incorporated by reference in its entirety.

BACKGROUND

This invention relates to pharmaceutical and cosmetic compositions, particularly waterless compositions.

External topical administration is an important route for the administration of drugs in disease treatment. Many groups of drugs, including, for example, antibiotic, anti-fungal, anti-inflammatory, anesthetic, analgesic, anti-allergic, corticosteroid, anti-psoriasis, retinoid, vitamins and anti-proliferative medications are preferably administered in hydrophobic media, namely ointment. However, ointments often form an impermeable barrier, so that metabolic products and excreta from the wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based products relates to the greasy feeling left following their topical application onto the skin, mucosal membranes and wounds. A further problem of non aqueous compositions is achieving formulations in which the active agent is stable.

Some active agents are known to be generally unstable or susceptible to isomerisation or to breakdown, resulting in loss of activity and the use of stabilizers, anti oxidants antimicrobials and buffers and the like in aqueous compositions to protect active or cosmetic agents is known. The problems of protecting active pharmaceutical and cosmetic agents in waterless environments, such as polar compositions are multifold and can vary according to the type of waterless environment and the nature of the agent being used. It has been surprisingly found that factors like small levels of acid residues in the raw materials can be significant in influencing agent stability. Similarly, the presence of low levels of metal ions can act to catalyze reactions or breakdown. Likewise, the presence of agents in a waterless environment that results in ionization or leads to oxidation can act to cause reactions or breakdown. There is therefore a need for simple and elegant solutions to stabilize active ingredients in a waterless or substantially environment.

It would be particularly advantageous and there is an unmet need to have a waterless vehicle additive that is suitable for use not merely one type of API but is adaptable for use with one or more API's from a wide range of different types of API's with relatively minimal or minor adjustment.

Foams and, in particular, foam emulsions are complicated systems which do not form under all circumstances. Changes in foam emulsion composition, such as by the addition of active ingredients may destabilize the foam. There is, therefore, a need for a foam composition, which provides desirable properties to the skin and can remain stable whilst accommodating a variety of active ingredients.

Formulations based on oil or ointment, emollients have a number of useful attributes making them suitable candidates for topical pharmaceutical and cosmetic compositions including foamable compositions. They are inherently stable and inert which are clearly desirable characteristics. They are able to moisturize and soften the skin and in appropriate amounts can act as a protective or barrier layer and can form a barrier to water. By appropriate formulation they can act to improve drug delivery to the skin and yet remain resistant to being washed off. On the other hand they are by their nature greasy materials and can be difficult to formulate particularly into a topical foamable composition that can deliver substantially uniform and stable composition or foam that ameliorates or overcomes the look and feel of a greasy material, especially where that composition is waterless or substantially so. It is further a problem to incorporate into such a vehicle pharmaceutically effective amounts of one or more active pharmaceutical ingredients such that they are uniformly present throughout the formulation and are effectively delivered without the use of an alcohol in the formulation.

On one level it is far from simple or obvious to produce waterless foamable compositions that when released produce foams of quality suitable for pharmaceutical or cosmetic application. On a further level having realized a carrier that will produce a waterless foam of quality there is an additional difficulty to be overcome, namely how to adapt the formula and achieve a formulation, which can accept a range of various active pharmaceutical and cosmetic agents such that the composition and active agent are stable and the foam produced remains of quality. Specifically, one of the challenges in preparing such waterless or substantially waterless foamable compositions is ensuring that the active pharmaceutical or therapeutic agent does not react, isomerizes or otherwise break down to any significant extent during is storage and use. Particularly, there remains an unmet need for improved, easy to use, stable and non-irritating foam formulations, with unique therapeutic or beneficial properties containing a stable or stabilized active pharmaceutical or cosmetic agent.

There remains an unmet need for improved, easy to use, stable and non-irritating topical foam formulations containing a stable or stabilized active pharmaceutical or cosmetic agent having a therapeutic or beneficial effect, intended for treatment of dermal and mucosal tissues.

SUMMARY

The present invention relates to a waterless composition as a vehicle in which an active pharmaceutical or cosmetic agent, when added is stable or stabilized.

The present invention also relates to a foamable waterless composition as a vehicle in which an active pharmaceutical or cosmetic agent, when added is stable or stabilized by the presence of a modulating agent.

The present invention more particularly relates to modulating agents that are able to be effective in relatively low concentrations and which have little or no significant effect on the compositions and on the foam compositions of the present invention.

According to one or more embodiments there is provided a waterless composition as a vehicle in which a modulating agent is incorporated and which is capable of stabilizing an active pharmaceutical or cosmetic agent, when added.

According to one or more embodiments there is provided a waterless vehicle, an active agent that is susceptible, to one or more of reaction, breakdown, ionization or oxidation and a modulating agent. In an embodiment the waterless vehicle comprises a hydrophobic solvent. In another embodiment it comprises a hydrophilic solvent.

According to one or more embodiments, the carrier, includes: a waterless solvent, a stabilizing surfactant, and or a polymeric agent, and in which is incorporated a modulating agent.

According to one or more embodiments, the carrier is a foamable carrier, and includes: a waterless solvent, a stabilizing surfactant, and or a polymeric agent, and a propellant and in which is incorporated a modulating agent.

In an embodiment the carrier and modulating agent formulation is capable of stabilizing an active pharmaceutical or cosmetic agent in a substantially waterless environment.

According to one or more embodiments there is provided a waterless composition comprising
- one or more active agents and a carrier for topical delivery of the one or more active agents suitable for stabilizing at least one of said one or more active agents, said carrier comprising a waterless solvent and an effective amount of a modulating agent;
- wherein the at least one active agent is chemically unstable in the carrier in the absence of a modulating agent;
- wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent.

According to one or more embodiments of the present invention, pharmaceutical or cosmetic composition is foamable and, includes: a waterless solvent, a stabilizing surfactant, and or a polymeric agent, a modulating agent, a propellant and one or more active pharmaceutical or cosmetic agents.

According to one or more embodiments of the present invention, the active agent itself can have characteristics of a modifying agent.

According to one or more embodiments of the present invention, the carrier, includes:
a. a waterless solvent comprising about 25% to about 98% of at least polar solvent selected from the group consisting of (1) a polyol; and (2) a polyethylene glycol or combinations thereof;
b. a modulating agent;
c. a stabilizing agent selected from the group consisting of a surface-active agent; and about 0.01% to about 5% by weight of at least one polymeric agent or mixtures thereof; wherein the carrier is shakable and wherein if the composition is stored in an aerosol container and comprises a liquefied or compressed gas propellant at a concentration of about 3% to about 25% by weight of the total composition it will upon release expand to form a breakable foam.

According to one or more embodiments the active agent is susceptible to reaction, breakdown, ionization, or oxidization.

According to one or more embodiments of the present invention, the foamable pharmaceutical composition, includes:
1. a waterless solvent comprising about 25% to about 98% of at least polar solvent selected from the group consisting of (1) a polyol; and (2) a polyethylene glycol or combinations thereof;
2. a modulating agent;
3. a stabilizing agent selected from the group consisting of a surface-active agent and about 0.01% to about 5% by weight of at least one polymeric agent;
4. a liquefied or compressed gas propellant at a concentration of about 3% to about 25% by weight of the total composition; and
5. an effective amount of an active pharmaceutical or cosmetic agent;

wherein the carrier is shakable and wherein the composition is stored in an aerosol container and upon release expands to form a breakable foam.

According to one or more embodiments there is provided a foamable waterless composition comprising:
a. a therapeutically effective concentration of one or more active agents;
b. a carrier for topical delivery of the one or more active agents suitable for stabilizing at least one of said one or more active agents, comprising
  i. about 25% to about 98% of at least polar solvent selected from the group consisting of (1) a polyol; and (2) a polyethylene glycol;
  ii. 0% to about 75% of a secondary polar solvent;
  iii. an effective amount of a modulating agent
  iv. a stabilizing agent selected from the group consisting of a surface-active agent; about 0.01% to about 5% by weight of at least one polymeric agent and mixtures thereof.
  v. a liquefied or compressed gas propellant at a concentration of about 3% to about 25% by weight of the total composition wherein the at least one active agent is chemically unstable in the carrier in the absence of a modulating agent;
wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent.
wherein the carrier is shakable or flowable; and
wherein the composition is stored in an aerosol container and upon release expands to form a breakable foam.

The present invention further relates to said composition comprising one or more additional active agents.

The present invention further relates to said composition comprising one or more additional or secondary polar solvents.

In some embodiments, the foamable cosmetic or pharmaceutical composition is non-flammable, wherein said gas propellant contains hydrofluorocarbon.

According to one or more embodiments there is provided a method of treating a disorder of mammalian subject, comprising:
administering a composition to a target site, the composition comprising:
one or more active agents and a carrier for topical delivery of the one or more active agents suitable for stabilizing at least one of said one or more active agents, said carrier comprising a waterless solvent and an effective amount of a modulating agent;

wherein the at least one active agent is chemically unstable in the carrier in the absence of a modulating agent;

wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent.

According to one or more embodiments there is also provided a method of treating a disorder of mammalian subject, comprising:

administering a foamable composition to a target site, the composition comprising:
  a foamable waterless composition comprising:
    a. a therapeutically effective concentration of one or more active agents;
    b. a carrier for topical delivery of the one or more active agents suitable for stabilizing at least one of said one or more active agents, comprising
      i. about 25% to about 98% of at least polar solvent selected from the group consisting of (1) a polyol; and (2) a polyethylene glycol;
      ii. 0% to about 75% of a secondary polar solvent;
      iii. an effective amount of a modulating agent
      iv. a stabilizing agent selected from the group consisting of a surface-active agent; about 0.01% to about 5% by weight of at least one polymeric agent and mixtures thereof.
      v. a liquefied or compressed gas propellant at a concentration of about 3% to about 25% by weight of the total composition
    wherein the at least one active agent is chemically unstable in the carrier in the absence of a modulating agent;
    wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent.
    wherein the carrier is shakable or flowable; and
    wherein the composition is stored in an aerosol container and upon release expands to form a breakable foam.

According to one or more embodiments there is also provided foamable waterless composition comprising:
  a. a therapeutically effective concentration of one or more active agents;
  b. a carrier delivery of the one or more active agents suitable for stabilizing at least one of said one or more active agents, comprising
    i. about 25% to about 98% of at least polar solvent selected from the group consisting of (1) a polyol; and (2) a polyethylene glycol;
    ii. 0% to about 75% of a secondary polar solvent;
    iii. an effective amount of an modulating agent
    iv. a stabilizing agent selected from the group consisting of a surface-active agent; about 0.01% to about 5% by weight of at least one polymeric agent and mixtures thereof.
    v. a liquefied or compressed gas propellant at a concentration of about 3% to about 25% by weight of the total composition
  wherein the at least one active agent is chemically unstable in the carrier in the absence of a modulating agent;
  wherein the modulating agent comprises an effective amount of one or more agents that are capable of impeding said destabilization and or are capable of stabilizing the active agent by chelating a metal ion such that the modulating agent is capable of reducing in the waterless carrier the availability of metal ions so the stability of at least one active agent is improved when compared to its stability in the carrier without the modulating agent;
  wherein the carrier is shakable or flowable; and
  wherein the composition is stored in an aerosol container and upon release expands to form a breakable foam.

According to one or more embodiments there is also provided a carrier where the modulating agent acts by impeding ionization and or by impeding oxidation.

According to one or more embodiments there is also provided a foamable waterless carrier for use with a therapeutically effective concentration of one or more active agents comprising:
  (i) about 25% to about 98% of at least polar solvent selected from the group consisting of (1) a polyol; and (2) a polyethylene glycol; 0% to about 75% of a secondary polar solvent;
  (ii) an effective amount of a modulating agent
  (iii) a stabilizing agent selected from the group consisting of a surface-active agent; about 0.01% to about 5% by weight of at least one polymeric agent and mixtures thereof.
  (iv) a liquefied or compressed gas propellant at a concentration of about 3% to about 25% by weight of the total composition
  wherein at least one active agent if present is susceptible, to one or more of reaction, breakdown, ionization or oxidation;
  wherein the modulating agent comprises an effective amount of one or more agents that are capable of impeding said destabilization and or are capable of stabilizing the active agent primarily by modulating or adjusting the artificial pH of the carrier such that the modulating agent is capable of producing in the waterless carrier an artificial pH or an artificial pH buffering effect at about a pH or pH range in which the stability of at least one active agent is improved when compared to its stability in the carrier without the modulating agent and or by chelating a metal ion such that the modulating agent is capable of reducing in the waterless carrier the availability of metal ions so the stability of at least one active agent is improved when compared to its stability in the carrier without the modulating agent;
  wherein the carrier is shakable or flowable; and
  wherein the composition is stored in an aerosol container and upon release expands to form a breakable foam.

The present invention further provides a method of treating, alleviating or preventing a disorder of mammalian subject, comprising administering a therapeutically effective amount of the above-mentioned compositions to an afflicted target site.

The present invention further provides use of a therapeutically effective amount of the above-mentioned compositions as a medicament or in the manufacture of a medicament.

The present invention further provides a therapeutically effective amount of the above-mentioned compositions for use as a medicament or in the manufacture of a medicament.

All % values are provided on a weight (w/w) basis.

DETAILED DESCRIPTION

In one or more embodiments there is provided a waterless composition for use as a vehicle in which an active pharmaceutical or cosmetic agent, when added is stable or stabilized. Active pharmaceutical and cosmetic agents are more generally referred to as a therapeutic agent.

In one or more embodiments there is provided a waterless composition as a vehicle in which a modulating agent is incorporated and which is capable of stabilizing an active pharmaceutical or cosmetic agent, when added.

In an embodiment the carrier and modulating agent formulation is capable of stabilizing an active pharmaceutical or cosmetic agent in a substantially waterless or mon aqueous environment.

In an embodiment the carrier and modulating agent formulation is capable of stabilizing an active pharmaceutical or cosmetic agent in a substantially waterless environment, where the active agent has low or minimal susceptibility to water and can withstand up to about 10% water and more preferably upto about 5% water.

In one or more embodiments there is provided a waterless composition for use as a vehicle in which an active pharmaceutical or cosmetic agent, when added is stable or stabilized by the presence of a modulating agent.

In one or more embodiments there is provided a foamable waterless composition for use as a vehicle in which an active pharmaceutical or cosmetic agent, when added is stable or stabilized by the presence of a modulating agent.

According to one or more embodiments, it is possible to make excellent lotions, creams, ointments and foams from waterless compositions. Such compositions containing a modulating agent as described herein are ideal carriers for active pharmaceutical ingredients that are soluble in polar solvents and which may be potentially unstable in an aqueous environment, for example, following a change in pH, or the introduction a metal catalyst or in the presence of an ionization or oxidation agent.

It has been found that differences in the level and type of residues in cosmetic and pharmaceutical grade materials and agents can significantly and seriously influence the stability of an active pharmaceutical or cosmetic agent. Whilst it might be expected that active agents would be more stable in pure raw materials with practically no residues it was surprisingly observed that small levels of residues in raw materials were actually helpful in improving the stability of and stabilizing active ingredients in certain waterless compositions. On the other hand active ingredients were unstable in certain other waterless compositions.

In the waterless polar environments the concepts of pH, pK, and the like are artificial and may only give approximate guidance. It has been surprisingly found that in a non-classical waterless polar environment of foamable carriers, compositions and foam's that active ingredients can be susceptible to break down, isomerization, oxidisation or reaction in the presence of acid or basic residues, which in small quantities are able in a non classical way to take the active agent outside its preferred environmental window and facilitate instability. Likewise such breakdown etc. could be catalyzed by the presence of metal ions in the waterless polar environment. Following investigation it has been discovered that the introduction of an acid or base or buffer in a non classical non-aqueous polar environment of foamable carriers, compositions and foam's can act to prevent or impede such breakdown etc. Similarly, the introduction of a chelating agent can also act to prevent or impede catalyzation of such breakdown etc. Likewise, introduction of an anti ionization or antioxidation agent may also act to prevent or impede such reaction etc.

It has been surprisingly discovered that one can modulate the environment of a non-aqueous foamable, carrier, composition or foam to provide a stable environmental window for the active agent in the non-aqueous environment. The modifying or modulating affect of the modulating agent on the waterless environment prevents or minimizes a so-called 'change in the artificial pH range' and/or locks up available metal ions which could otherwise act as a catalyst in the waterless environment and/or impedes ionization or oxidation of the active agent.

Following investigation, modulating agents are identified, which by their presence are able to stabilize active pharmaceutical or cosmetic agents in a waterless or substantially waterless environment. More particularly, they can be effective at relatively low concentrations that have little or no significant effect on the foam compositions of the present invention.

According to one or more embodiments there is provided a waterless composition as a vehicle in which a modulating agent is incorporated and which is capable of stabilizing an active pharmaceutical or cosmetic agent, when added.

According to one or more embodiments there is provided a waterless vehicle, an active agent that is susceptible, to one or more of reaction, breakdown, ionization or oxidation and a modulating agent. In an embodiment the waterless vehicle comprises a hydrophobic solvent. In another embodiment it comprises a hydrophilic solvent.

According to one or more embodiments, the carrier, includes: a waterless solvent, a stabilizing surfactant, and or a polymeric agent, and in which is incorporated a modulating agent.

According to one or more embodiments, the carrier is a foamable carrier, and includes: a waterless solvent, a stabilizing surfactant, and or a polymeric agent, and a propellant and in which is incorporated a modulating agent.

According to one or more preferred embodiments, the carrier comprises a stabilizing agent comprising a surfactant and a polymeric agent. This is particularly helpful for foamable compositions where the combination can be synergistic or complimentary in providing a robust stable foam of quality with a reasonable collase time.

In an embodiment the carrier and modulating agent formulation is capable of stabilizing an active pharmaceutical or cosmetic agent in a substantially waterless environment.

According to one or more embodiments, pharmaceutical or cosmetic composition is foamable and, includes: a waterless solvent, a stabilizing surfactant, and or a polymeric agent, a modulating agent, a propellant and one or more active pharmaceutical or cosmetic agents.

According to one or more embodiments, the active agent itself can have characteristics of a modifying agent.

According to one or more embodiments, the carrier, includes:
 (a) a waterless solvent comprising about 25% to about 98% of at least polar solvent selected from the group consisting of (1) a polyol; and (2) a polyethylene glycol or combinations thereof;
 (b) a modulating agent;
 (c) a stabilizing agent selected from the group consisting of a surface-active agent and about 0.01% to about 5% by weight of at least one polymeric agent and mixtures thereof;
wherein the carrier is shakable or flowable and wherein if the composition is stored in an aerosol container and further comprises a liquefied or compressed gas propellant at a concentration of about 3% to about 25% by weight of the total composition it will upon release expand to form a breakable foam.

According to one or more embodiments the active agent is susceptible to reaction, breakdown, ionization, or oxidization.

According to one or more embodiments, the active agent itself can have characteristics of a modifying agent.

According to one or more embodiments, the foamable carrier, includes:
1. a waterless solvent comprising about 25% to about 98% of at least polar solvent selected from the group consisting of (1) a polyol; and (2) a polyethylene glycol or combinations thereof;
2. a modulating agent;
3. a stabilizing agent selected from the group consisting of a surface-active agent; and about 0.01% to about 5% by weight of at least one polymeric agent and mixtures thereof; and
4. a liquefied or compressed gas propellant at a concentration of about 3% to about 25% by weight of the total composition;

wherein the composition is shakable or flowable; and
wherein the composition is stored in an aerosol container and upon release expands to form a breakable foam.

According to one or more embodiments, the foamable pharmaceutical composition, includes:
1. a waterless solvent comprising about 25% to about 98% of at least polar solvent selected from the group consisting of (1) a polyol; and (2) a polyethylene glycol or combinations thereof;
2. a modulating agent;
3. a surface-active agent;
4. about 0.01% to about 5% by weight of at least one polymeric agent;
5. a liquefied or compressed gas propellant at a concentration of about 3% to about 25% by weight of the total composition; and
6. an effective amount of an active pharmaceutical or cosmetic agent;

wherein the carrier is shakable or flowable; and
wherein the composition is stored in an aerosol container and upon release expands to form a breakable foam.

The problem of producing a pharmaceutical composition that can provide a stable or stabilized environment or he more formidable problem a foamable composition which can produce a breakable foam of quality and a stabilized environment so that the active pharmaceutical agent does not substantially break down over a reasonable time period sufficient for normal pharmaceutical or cosmetic use is surprisingly resolved by having both a polymeric agent and modulating agent present in the foamable composition.

In one or more embodiments the polymeric agent is selected from a bioadhesive agent, a gelling agent, a film forming agent and a phase change agent and can be from about 0.01% to about 5% by weight, preferably 0.2 to 3%.

In one or more embodiments the ratio of polymeric agent to surfactant is about 1:10 to about 10:1; about 1:5 to about 5:1; about 3:7 to about 7:3; and about 2:1 to about 1:2.

The provision and selection of polymeric agent is however not straightforward. The polymers should be miscible or swell in the waterless solvent. It has been found that in the case of modified cellulose that lower molecular weight cellulose polymer derivatives are preferable.

In one or more preferred embodiments the polymeric agent is hydroxypropyl cellulose.

In another preferred embodiments the polymeric agent is or Carbomer such as Carbopol 934®.

According to one or more embodiments, the pre-foamable carrier; the pre-foamable pharmaceutical or cosmetic composition; the foamable carrier, or the foamable pharmaceutical or cosmetic composition further includes 0.1% to about 75% of a secondary polar solvent.

In one or more embodiments there is provided a vehicle additive, preferably a foamable vehicle additive that is suitable for use with not merely one type of active pharmaceutical ingredient ("API") but is adaptable for use with one or more API's from a wide range of different types of API's with appropriate and usually relatively minimal or minor adjustment. For example, by altering the amount of a component or by the addition or replacement of a buffer, stabilizer, anti ionization agent or an antioxidant as would be appreciated by a person skilled in the art with the benefit of the teachings herein. In one or more other embodiments there is provided one or more pharmaceutical or cosmetic base compositions that are suitable for use with modulating agents.

In one or more embodiments there is provided a vehicle additive, preferably a foamable one that is suitable for use as a vehicle base for delivery for API's, which are by their nature unstable or reactive or isomerizes or oxidize.

In a further embodiment the modulating agent is preferably between about 0.05% to about 5% by weight of the composition.

In a further embodiment the surfactant and polymeric agent and their amounts are selected so that the composition is sufficiently shakable or in certain limited cases so that it is flowable albeit not shakable so that extrusion and substantially uniform composition formation, particularly foam extrusion and formation is not hampered. To this extent, the maximum effective amount of surfactant and polymeric agent that may be used may be limited by the need for shakability and as a minimum by the need for flowability.

In a further embodiment of the present invention the propellant is preferably between about 5% to about 12% by weight of the composition.

In one or more embodiments of the pharmaceutical or cosmetic foamable product is non-flammable.

By waterless is meant that the composition contains no or substantially no, free or unassociated or absorbed water. It will be understood by a person of the art that the waterless solvents and substances miscible with them of the present invention can be hydrophilic and can contain water in an associated or unfree or absorbed form and may absorb water from the atmosphere and the ability to do so is its hygroscopic water capacity.

In one or more embodiments the carrier comprises an active pharmaceutical or cosmetic agent, which degrades in the presence of water, and in such cases the present of water in the composition is clearly not desirable. Thus, in certain preferred embodiments, the composition is waterless. In other embodiments the active agent may tolerate the presence of a small amount of water and the waterless composition is substantially non-aqueous. The term "substantially non-aqueous" is intended to indicate that the waterless composition has water content below about 5%, preferably below about 2%, such as below about 1.5%.

In one or more embodiments the active agent has low or minimal sensitivity and can tolerate water to about 10% or less.

Upon release from an aerosol container, the foamable carrier forms an expanded foam suitable for the treatment of an infected surface and for topical administration to the skin, a body surface, a body cavity or a mucosal surface.

Waterless Solvent

In one or more embodiments of the present invention the waterless solvent comprises about 25% to about 98% of at least a polar solvent selected from the group consisting of (1) a polyol; and (2) a polyethylene glycol or combinations thereof.

In one or more embodiments of the present invention the waterless solvent comprises about 0.1% to about 75% of a secondary polar solvent.

Polar Solvent

The identification of a "polar solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

Polyol

In an embodiment of the present invention, the polar solvent is a polyol. A polyol is an organic substance that contains at least two hydroxy groups in its molecular structure.

In one or more embodiments, the foamable carrier contains at least one diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the foamable carrier contains at least one triol (a compound that contains three hydroxy groups in its molecular structure), such as glycerin, butane-1,2,3-triol, butane-1,2,4-triol and hexane-1,2,6-triol.

In one or more embodiments, the polyol is a mixture of polyols. In one or more embodiments, the mixture of polyols contains at least one diol and at least one triol. According to certain embodiments the ratio between the diol and triol is between 9:1 and 1:1.

In one or more embodiments, part of mixture of polyols is a saccharide. Exemplary saccharides include, but are not limited to monosaccharide, disaccharides, oligosaccharides and sugar alcohols.

A monosaccharide is a simple sugar that cannot be hydrolyzed to smaller units. Empirical formula is $(CH_2O)_n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol). Mixtures of polyols, including (1) at least one polyol selected from a diol and a triol; and (2) a saccharide are contemplated within the scope of the present invention.

Polyethylene Glycol

In an embodiment of the present invention, the polar solvent consists of a polymerized ethylene glycol, namely polyethylene glycol, which is also termed "PEG". Exemplary PEGs are provided in the following table.

| Composition | Av. Molecular weight | Appearance | Melting point (° C.) |
|---|---|---|---|
| PEG 200 | 190~210 | Oily liquid | |
| PEG 300 | 285~315 | Oily liquid | |
| PEG 400 | 380~420 | Oily liquid | |
| PEG 600 | 570~630 | Oily liquid | 17~22 |
| PEG 1000 | 950~1050 | Solid | 35~40 |
| PEG 4000 | 3800~4400 | Solid | 53~58 |
| PEG 6000 | 5600~6400 | Solid | 55~60 |
| PEG 8000 | 7500~8500 | Solid | 58~65 |

Thus, in an embodiment of the present invention, the PEG is selected from the group consisting of PEG 200, PEG 300, PEG 400, PEG 600, PEG 1000, PEG 4000, PEG 6000 and PEG 8000. The foamable carrier according to the present invention can contain a single PEG or a mixture of two or more PEGs. PEGs having molecular weight of more that about 1000 possess gelling properties; i.e., they increase the viscosity of a composition. Therefore, by combining PEGs with different molecular weights/melting points, one can attain varying levels of flowability as desirable for the treatment of a given target site. The concentration of the PEG should be in a level that results in viscosity, prior to filling of the composition into aerosol canisters, of less than 12,000 CPs, and more preferably, less than 10,000 CPs.

Secondary Polar Solvent

Optionally, a secondary polar solvent is added to the foamable composition of the present invention. The secondary polar solvent is selected from a variety of organic solvents that are typically miscible on both water and oil. Examples of polar solvent that can be contained in the foamable carrier of the present invention include dimethyl isosorbide, tetrahydrofurfuryl alcohol polyethyleneglycol ether (glycofurol), DMSO, pyrrolidones, (such as N-Methyl-2-pyrrolidone and 1-Methyl-2-pyrrolidinone), ethyl proxitol, dimethylacetamide (DMAc), PEG-type surfactants and alpha hydroxy acids, such as lactic acid and glycolic acid.

Appropriate use of a secondary solvent in a waterless foam composition can help improve delivery of active agents to a target area. Foam compositions of the present invention, for which the solvent includes a secondary solvent, can increase the levels of the active agent in the waterless composition and thus, provide high delivery and improved therapy.

Solubilization and Penetration Enhancement

In many cases, polyols, PEGs and polar solvents possess a high solubilizing power and thus, they can enable increased concentrations of a pharmaceutical active agent. Polyols, PEGs and polar solvents are also known for their skin penetration enhancement properties. These properties enable high drug bioavailability in the target area of treatment, resulting in an enhanced therapeutic effect. Occasionally, combinations of a polyol, PEGs and a secondary polar solvent, exhibit an increased permeability across the skin, as suggested, for example, in Eur J Pharm Biopharm. 1998 November; 46(3):265-71.

Thus, in one or more embodiments, the foamable carrier contains (1) at least one polar solvent, selected from a polyol (selected from a diol and a triol) and PEG; and (2) at least one secondary polar solvent.

In one or more embodiments, the foamable carrier contains (1) a mixture of at least two polyols; and (2) at least one secondary polar solvent. In additional embodiments, the foamable carrier contains a mixture of at least one polyol and at least one PEG; yet in other embodiments the foamable carrier contains (1) a mixture of at least one polyol and at least one PEG and (2) at least one secondary polar solvent.

According to certain embodiments the ratio between the polyol and/or PEG and the secondary polar solvent is between 9:1 and 1:1.

In certain embodiments, the polyol is selected from the group consisting of propylene glycol, hexylene glycol and glycerin (and mixtures thereof); and the secondary polar solvent is selected from the group consisting of dimethyl isosorbide, diethylene glycol monoethyl ether, a liquid polyethylene glycol and glycofurol.

In certain embodiments, the foamable carrier contains (1) at least one polyol; and (2) dimethyl isosorbide.

Short chain alcohols, such as ethanol and propanol are known as polar solvents, however, according to one or more embodiments, the composition of the present invention is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable polar solvents due to their skin-irritating effect.

Thus, in certain embodiments, the composition is substantially alcohol-free and includes less than about 5% final concentration of lower alcohols, preferably less than about 2%, more preferably less than about 1%. However, in other embodiments, a short chain alcohol can be included in the composition, as long as the ratio between the short chain alcohol and the polyol is less than 1:4 by weight.

Modulating Agent

The term modulating agent is used to describe an agent which can improve the stability of or stabilize a carrier or a foamable composition and or an active agent by modulating the effect of a substance or residue present in the carrier or composition. The substance or residue may for example be acidic or basic and potentially alter an artificial pH in a waterless or substantially non aqueous environment or it may be one or more metal ions which may act as a potential catalyst in a waterless or substantially non aqueous environment or it may be an ionisation agent or it may be an oxidizing agent.

In one or more other embodiments the modulating agent is used in a waterless composition. In one or more embodiments the modulating agent is used in a substantially non aqueous composition In one or more embodiments the modulating agent is used to describe an agent which can affect pH in an aqueous solution.

The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the waterless solvent to enable it to "mop up" or "lock" metal ions.

In the embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of a waterless or substantially non aqueous carrier, composition, foamable carrier or foamable composition or resultant foam of the present invention.

The substance or residue can be introduced into the formulation from any one or more of the ingredients, some of which themselves may have acidic or basic properties. For example the polymer or solvent may contain basic residues in which case it may be desirable or beneficial to add an acid. Alternatively the surfactant may contain some acid residues in which case the addition of a base may be desirable and beneficial. In some cases more than one ingredient may contain residues which may ameliorate or compound their significance. For example if one ingredient provided weak acid residues and another stronger acid residues the artificial pH in a waterless environment should be lower. In contrast, if one residue was acid and the other basic the net effect in the formulation maybe significantly reduced. In some circumstances the active ingredient may favor an acidic pH or more significantly may need to be maintained at a certain acidic pH otherwise it may readily isomerize, chemically react or breakdown, in which case introducing acidic components might be of help. Likewise in some circumstances the active ingredient may favor a basic pH or more significantly may need to be maintained at a certain basic pH otherwise it may readily hydrolyse, undergo rearrangement, isomerize, chemically react or breakdown, in which case introducing basic components might be of help. In an embodiment of the present invention sufficient modulating agent is added to achieve an artificial pH in which the active agent is preferably stable. Such artificial pH may be acidic, maybe basic or may be neutral.

The terms pH, pKa, and pKb, buffers and the like are used in classical measurements of an aqueous solution. Such measurements are artificial in a waterless environment. Nevertheless, reference to and description below of such terms are made for convenience and clarity, since such terms are well defined and understood with reference to aqueous solutions and further due to the lack of an appropriate uniform way of describing and identifying the artificial or virtual pH, pK etc in a waterless environment in relation to the present invention. Although predictions of artificial pH can be made using dilution techniques of measurements of waterless formulations diluted in water they are formulation sensitive and specific and have to be carefully calibrated with complex formulas.

Waterless medium can be polar and protic yet it does not conform to classical ionic behavior.

A buffer, as defined by Van Slyke [Van Slyke, J. Biol. Chem. 52, 525 (1922)], is "a substance which by its presence in solution increases the amount of acid or alkali that must be added to cause unit change in pH".

A buffer solution is a solution of a definite pH made up in such a way that this pH alters only gradually with the addition of alkali or acid. Such a solution consists of a solution of a salt of the week acid in the presence of the three acid itself. The pH of the solution is determined by the dissociation equilibrium of the free acid.

An acid can be a strong acid or a weak acid. A strong acid is an acid, which is a virtually 100% ionized in solution. In contrast, a week acid is one which does not ionize fully when it is dissolved in water. The lower the value for pKa, the stronger is the acid and likewise, the higher the value for pKa the weaker is the acid.

A base can be a strong base or a weak base. A strong base is something, which is fully ionic with 100% hydroxide ions. In contrast, a weak base is one which does not convert fully into hydroxide ions in solution. The lower the value for pKb, the stronger is the base and likewise, the higher the value for pKb the weaker is the base.

In general terms, three factors, which influence the strength of a base, are firstly the ease with which the lone pair takes up a hydrogen ion; secondly, the stability of ions being formed and thirdly, the way they interact with water such that if they pick up hydrogen ion's more readily it is a stronger base.

An acid in an amount to affect the composition's pH selected from the group consisting of:

(a) An alpha hydroxyl acid of formula I:

    I or a pharmaceutically acceptable salt, lactone, or solvate thereof, wherein $R_a$ and $R_b$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group;

(b) An aliphatic beta hydroxyacid of formula II:

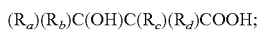
    II or a pharmaceutically acceptable salt, lactone, or solvate thereof, wherein $R_a$, $R_b$, $R_c$ and $R_d$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups, wherein each of $R_a$ and $R_b$ may be optionally substituted with an OH, SH, CHO, COOH group.

Exemplary alpha hydroxyl acids and beta hydroxyl acids include, but are not limited to alpha-hydroxybutyric acid, alpha-hydroxyisobutyric acid, alpha-hydroxyisocaproic acid, alpha-hydroxyisovaleric acid, atrolactic acid, beta-hydroxybutyric acid, beta-phenyl lactic acid, beta-phenylpyruvic acid, citric acid, pyruvic acid, galacturonic acid, glucoheptonic acid, glucoheptono 1,4-lactone, gluconic acid, gluconolactone, glucuronic acid, glucuronolactone, glycolic acid, lactic acid, mandelic acid, mucic acid, pyruvic acid, saccharic acid, saccharic acid 1,4-lactone, tartaric acid and tartronic acid, 3-Hydroxybutanoic acid, quinic acid, isocitric acid, tropic acid, trethocanic acid, chlorolactic acid, citramalic acid, agaricic acid, aleuritic acid, pantoic acid, lactobionic acid, piscidic acid, hexylosonic acid or the anhydride thereof.

(c) An aromatic acid.

Exemplary aromatic acids include, but are not limited to benzoic acid, toluic acid, dimethyl benzoic acid, phthalic acid and nicotinic acid (heterocyclic).

(d) an aromatic hydroxyl acid of formula IIIa, IIIb and IIIc:

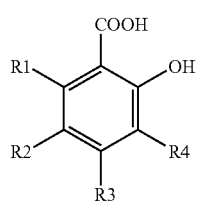
    IIIa

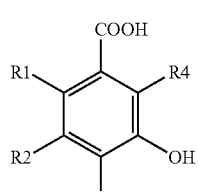
    IIIb

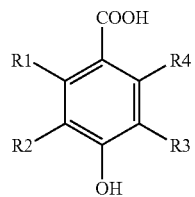
    IIIc

The aromatic ring can contain solely carbon atoms or a combination of carbon atoms and other atoms (heterocyclic), wherein $R_1$, $R_2$, $R_3$ and $R_4$ are independently selected from the group consisting of H, F, Cl, Br, and saturated or unsaturated, isomeric or non-isomeric, straight, branched, or cyclic $C_1$-$C_{25}$ alkyl, aralkyl, or aryl groups.

Formula IIIa, wherein R is H, is identified as salicylic acid, yet another example of an aromatic hydroxyl acid is acetylsalicylic acid.

(e) an alpha ketoacid of formula IV:

    IV or a pharmaceutically acceptable salt, ester, or solvate thereof, wherein $R_a$ and $R_b$ are independently selected from the group consisting of H and saturated or unsaturated, isomeric or non-isomeric, straight, branched, or cyclic $C_1$-$C_{25}$ alkyl, aralkyl, or aryl groups, wherein $R_a$ may be optionally substituted with an F, Cl, Br, I, OH, CHO, COOH, or alkoxy group having 1 to 9 carbon atoms;

(f) An aliphatic carboxylic acid.

Short chain carboxylic acids include formic acid, acetic acid and propionic acid.

A fatty acid is a carboxylic acid often with a long unbranched aliphatic tail (chain), which is either saturated or unsaturated. Carboxylic acids as short as butyric acid (4 carbon atoms) are considered to be fatty acids, while fatty acids derived from natural fats and oils may be assumed to have at least 8 carbon atoms, as exemplified in the following list:

Butyric (butanoic acid): $CH_3(CH_2)_2COOH$
Caproic (hexanoic acid): $CH_3(CH_2)_4COOH$
Caprylic (octanoic acid): $CH_3(CH_2)_6COOH$
Nonanoic acid: $CH_3(CH_2)_7COOH$
Capric (decanoic acid): $CH_3(CH_2)_8COOH$
Lauric (dodecanoic acid): $CH_3(CH_2)_{10}COOH$
Myristic (tetradecanoic acid): $CH_3(CH_2)_{12}COOH$
Palmitic (hexadecanoic acid): $CH_3(CH_2)_{14}COOH$
Stearic (octadecanoic acid): $CH_3(CH_2)_{16}COOH$
Arachidic (eicosanoic acid): $CH_3(CH_2)_{18}COOH$
Behenic (docosanoic acid): $CH_3(CH_2)_{20}COOH$
Octacosanoic: $CH_3(CH_2)_{26}COOH$ Optionally, the carbon atom chain of the fatty acid may have at least one double bond, as exemplifies in the following list:

Oleic acid: $CH_3(CH_2)_7CH=CH(CH_2)_7COOH$
Linoleic acid: $CH_3(CH_2)_4-CH=CHCH_2CH=CH(CH_2)_7COOH$
Alpha-linolenic acid: $CH_3CH_2CH=CHCH_2CH=CHCH_2CH=CH(CH_2)_7COOH$
Arachidonic acid $CH_3(CH_2)_4-CH=CHCH_2CH=CHCH_2CH=CHCH_2CH=CH(CH_2)_3COOH$
Eicosapentaenoic acid
Docosahexaenoic acid
Erucic acid: $CH_3(CH_2)7CH=CH(CH2)11COOH$ Alpha-linolenic, docosahexaenoic, and eicosapentaenoic acids are examples of omega-3 fatty acids. Linoleic acid and arachidonic acid are omega-6 fatty acids. Oleic and erucic acid are omega-9 fatty acids.

A further class of carboxylic acids according to the present invention comprises a carboxylic acid, wherein the carbon atom chain is branched, such as valproic acid. The carbon chain of the fatty acid or fatty alcohol can be substituted with a hydroxyl group, such as 12-hydroxy stearic acid.

Short chain carboxylic acids such as formic acid and acetic acid are reasonably strong acids (pKa 3.77 and 4.76, respectively). Longer chain fatty acids have higher pKa values. Nonanoic acid, for example, has a pKa of 4.96.

(g) a dicarboxylic acid

In the context of the present invention, a dicarboxylic acid is an organic compound, having two carboxylic acid moieties on its carbon atom skeleton. They have the general molecular formula HOOC—$(CH_2)_n$—COOH.

In an embodiment of the present invention, the dicarboxylic acid is a short-chain dicarboxylic acid. The simplest short-chain dicarboxylic acid are oxalic acid (n=0), malonic acid (n=1), succinic acid (n=2) and glutaric acid (n=3).

Additional members of dicarboxylic acid group are derived from natural products or from synthesis, having "n" value from 4 up to 21. In one or more embodiments of the present invention, the dicarboxylic acid is selected from the group consisting of adipic acid (hexanedioic acid; n=4), pimelic acid (heptanedioic acid; n=5), suberic acid (octanedioic acid; n=6), azelaic acid (nonanedioic acid; n=7), sebacic acid (decanedioic acid; n=8) and dodecanedioic acid (n=10).

In an additional embodiment, the dicarboxylic acid contains 10 to 32 carbon atoms in their carbon atom skeleton, such as brassylic acid (n=11), thapsic acid (n=14), 14-methylnonacosanedioic acid (C29) and 14,15-dimethyltriacontanedioic acid (C30).

The carbon atom skeleton of the dicarboxylic acid can be saturated or unsaturated, such as in the case of undecylenic acid, maleic acid and fumaric acid.

In an additional embodiment, the dicarboxylic acid is branched, i.e., the carbon atom skeleton of the dicarboxylic acid can be substituted with at least one group selected from the group consisting of R, F, Cl, Br, OH, OR, SH, CHO, COOH, and $NR_aR_b$, wherein R, $R_a$ and $R_b$ are independently selected from the group consisting of H, saturated or unsaturated, isomeric or non-isomeric, straight, branched, or cyclic $C_1$-$C_{25}$ alkyl, aralkyl, or aryl groups. Exemplary branched dicarboxylic acids include aspartic acid, alpha-ketoglutaric acid, adipic acid 2-amino, aconitic acid, benzene dicarboxylic acid, citramalic acid, citric acid, cystathionine, glucuronic acid, glutamic acid, itaconic acid, malic acid, mucic acid, oxalacetic acid, diamino pimelic acid, saccharic acid, dimethyl succinic acid, tartaric acid, tartronic acid, (h) Miscellaneous organic acids In an embodiment of the present invention, the organic acid is selected from the group consisting of ascorbic acid, isoascorbic acid, ethanesulfonic acid, glycerophosphoric acid, acetohydroxamic acid, aconitic acid, alpha-ketocaproic acid, aminomalonic acid, hippuric acid, hydrochloric acid, methanesulfonic acid, oxalic acid, phosphoric acid, sorbic acid, iminodiacetic acid, carnitine, nicotinic acid and retinoids, such as retinoic acid and isotretinoin.

(i) Amino acid

The a-COOH and a-$NH_2$ groups in amino acids are capable of ionizing (as are the acidic and basic R-groups of the amino acids). As a result of their ionizability the following ionic equilibrium reactions may be written:

The equilibrium reactions, as written, demonstrate that amino acids contain at least two weakly acidic groups. However, typically the carboxyl group is a far stronger acid than the amino group. At physiological pH (around 7.4) the carboxyl group will be unprotonated and the amino group will be protonated. An amino acid with no ionizable R-group would be electrically neutral at this pH. This species is termed a zwitterion.

Like typical organic acids, the acidic strength of the carboxyl, amino and ionizable R-groups in amino acids can be defined by the association constant, Ka or more commonly the negative logarithm of Ka, the pKa. The net charge (the algebraic sum of all the charged groups present) of any amino acid, peptide or protein, will depend upon the pH of the surrounding aqueous environment. As the pH of a solution of an amino acid or protein changes so too does the net charge. This phenomenon can be observed during the titration of any amino acid or protein. When the net charge of an amino acid or protein is zero the pH will be equivalent to the isoelectric point: pI.

The following table lists amino acids and their pKa's:

| Acid | $pK_1$ (COOH) | $pK_2$ ($NH_2$) | pK R Group |
|---|---|---|---|
| Glycine | 2.4 | 9.8 | |
| Alanine | 2.4 | 9.9 | |
| Valine | 2.2 | 9.7 | |
| Leucine | 2.3 | 9.7 | |
| Isoleucine | 2.3 | 9.8 | |
| Serine | 2.2 | 9.2 | ~13 |
| Threonine | 2.1 | 9.1 | ~13 |
| Cysteine | 1.9 | 10.8 | 8.3 |
| Methionine | 2.1 | 9.3 | |
| Aspartic Acid | 2.0 | 9.9 | 3.9 |
| Asparagine | 2.1 | 8.8 | |
| Glutamic Acid | 2.1 | 9.5 | 4.1 |
| Glutamine | 2.2 | 9.1 | |
| Arginine | 1.8 | 9.0 | 12.5 |
| Lysine | 2.2 | 9.2 | 10.8 |
| Histidine | 1.8 | 9.2 | 6.0 |
| Phenylalanine | 2.2 | 9.2 | |
| Tyrosine | 2.2 | 9.1 | 10.1 |
| Tryptophan | 2.4 | 9.4 | |
| Proline | 2.0 | 10.6 | |

In addition, nonprotein amino acids are also suitable in accordance to the present invention, including but not limited to: B-alanine (3-alanine), 4-aminobutyrate (GABA), 3-cyanoalanine (B-cyanoalanine), 2-aminobutyric acid, 2-methylene-4-aminobutyric acid, 3-methylene-4-aminobutyric acid, 2-aminoisobutyric acid, 5-aminolevulinic acid, 2-amino-4-methylhexanoic acid (homoisoleucine), 2-amino-4-methylhex-4-enoic acid, 2-amino-4-methylhex-5-ynoic acid, 2-amino-3-methylpentanoic acid, 2-aminoadipic acid, 4-ethylideneglutamic acid, 3-aminoglutaric acid, 2-aminopimelic acid, N4-ethylasparagine, N4-methylasparagine, erythro-4-methylglutamic acid, 4-methyleneglutamic acid, 4-methyleneglutamine, N5-methylglutamine, N5-ethylglutamine (theanine), N5-isopropylglutamine, 2-amino-4-(aminoxy)butyric acid (canaline), 2,4-diaminobutyrate, N4-acetyl-2,4-diaminobutyrate, N4-lactyl-2,4-diaminobutyrate, N4-oxalyl-2,4-diaminobutyrate, 2,3-diaminopropionic acid, N3-acetyl-2,3-diaminopropionic acid, N3-methyl-2,3-diaminopropionic acid, N3-oxalyl-2,3-diaminopropionic acid, N6-acetyllysine, N6-methyllysine, N6-trimethyllysine (laminine), ornithine (2,5-diaminopentanoic acid), saccharopine (N-6-(2'-glutamyl)lysine, 2,6-diaminopimelic acid, N4-(2-hydroxylethyl)asparagine, erythro-3-hydroxyaspartic acid, 4-hydroxyarginine, 4-hydroxycitrulline, threo-4-hydroxyglutamic acid, 3,4-dihydroxyglutamic acid, 3-hydroxy-4-methylglutamic acid, 3-hydroxy-4-methyleneglutamic acid, 4-hydroxy-4-methylglutamic acid, 4-hydroxyglutamine, N5-(2-hydroxyethyl)glutamine, 5-hydroxynorleucine, threo-4-hydroxyhomoarginine, homoserine, O-acetylhomoserine, O-oxalylhomoserine, O-phosphohomoserine, 4-hydroxyisoleucine, 5-hydroxymethylhomocysteine, threo-3-hydroxyleucine, 5-hydroxyleucine, 2-hydroxylysine, 4-hydroxylysine, 5-hydroxylysine, N6-acetyl-5-hydroxylysine, N6-trimethyl-5-hydroxylysine, 4-hydroxyornithine, mimosine, 4-hydroxynorvaline, 5-hydroxynorvaline, 2-amino-4,5-dihydroxypentanoic acid, 2-amino-4-hydroxypimelic acid, 4-hydroxyvaline, O-acetylserine, O-phosphoserine, pipecolic acid, (piperidine-2-carboxylic acid), 3-hydroxypipecolic acid, trans-4-hydroxypipecolic acid, trans-5-hydroxypipecolic acid, 5-hydroxy-6-methylpipecolic acid, 4,5-dihydroxypipecolic acid, trans-3-hydroxyproline, trans-4-hydroxyproline, trans-4-hydroxymethylproline, azetidine-2-carboxylic acid, N-(3-amino-3-carboxypropyl)azetidine-2-carboxylic acid, 4,5-dehydropipecolic acid (baikiain), 3-amino-3-carboxypyrrolidone (cucurbitine), 2-(cyclopent-2'-enyl) glycine, 5-hydroxytryptophan, albizziine (2-amino-3-ureidopropionic acid), arginosuccinic acid, canavinosuccinic acid, citrulline, homoarginine, homocitrulline, indospicine, O-ureidohomoserine, 6-hydroxykynurenine, 3-(4-aminophenyl)alanine, 3-(3-aminomethylphenyl)alanine, 3-(3-carboxyphenyl)alanine, 3-carboxytyrosine, 3-(3-hydroxymethylphenyl)alanine, 3-(3-hydroxyphenyl)alanine, 3-(3,4-dihydroxyphenyl)alanine (L-DOPA), 2-(phenyl)glycine, 2-(3-carboxyphenyl)glycine, 2-(3-carboxy-4-hydroxyphenyl)glycine, 2-(3-hydroxyphenyl)glycine, 2-(3,5-dihydroxyphenyl)glycine, 4-aminopipecolic acid, guvacine, 2-amino-4-(isoxazolin-5-one)-2-yl)butyric acid, lathyrine, tetrahydrolathyrine and ornithin.

In an embodiment of the present invention the organic modulating agent is a dimer or oligomer of amino acids.

In an embodiment of the present invention the organic modulating agent is an organic base.

In an embodiment the organic base is a nitrogen-containing organic compound.

In an embodiment the nitrogen-containing organic modulating compound is selected from, primary, secondary, tertiary and quaternary amines. The organic primary amine may include alkylamines such as methylamine and ethylamine; ethanolamine such as monoethanolamine and monoisopropanolamines; diamines such as ethylenediamine and 1,2-diaminopropane. The organic secondary amines include dialkylamines such as dimethylamine and diethylamine, diethanolamine and diisopropanolamine; N-methylethanolamine and N-ethylethanolamine. The organic tertiary amines include trialkylamines such as triethylamine and triethylamine; triethanolamine; N-methyldiethanolamine and triisopropanolamine. The quaternary compounds preferably include basic choline.

In an embodiment the nitrogen-containing organic modulating compound is an amide. Amides are derivatives of oxoacids in which an acidic hydroxy group has been replaced by an amino or substituted amino group. Compounds having one, two, or threeacyl groups on a given nitrogen are generically included and may be designated as primary, secondary and tertiary amides, respectively.

In an embodiment the nitrogen-containing organic modulating compound is an amine oxide. amine oxide are compounds derived from tertiary amines by the attachment of one oxygen atom to the nitrogen atom: $R_3N^+—O^-$.

In an embodiment the nitrogen-containing organic modulating compound is a lactam. Lactams are cyclic amides amino carboxylic acids, having a 1-azacycloalkan-2-one structure, or analogues having unsaturation or heteroatoms replacing one or more carbon atoms of the ring, as exemplified in the following structures:

 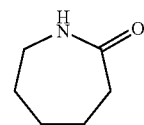

Urea is another example of a nitrogen-containing modulating compound.

The modulating agent to the foamable composition of the present invention is useful for stabilizing pharmaceutical and cosmetic active agents which are unstable in certain pH conditions. It is known, for example, that active agents, which contain ester bond in their structure tend to undergo hydrolysis of the ester bond at basic pH levels. Therefore, the addition of an agent which avoids the formation of basic pH condition and thus, prevents degradation of such active agents. Many steroid compounds are known to undergo rearrangement at high pH, and again, adding an acidic modulating agent helps prevent such degradation. This is clearly exemplified by the stark difference in stability results for BMV in the absence and presence of a modulating agent as demonstrated in Examples 1 and 2 below. Another example of a pH-sensitive active agent is vitamin D, which degrades at low pH levels. In such a case, the addition of a basic modulating agent, such as triethanol amine is useful to maintain acceptable stability of this active agents as can be seen an exemplified in Example 5 below.

In certain cases, the stability of an active agent may be influenced by small quantities of, for example, metal ions in the waterless compositions. Such metal ions may act as a catalyst in facilitating the reaction or breakdown of the agent. Thus the modulating agent can be a chelating or sequestering or complexing agent on its own. In one or more embodiments of the present invention there is provided an effective amount of chelating agent which is sufficiently soluble or functional in the waterless solvent to enable it to “mop up” or “lock” metal ions.

For instance it is known that Polyphenols through the chelation of transition-metal ions, particularly those of iron and copper inhibit free radical formation and the propagation of free radical reactions (Brown et al. in Biochem. J. 330, 1173 1178 (1998)). Citric acid, amino acids, and thylenediaminetetraacetic acid also form chelates with metallic ions such as copper and iron, thus avoiding their catalytic action on the oxidation of lipids. Most of these chelating agents exhibit little or no antioxidant activity when used alone, and therefore they are considered as synergistic agents of other antioxidants. Thus, they increase, to a great extent, the action of primary antioxidants.

In one or more embodiments of the present invention the chelating agent is selected from the group consisting of acetyl trihexyl citrate, aminotrimethylene phosphonic acid, beta-alanine diacetic acid, bismuth citrate, calcium disodium edta, citric acid, cyclohexanediamine tetraacetic acid, diammonium citrate, dibutyl oxalate, diethyl oxalate, diisobutyl oxalate, diisopropyl oxalate, dilithium oxalate, dimethyl oxalate, dipotassium edta, dipotassium oxalate, dipropyl oxalate, disodium edta, disodium edta-copper, disodium pyrophosphate, edta, etidronic acid, hedta, methyl cyclodextrin, oxalic acid, pentapotassium, triphosphate, pentasodium aminotrimethylene phosphonate, pentasodium pentetate, pentasodium triphosphate, pentetic acid, phytic acid, potassium citrate, sodium citrate, sodium dihydroxyethylglycinate, sodium gluceptate, sodium gluconate, sodium hexametaphosphate, sodium metaphosphate, sodium metasilicate, sodium oxalate, sodium trimetaphosphate, tea-edta, tetrahydroxypropyl ethylenediamine, tetrapotassium etidronate, tetrapotassium pyrophosphate, tetrasodium edta, tetrasodium etidronate, tetrasodium pyrophosphate, tripotassium edta, trisodium edta, trisodium hedta, trisodium nta, trisodium phosphate, malic acid, fumaric acid, maltol, succimer, penicillamine, dimercaprol, and desferrioxamine mesilate.]

Other authorized chelating agents are listed pursuant to annex 1, paragraph E.3.1 of regulation (EC) No 2003 (See Directive 67/548/EEC OJ 196, 16.8 1967, p 1) and are also incorporated herein by reference.

In one or more preferred embodiments of the present invention the chelating agent is selected from the group consisting of ethylenediaminetetraacetic acid ("EDTA") and salts thereof such as disodium EDTA, tetrasodium EDTA and calsium disodium EDTA; diethylenetriaminepentaacetic acid ("DTPA") and salts thereof; hydroxyethlethylenediaminetriacetic acid ("HEDTA") and salts thereof and nitrilotriacetic acid ("NTA"); more preferably EDTA, HEDTA and their salts; most preferably EDTA and its salts.

In one or more embodiments of the present invention a preferred non limiting example of the chelating agent is EDTA. Typically, the chelating and sequestering agent is present in the composition at a level of up to about 5.0%, preferably 1.0 percent, by weight, of the composition.

Combinations of Modulating Agents may be a useful aspect of the present invention. For example, as will be appreciated by a man of the art combinations of a strong acid and a weak base; a weak acid and a strong base: a weak acid and a strong acid; a weak base and a strong base; a weak base and a second weak base; and a weak acid and a second weak acid; may prove more effective in protecting or stabilizing an active agent in the waterless solvents of the present invention than a base or acid on its own. It will be understood that each of the active agents may have an artificial pH at which it can be more stable in a waterless composition. For example, ascorbic acid in aqueous solution is known to be more stable at an acidic pH of about 5.4. It is therefore desirable to add a combination of modulating agents in a waterless composition that will generate an artificial pH approximately of the order of or equivalent to that at which ascorbic acid is more stable in a waterless medium. In order to do so it will be appreciated a man of the art that that some adjustment will have to be made as ascorbic acid is itself a strong acid and displays the characteristics of a modulating agent. Similarly chelating agents may be usefully used in combination with another modulating agent such as an acid, a base or a buffer system or with various combinations of modulating agents.

The modulating agent to the foamable composition of the present invention is further useful for adjusting the pH of the target area of application. Skin is the first line of defense against all elements, such as microorganisms, wind, and pollutants, and it's the acid mantle, a fine film with a slightly acidic pH on the surface of the skin that provides protection for the skin. It plays a very important role as an integral part of the barrier function of the stratum corneum. Recent studies have demonstrated that increased enzyme activity of phospholipase A2 is related to the formation of the acid mantle in the stratum corneum. This combination makes the skin less permeable to water and other polar compounds. Normal skin surface pH is between 4 and 6.5 in healthy people, though it varies among the different areas of the skin. Newborn infants do have a higher skin surface pH compared to adults, but this normalizes within three days. Therefore, it is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since the best protection against vaginal infection is attained in pH lower than 4.

While the organic modulating agent can serve to stabilize an active agent in the foam composition, it often provides additional therapeutic properties to the composition. The following table exemplifies, in a non-limiting fashion, the therapeutic benefits expected from an organic modulating agent. It is to be understood that this table provides a non-exhaustive list of modulating agents that possess therapeutic effects, however, many other compounds listed in the present specification also possess therapeutic benefits.

| Class | Examples | Exemplary therapeutic properties |
| --- | --- | --- |
| Alpha hydroxy acids | Lactic acid | Humectant |
|  | Glycolic acid | Keratnocyte growth modifier Anti-psoriasis Anti acne |
| Beta hydroxyl acid | Salicylic acid | Keratolytic Antiinflammatory |
| Short chain carboxylic acid | Propionic acid Butyric acid | Antiinfective |
| Fatty acids | Nonanoic acid Behenic acid | Hair growth stimulant Antiinflammatory Antiinfective Humectant Skin protection |
| Unsaturated fatty acids | Omega-3 fatty acids Omega-6 fatty acids | Radical scavenger Anti-oxidant |
| Aromatic acids | Benzoic acid Phthalic acid Nicotinic acid | Antiinflammatory Anti-acne Anti-pigmentation Antiinfective Insect repellant |
| Dicarboxylic acids | Malonic acid, succinic acid, glutaric acid, adipic acid, pimelic acid, suberic acid, azelaic acid, sebacic acid | Antiinflammatory Keratolytic Anti-acne Anti-rosacea Anti-pigmentation |
| Amino acids |  | Keratnocyte growth modifier Hair growth stimulant Sebum control |
| Retinoids | Retinoic acid Isotretinoin | Antiinflammatory Keratolytic Anti-acne Anti-rosacea Anti-pigmentation |
| Nitrogen containing | Urea | Humectant Keratolytic Anti-psiriasis |

In one or more embodiments, the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

In one or more embodiments the modulating agent is a flavonoid.

Flavonoids (or bioflavonoids) are a large group of polyphenolic antioxidant compounds, which often occur as glycosides and are ubiquitously present in foods of plant origin. Some flavonoids (e.g. quercetin, rutin) are available as dietary supplements. Flavonoids can be further subdivided into:
flavonols (e.g. kaempferol, quercetin and myricetin)
flavones (e.g. apigenin and luteolin)
flavonones (e.g. hesperetin, naringenin, eriodictyol)
flavan-3-ols (e.g. (+)-catechin, (+)-gallocatechin, (−)-epicatechin, (−)-epigallocatechin)
anthocyanins (e.g. cyanidin, delphinidin, malvidin, pelargonidin, peonidin, petunidin)
proanthocyanidins.

More than 4000 flavonoids have been identified, and many have been studied. Most are colorless but some are responsible for the bright colors of many fruit and vegetables. Flavonoids are distinguished from the carotenoids.
Flavonoids appear to
act as scavengers of free radicals, including superoxide anions, singlet oxygen, and lipid peroxyl radicals (they have antioxidant properties);
sequester metal ions;
inhibit in vitro oxidation of LDL cholesterol;
inhibit cyclo-oxygenase, leading to lower platelet aggregation, decreased thrombotic tendency and reduced anti-inflammatory activity;
inhibit histamine release;
improve capillary function by reducing fragility of capillary walls and thus preventing abnormal leakage; and inhibit various stages of tumor development (animal studies only).

The activities of flavonoids are dependent on their chemical structure. Estimates of dietary flavonoid intake vary from 10 to 100 mg daily, but may be several hundreds of milligrams a day. Dietary supplements of quercetin and rutin provide around 500 mg in a single dose.

Flavonoids may have a potential role in the prevention of CVD, cancer and cataracts and possibly other diseases, for anti-viral activity, and they may be useful in treating ulcers. include hemorrhoids, allergy, asthma, menopausal symptoms and the prevention of habitual abortion.
Quercetin As a dietary supplement, quercetin is promoted for prevention and treatment of atherosclerosis and hyperlipidaemia, diabetes, cataracts, hay fever, peptic ulcer, inflammation, prevention of cancer and for treating prostatitis. A preliminary, double-blind, placebo-controlled trial in chronic non-bacterial prostatitis showed that quercetin reduced pain and improved quality of life, but had no effect on voiding dysfunction.
Rutin As a dietary supplement, rutin is used to reduce capillary permeability and treat symptoms of varicose veins. In combination with bromelain and trypsin, rutin is used to treat osteoarthritis.

A non limiting list of flavonoid compounds is: benzquercin, diosmin, ethoxazorutoside, flavodate, sodium hesperidin, leucocianido, monoxerutin, oxerutin, quercetin, rutoside, rosmarinic acid. The above information was noted from Dietary Supplements, Electronic Version, Pharmaceutical Press 2007.

In an embodiment a single flavonoid is provided and in a further embodiment a combination of two or more flavonoid are provided. In certain embodiments the flavonoids act synergistically. In an embodiment water soluble flavonoids are combined with water insoluble flavonoids. It is known for example that whole polyphenolic extracts have greater antioxidant effect than their known individual components. In an embodiment flavonoids are used in combination with other phenolics. In an embodiment one or more flavonoids are provided in combination with one or more vitamins. In an embodiment flavonoids are provided that are more reactive than the vitamins. In an embodiment the flavonoids act as a conservational agent.
Microsponges The Microsponges are rigid, porous and spongelike round microscopic particles of cross-linked polymer beads (e.g., polystyrene or copolymers thereof), each defining a substantially noncollapsible pore network. The Microsponges can be loaded with an active ingredient and can provide a controlled time release of the active ingredient to skin or to a mucosal membrane upon application of the formulation. The slow release is intended to reduce irritation by the active. Microsponge® delivery technology was developed by Advanced Polymer Systems. In one or more embodiments the composition comprises one or more active agents loaded into Microponges with a waterless carrier comprising a modulating agent.
Polymeric Agent The composition of the present invention contains a polymeric agent. It has been documented that the presence of a polymeric agent is necessary for the creation of foam, having fine bubble structure, which does not readily collapse upon release from the pressurized aerosol can. The polymeric agent serves to stabilize the foam composition and to control drug residence in the target organ. Preferably, the polymeric agent is soluble or readily dispersible in the polyol; or in the mixture of a polyol and an additional polar solvent.

Non-limiting examples of polymeric agents that are soluble or readily dispersible in propylene glycol are Hydroxypropylcellulose and carbomer (homopolymer of acrylic acid is crosslinked with an allyl ether pentaerythritol, an allyl ether of sucrose, or an allyl ether of propylene, such as Carbopol® 934, Carbopol® 940, Carbopo® 941, Carbopol® 980 and Carbopol® 981.

Other polymeric agents are suitable for use according to the present invention provided that they are soluble or readily dispersible in the polyol; or in the mixture of a polyol and an additional polar solvent, on a case by case basis.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as, hydroxypropyl cellulose, Polyethylene glycol, having molecular weight of 1000 or more (e.g., PEG 1,000, PEG 4,000, PEG 6,000 and PEG 10,000) also have gelling capacity and while they are considered herein as "secondary polar solvents", as detailed herein, they are also considered polymeric agents.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 12,000 CPs, and more preferably, less than 10,000 CPs.

Surface-Active Agent

The composition further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants can be significant in producing breakable forms of good quality. It has been further discovered that the generally thought considerations for HLB values for selecting a surfactant or surfactant combination are not always binding for emulsions and moreover for waterless and substantially non aqueous carriers the usual guidelines are less applicable. Surfactants also play a significant role in foam formation where the foamable formulation is a single phase composition.

According to one or more embodiments the composition contains a single surface active agent having an HLB value between about 2 and 9, or more than one surface active agent and the weighted average of their HLB values is between about 2 and about 9.

According to one or more embodiments the composition contains a single surface active agent having an HLB value between about 7 and 14, or more than one surface active agent and the weighted average of their HLB values is between about 7 and about 14.

According to one or more other embodiments the composition contains a single surface active agent having an HLB value between about 9 and about 19, or more than one surface active agent and the weighted average of their HLB values is between about 9 and about 19.

In a waterless or substantially waterless environment a wide range of HLB values may be suitable.

Preferably, the composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, a monoglyceride, a diglyceride, isoceteth-20 and mono-, di- and tri-esters of sucrose with fatty acids. In certain embodiments, suitable sucrose esters include those having high monoester content, which have higher HLB values.

In an embodiment the surfactant is an ether for example polyoxyethylene (26) glycerol ether.

In certain embodiments, surfactants are selected which can provide a close packed surfactant layer. To achieve such objectives combinations of at least two surfactants are selected. Preferably, they should be complex emulgators and more preferably they should both be of a similar molecular type; for example, a pair of ethers, like steareth 2 and steareth 21, or a pair of esters, for example, PEG-40 stearate and polysorbate 80. Ideally, the surfactants can be ethers. In certain circumstances POE esters cannot be used and a combination of sorbitan laurate and sorbitan stearate or a combination of sucrose stearic acid ester mixtures and sodium laurate may be used. All these combinations due to their versatility and strength may also be used satisfactorily and effectively with ether formulations, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenylsuccinate (ASOS)]/[DRY-FLO AF Starch], and derivatized dexrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB-4.9); glyceryl monostearate/PEG 100 stearate (Av HLB~11.2); stearate Laureth 4 (HLB-9.7) and cetomacrogol ether (e.g., polyethylene glycol 1000 monocetyl ether).

Non-limiting examples of preferred surfactants, which have a HLB of 4-19 are set out in the Table below:

| Surfactant | HLB |
|---|---|
| steareth 2 | ~4.9 |
| glyceryl monostearate/PEG 100 stearate | Av ~11.2 |
| Glyceryl Stearate | ~4 |
| Steareth-21 | ~15.5 |
| peg 40 stearate | ~16.9 |
| polysorbate 80 | ~15 |
| sorbitan stearate | ~4.7 |
| laureth 4 | ~9.7 |
| Sorbitan monooleate (span 80) | ~4.3 |
| ceteareth 20 | ~15.7 |
| steareth 20 | ~15.3 |
| ceteth 20 | ~15.7 |
| Macrogol Cetostearyl Ether | ~15.7 |
| ceteth 2 (Lipocol C-2) | ~5.3 |
| PEG-30 Dipolyhydroxystearate | ~5.5 |
| sucrose distearate (Sisterna SP30) | ~6 |
| polyoxyethylene (100) stearate | ~18.8 |

More exemplary stabilizing surfactants which may be suitable for use in the present invention are found below.

PEG-Fatty Acid Monoester Surfactants

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants:

| Chemical name | Product example name | HLB |
|---|---|---|
| PEG-4 dilaurate | Mapeg .RTM. 200 DL (PPG), Kessco .RTM.PEG 200 DL (Stepan), LIPOPEG 2-DL (Lipo Chem.) | 7 |
| PEG-4 | distearate Kessco .RTM. 200 DS (Stepan.sub) | 5 |
| PEG-32 dioleate | Kessco .RTM. PEG 1540 DO (Stepan) | 15 |
| PEG-400 dioleate | Cithrol 4DO series (Croda) | >10 |
| PEG-400 disterate | Cithrol 4DS series (Croda) | >10 |
| PEG-20 glyceryl oleate | Tagat .RTM. O (Goldschmidt) | >10 |

Transesterification Products of Oils and Alcohols

| Chemical name | Product example name | HLB |
|---|---|---|
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
|---|---|---|
| Polyglyceryl-6 dioleate | Caprol .RTM. 6G20 (ABITEC); PGO-62 (Calgene), PLUROL OLEIQUE CC 497 (Gattefosse)Hodag | 8.5 |

PEG-Sorbitan Fatty Acid Esters

| Chemical name | Product example name | HLB |
|---|---|---|
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan monooleate | Tween-80 (Atlas/ICI), Crillet 4 (Croda) | 15 |

Polyethylene Glycol Alkyl Ethers

| Chemical name | Product example name | HLB |
|---|---|---|
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants

| Chemical name | Product example name | HLB |
|---|---|---|
| Sucrose distearate | Sisterna SP50, Surfope 1811 | 11 |

Sorbitan Fatty Acid Ester Surfactants

| Chemical name | Product example name | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable formulation or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij 10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequistearate; polymeric emulsifiers, such as Permulen (TR1 or TR2); liquid crystal systems, such as Arlatone (2121), Stepan (Mild RM1), Nikomulese (41) and Montanov (68) and the like.

In certain embodiments the surfactant is preferably one or more of the following: a combination of steareth-2 and steareth-21 on their own or in combination with glyceryl monostearate (GMS); in certain other embodiments the surfactant is a combination of polysorbate 80 and PEG-40 stearate. In certain other embodiments the surfactant is a combination of glyceryl monostearate/PEG 100 stearate. In certain other embodiments the surfactant is a combination of two or more of stearate 21, PEG 40 stearate, and polysorbate 80. In certain other embodiments the surfactant is a combination of two or more of laureth 4, span80, and polysorbate 80. In certain other embodiments the surfactant is a combination of two or more of GMS and ceteareth. In certain other embodiments the surfactant is a combination of two or more of steareth 21, ceteareth 20, ceteth 2 and laureth 4 In certain other embodiments the surfactant is a combination of ceteareth 20 and polysorbate 40 stearate. In certain orther embodiments the surfactant is a combination of span 60 and GMS. In certain other embodiments the surfactant is a combination of two or all of PEG 40 stearate, sorbitan stearate and polysorbate 60

In certain other embodiments the surfactant is one or more of sucrose stearic acid esters, sorbitan laureth, and sorbitan stearate.

Without being bound by any particular theory or mode of operation, it is believed that the use of non-ionic surfactants with significant hydrophobic and hydrophilic components, increase the emulsifier or foam stabilization characteristics of the composition. Similarly, without being bound by any particular theory or mode of operation, using combinations of surfactants with high and low HLB's to provide a relatively close packed surfactant layer may strengthen the formulation.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect In one or more embodiments the surfactant is a surfactant or surfactant combination is capable of or which tends to form liquid crystals. Surfactants which tend to form liquid crystals may improve the quality of foams. Non limiting examples of surfactants with postulated tendency to form interfacial liquid crystals are: phospholipids, alkyl glucosides, sucrose esters, sorbitan esters.

In one or more embodiments the at least one surface active agent is liquid. Moreover for the purposes of formulating with liquid ethers a liquid surfactant is preferred In one or more embodiments the liquid surfactant is a polysorbate, preferably polysorbate 80 or 60.

In one or more embodiments the at least one surface active agent is solid, semi solid or waxy. In a further embodiment they are soluble in oil and in another embodiment have a HLB of less than about 12.

It should be noted that HLB values may not be so applicable to non ionic surfactants, for example, with liquid crystals or with silicones. Also HLB values may be of lesser significance in a waterless or substantially non-aqueous environment.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier. In a preferred embodiment at least one surfactant is a liquid.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions of the present invention.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1

In one or more embodiments, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

For foams in selecting a suitable surfactant or combination thereof it should be borne in mind that the upper amount of surfactant that may be used may be limited by the shakability of the composition. If the surfactant is non liquid, it can make the formulation to viscous or solid. Subject to its miscibily solid surfactants may be added first, and may require gentle warming and then cooling before being combined with the other ingredients. In general terms, as the amount of non-liquid surfactant is increased the shakability of the formulation reduces until a limitation point is reached where the formulation can become non shakable and unsuitable. Thus in one embodiment, any effective amount of surfactant may be used provided the formulation remains shakable. In other certain limited embodiments the upper limit for foamable formulations may be determined by flowability such that any effective amount can be used provided the formulation is sufficiently flowable to be able to flow through an actuator valve and be released and still expand to form a good quality foam. This may be due without being bound by any theory to one or more of a number of factors such as the viscosity, the softness, the lack of crystals, the pseudoplastic or semi pseudo plastic nature of the composition and the dissolution of the propellant into the composition.

In certain embodiments the amount of surfactant or combination of surfactants is between about 0.05% to about 20%; between about 0.05% to about 15%. or between about 0.05% to about 10%. In a preferred embodiment the concentration of surface active agent is between about 0.2% and about 8%. In a more preferred embodiments the concentration of surface active agent is between about 1% and about 6% or between about 1% and about 4%.

In some embodiments, it is desirable that the surface active agent does not contain a polyoxyethylene (POE) moiety, such as polysorbate surfactants, POE fatty acid esters, and POE alkyl ethers, because the active agent is incompatible with such surface active agents. For example, the active agent pimecrolimus is not stable the presence of POE moieties, yet benefits greatly from the use of dicarboxylic esters as penetration enhancers. In such cases, alternative surface active agents are employed. In an exemplary manner, POE—free surfactants include non-ethoxylated sorbitan esters, such as sorbitan monopalmitate, sorbitan monostearate, sorbitan tristearate, sorbitan monooleate, sorbitan trioleate, sorbitan monolaurate and sorbitan sesquioleate; glycerol fatty acid esters, such as glycerol monostearate and glycerol monooleate; mono-, di- and tri-esters of sucrose with fatty acids (sucrose esters), sucrose stearate, sucrose distearate sucrose palmitate and sucrose laurate; and alkyl polyglycosides, such as lauryl diglucoside.

In one or more embodiments, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher HLB values.

In one or more preferred embodiments of the present invention the surfactant includes at least one surfactant selected from a polyoxyethylene fatty ether, a polyoxyethylene fatty ester, a carbohydrate ester and a sucrose ester.

In one or more embodiments non limiting examples of non-ionic surfactants include steareth-2, steareth-20, steareth-21, ceteareth 2, PEG-100 stearyl ether, cetearyl glucoside, methyl glucose sesquistearate, sorbitan monostearate, GMS NE and span 20.

In one or more embodiments non limiting other examples of surfactant combinations are glyceryl stearate and PEG 100 stearate and laureth4; steareth 2, PEG 100 searate and laureth4; and cetearyl glucoside and cetearyl alcohol.

In an embodiment the surfactant containing formulations are further boosted by a foam adjuvant for example stearyl alcohol.

A non limiting example of a combination of surfactants having a weighted average of their HLB values of 11 is Glyceryl Stearate and PEG-100 Stearate (for example trade name "simulsol 165" from Sepic).

Hydrophobic Solvent

Optionally, the foamable carrier further contains at least one hydrophobic solvent. The identification of a "hydrophobic solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL.

In one or more embodiments, the hydrophobic organic carrier is an oil, such as mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. In one or more further embodiments the hydrophobic organic carrier is petrolatum.

Humectant

A humectant, is a substance that helps retain moisture and also prevents rapid evaporation. Non limiting examples of suitable heumectants are propylene glycol, propylene glycol derivatives, and glycerin. Other examples of humectants and moisturizers may be found in the Handbook of Pharmaceutical Additives published by Gower. Suitable ones for use with and soluble in the waterless compositions of the present invention may be selected as will be appreciated by a person skilled in the art.

Moisturizers

A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Glycerine and sodium pCA work in combination. Other examples may be found in the *Handbook of Pharmaceutical Additives* published by Gower.

Pharmaceutical compositions of the present invention may in one or more embodiments usefully comprise in addition a humectant or a moisturizer or combinations thereof.

Foam Adjuvant

Optionally, a foam adjuvant is included in the foamable carriers of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

Additional Components

In an embodiment of the present invention, a composition of the present invention includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins and flavonoids. As is known to one skilled in the art, in some instances a specific additional component may have more than one activity, function or effect.

In an embodiment of the present invention, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment of the present invention, the additional component is an emollient. Suitable emollients include but are not limited to mineral oil, lanolin oil, coconut oil, cocoa butter, olive oil, aloe vera extract, jojoba oil, castor oil, fatty acids, fatty alcohols, diisopropyl adipate, hydroxybenzoate esters, benzoic acid esters of C9 to C15 alcohols, isononyl iso-nonanoate, silicone oils, polyethers, C12 to C15 alkyl benzoates, oleic acid, stearic fatty acid, cetyl alcohols, hexadecyl alcohol, dimethyl polysiloxane, polyoxypropylene cetyl ether, polyoxypropylene butyl ether, and derivatives, esters, salts and mixtures thereof.

In an embodiment of the present invention, the additional component is a humectant. Suitable humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof.

In an embodiment of the present invention, the additional component is a preservative. Suitable preservatives include but are not limited to C12 to C15 alkyl benzoates, alkyl p-hydroxybenzoates, aloe vera extract, ascorbic acid, benzalkonium chloride, benzoic acid, benzoic acid esters of C9 to C15 alcohols, butylated hydroxytoluene, castor oil, cetyl alcohols, chlorocresol, citric acid, cocoa butter, coconut oil, diazolidinyl urea, diisopropyl adipate, dimethyl polysiloxane, DMDM hydantoin, ethanol, fatty acids, fatty alcohols, hexadecyl alcohol, hydroxybenzoate esters, iodopropynyl butylcarbamate, isononyl iso-nonanoate, jojoba oil, lanolin oil, methylparaben, mineral oil, oleic acid, olive oil, polyethers, polyoxypropylene butyl ether, polyoxypropylene cetyl ether, potassium sorbate, silicone oils, sodium propionate, sodium benzoate, sodium bisulfite, sorbic acid, stearic fatty acid, vitamin E, vitamin E acetate and derivatives, esters, salts and mixtures thereof.

In an embodiment of the present invention, the additional component is a skin penetration enhancer. Suitable skin penetration enhancers include but are not limited to acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl)ether, diisopropyl adipate, diisopropyl sebacate, N,N-dimethyl acetamide, dimethyl azelate, N,N-dimethyl formamide, 1,5-dimethyl-2-pyrrolidone, dimethyl sebacate, dimethyl sulphoxide, dioctyl adipate, dioctyl azelate, dioctyl sebacate, 1,4 dioxane, 1-dodecylazacyloheptan-2-one, dodecyl dimethyl amine oxides, ethyl caprate, ethyl caproate, ethyl caprylate, 2-ethyl-hexyl pelargonate, ethyl-2-hydroxypropanoate, ethyl laurate, ethyl myristate, 1-ethyl-2-pyrrolidone, ethyl salicylate, hexyl laurate, 2-hydroxyoctanoic acid, 2-hydroxypropanoic acid, 2-hydroxypropionic acid, isethionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methyl propan-2-ol, 1-methyl-2-pyrrolidone, 5-methyl-2-pyrrolidone, methyl taurides, miranol, nonionic surface-active agents, octyl alcohol, octylphenoxy polyethoxyethanol, oleic ethanolamide, pleyl alcohol, pentan-2,4-diol, phenoxyethanol, phosphatidyl choline, phosphine oxides, polyalkoxylated ether glycollates, poly(diallylpiperidinium chloride), poly(dipropyldiallylammonium chloride), polyglycerol esters, polyoxyethylene lauryl ether, polyoxy:polyoxyethylene stearate, polyoxypropylene 15 stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternised poly (dimethylaminoethylmethacrylate), quaternised poly (vinyl alcohol), sapamin hydrochloride, sodium cocaminopropionate, sodium dioctyl sulphonsuccinate, sodium laurate, sodium lauryl ether sulphate, sodium lauryl sulphate, sugar esters, sulphosuccinate, tetrahydrofuran, tetrahydrofurfural alcohol, transcutol, triethanolamine dodecyl benzene sulphonate, triethanolamine oleate, urea, water and derivatives, esters, salts and mixtures thereof.

In an embodiment the composition with modulating agent may be used as is without addition of a propellant. In other embodiments propellant is added to form a foamable composition that produces a foam when the formulation is expelled from a pressurized canister. The foam may be of various qualities as indicated herein. In a preferred embodiment the foam is of about good quality. In a more preferred embodiment it is of about excellent quality.

Propellants

Examples of suitable propellants include volatile hydrocarbons such as butane, propane, isobutane and fluorocarbon gases, or mixtures thereof.

In an embodiment the propellant is AP 70 which is a mixture of propane, isobutene and butane.

The propellant makes up about 5-25 wt % of the foamable composition. In some circumstances the propellant may be upto 35%. The propellants are used to generate and administer the foamable composition as a foam. The total composition including propellant, foamable compositions and optional ingredients is referred to as the foamable composition.

Alcohol and organic solvents render foams inflammable. It has been surprisingly discovered that fluorohydrocarbon propellants, other than chloro-fluoro carbons (CMCs), which are non-ozone-depleting propellants, are particularly useful in the production of a non-flammable foamable composition. A test according to European Standard prEN 14851, titled "Aerosol containers—Aerosol foam flammability test" revealed that compositions containing an organic carrier that contains a hydrophobic organic carrier and/or a polar solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluorethane (Dymel 134), and 1,1,1,2,3,3,3 heptafluoropropane (Dymel 227) 1,1, difluoro ethane (Dymel 152) and 1,1,1,3,3,3 hexafluoropropane HFCs possess Ozone Depletion Potential of 0.00 and thus, they are allowed for use as propellant in aerosol products.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butane or mixtures of hydrocarbon propellants such as propane, isobutane and butane.

Composition and Foam Physical Characteristics and Advantages

A pharmaceutical or cosmetic composition manufactured using the foamable carrier of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition of the present invention is stable, having an acceptable shelf-life of months or preferably at least one year, or more preferably, at least two years at ambient temperature, as revealed in accelerated stability tests. Organic carriers and propellants tend to impair the stability of emulsions and to interfere with the formation of stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

A further aspect of the foam is breakability. Thermally sensitive foams immediately collapse upon exposure to skin temperature and, therefore, cannot be applied on the hand and afterwards delivered to the afflicted area.

The foam of the present invention has several advantages, when compared with hydroalcoholic foam compositions, such as (1) Breakability. The foam of the present invention is thermally stable and breakable under sheer force but is not "quick breaking which allows comfortable application and well directed administration to the target area;

(2) Skin drying and skin barrier function. Short chain alcohols are known to dry the skin and impair the integrity of the skin barrier. By contrast, including a film forming agent in the composition of the present invention foes not cause unwanted skin barrier damage; and (3) Irritability. Due to the lack of alcohol and improvement in skin barrier function, skin irritability is eliminated or reduced.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Pharmaceutical Composition

The compositions, the foamable compositions and the foams of the present invention are ideal vehicles for active pharmaceutical ingredients and active cosmetic ingredients. In the context of the present invention, active pharmaceutical ingredients and active cosmetic ingredients are collectively termed "active agent" or "active agents". A foamable composition, comprising an active agent has the following advantages:

1. The foamable composition provides a preferred solvent for active agents, particularly water-insoluble agents.
2. The inclusion of a polyol and/or a PEG and a secondary polar solvent in the foamable composition facilitates a co-solvent effect, resulting increased concentrations of soluble active agent in the dosage form, thus facilitating enhanced skin penetration of the active agent. In many cases, increased penetration is positively correlated with improved clinical outcome. In certain case, attaining an increased drug penetration into the target site of action enables a decrease of treatment frequency, for example, from twice or three times daily to once daily.
3. Polyols and PEGs; and combinations of a polyol and/or PEG with a secondary polar solvent are known as skin penetration enhancers, thus, increasing drug residence in the target area and increasing clinical efficacy, as detailed above.
4. The fact that the compositions contains no water, or merely up to 5% and water minimizes the probability of degradation of water-sensitive active agents. Furthermore, as exemplified herein, a foam containing a polyol and/or PEG with no water at all can be formed in accordance with the composition and process of the present invention. Such compositions ensure high stability of water sensitive active agents.
5. Combining the anti-infective effect of a water-free, thus hygroscopic composition, which acts through a dehydration mechanism, with an additional anti-infective agent, selected from the group of an antibiotic agent, an antibacterial agent, an antifungal agent, an agent that controls yeast, an antiviral agent and an antiparasitic agent, that acts through alternate mechanisms results in a synergistic effect and consequently higher success rate of the treatment.
6. The foamable polyol composition in contained in an impermeable pressurized packaging presentation is impermeable and thus, the active agent is not exposed to environmental degradation factors, such as light and oxidating agent during storage.

Thus, in a preferred embodiment of the present invention, the composition includes at least one active agent.
  a. a therapeutically effective concentration of an active agent;
  b. a modulating agent;
  c. about 50% to about 98% of a polar solvent, selected from the group consisting of a polyol and a polyethylene glycol;
  d. 0% to about 48% of a secondary polar solvent;
  e. about 0.2% to about 5% by weight of a surface-active agent;
  f. about 0.01% to about 5% by weight of at least one polymeric agent; and for a foamable composition additionally
  g. a liquefied or compressed gas propellant at a concentration of about 3% to about 25% by weight of the total composition.
wherein the composition is stored in an aerosol container and upon release expands to form a breakable foam.

Active Agents

Suitable active agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin D derivatives, flavonoids, wound healing agents and wart removers. As is known to one skilled in the art, in some instances a specific active agent may have more than one activity, function or effect.

In an embodiment of the present invention, the active agent is an active herbal extract. Suitable active herbal extracts include but are not limited to angelica, anise oil, astragali radix, azalea, benzyl acetate, birch tar oil, bornyl acetate, cacumen biotae, camphor, cantharidin, capsicum, cineole, cinnamon bark, cinnamon leaf, citronella, citroneliol, citronellyl acetate, citronellyl formate, eucalyptus, eugenyl acetate, flos carthami, fructus mori, garlic, geraniol, geranium, geranyl acetate, habanera, isobutyl angelicate, lavender, ledum latifolium, ledum palustre, lemongrass, limonene, linalool, linalyl acetate, methyl anthranilate, methyl cinnamate, mezereum, neem, nerol, neryl acetate, nettle root extract, oleum ricini, oregano, pinenes, .alpha.-pinene, .beta.-pinene, radix angelicae sinesis, radix paenoiae rubra, radix polygoni multiflori, radix rehmanniae, rhizoma pinelliae, rhizoma zingiberis recens, sabadilla, sage, sandalwood oil, saw palmetto extract, semen sesami nigrum, staphysagria, tea tree oil, terpene alcohols, terpene hydrocarbons, terpene esters, terpinene, terpineol, terpinyl acetate and derivatives, esters, salts and mixtures thereof. In an embodiment of the present invention, the active agent is an acaricide. Suitable acaricides include but are not limited to amitraz, flumethrin, fluvalinate and derivatives, esters, salts and mixtures thereof.

In an embodiment of the present invention, the active agent is an age spot and keratoses removing agent. Suitable age spot and keratoses removing agent include but are not limited to hydroxy acids, azelaic acid and other related dicarboxylic acids, retinoids, kojic acid, arbutin, nicotinic, ascorbic acid, hydroquinone and derivatives, esters, salts and mixtures thereof. Certain nonsteroidal anti-inflammatory agents, such as diclofenac are also useful for the treatment of keratoses.

In an embodiment of the present invention, the active agent is an analgesic. Suitable analgesics include but are not limited to benzocaine, butamben picrate, dibucaine, dimethisoquin, dyclonine, lidocaine, pramoxine, tetracaine, salicylates and derivatives, esters, salts and mixtures thereof.

In an embodiment of the present invention, the active agent is a local anesthetic. Suitable local anesthetics include but are not limited to benzocaine, benzyl alcohol, bupivacaine, butamben picrate, chlorprocaine, cocaine, dibucaine, dimethisoquin, dyclonine, etidocaine, hexylcaine, ketamine, lidocaine, mepivacaine, phenol, pramoxine, procaine, tetracaine, salicylates and derivatives, esters, salts and mixtures thereof.

In an embodiment of the present invention, the active agent is an antiacne agent. Suitable antiacne agents include but are not limited to N-acetylcysteine, adapalene, azelaic acid, benzoyl peroxide, cholate, clindamycin, deoxycholate, erythromycin, flavinoids, glycolic acid, meclocycline, metronidazol, mupirocin, octopirox, phenoxy ethanol, phenoxy proponol, pyruvic acid, resorcinol, retinoic acid, salicylic acid, scymnol sulfate, sulfacetamide-sulfur, sulfur, tazarotene, tetracycline, tretinoin triclosan and derivatives, esters, salts and mixtures thereof.

In an embodiment of the present invention, the active agent is an antiaging agent. Suitable antiaging agents include but are not limited to sulfur-containing D and L amino acids, alpha-hydroxy acids s, beta-hydroxy acids (e.g. salicylic acid), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate) skin barrier forming agents, melatonin and derivatives, esters, salts and mixtures thereof.

In an embodiment of the present invention, the active agent is an antibiotic. The terms "antibiotic" as used herein shall include, but is not limited to, any substance being destructive to or inhibiting the growth of bacteria or any substance having the capacity to inhibit the growth of or to destroy bacteria. In one or more embodiments, the antibiotic active agent is selected from the group consisting of a beta-lactam antibiotic, an aminoglycoside, an ansa-type antibiotic, an anthraquinone, an azole, an antibiotic glycopeptide, a macrolide, an antibiotic nucleoside, an antibiotic peptide, an antibiotic polyene, an antibiotic polyether, an antibiotic quinolone, an antibiotic steroid, a sulfonamide, an antibiotic metal, an oxidizing agent, a periodate, a hypochlorite, a permanganate, a substance that release free radicals and/or active oxygen, a cationic antimicrobial agent, a quaternary ammonium compound, a biguanide, a triguanide, a bisbiguanide, a polymeric biguanide, and analogs, derivatives, salts, ions and complexes thereof.

Suitable antibiotics include but are not limited to amanfadine hydrochloride, amanfadine sulfate, amikacin, arnikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocyldline, iodate, iodine, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, microcrystalline and nanocrystalline particles of silver, copper, zinc, mercury, tin, lead, bismuth, cadmium and chromium, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

In an embodiment of the present invention, the active agent is an antidandruff agent. Suitable antidandruff agents include but are not limited to aminexil, benzalkonium chloride, benzethonium chloride, 3-bromo-1-chloro-5,5-dimethyl-hydantoin, chloramine B, chloramine T, chlorhexidine, N-chlorosuccinimide, climbazole-, 1,3-dibromo-5,5-dimethylhydantoin, 1,3-dichloro-5,5-dimethyl-hydantoin, betulinic acid, betulonic acid, celastrol, crataegolic acid, cromakalin, cyproterone acetate, dutasteride, finesteride, ibuprofen, ketoconozole, oleanolic acid, phenyloin, picrotone olamine, salicylic acid, selenium sulphides, triclosan, triiodothyronine, ursolic acid, zinc gluconate, zinc omadine, zinc pyrithione and derivatives, esters, salts and mixtures thereof.

In an embodiment of the present invention, the active agent is an antihistamine. Suitable antihistamines include but are not limited to chlorcyclizine, diphenhydramine, mepyramine, methapyrilene, tripelennamine and derivatives, esters, salts and mixtures thereof.

In an embodiment of the present invention, the active agent is an antimycotic Also termed antifungal agent. The terms "antimycotic" and "antifungal" as used herein include, but is not limited to, any substance being destructive to or inhibiting the growth of fungi and yeast or any substance having the capacity to inhibit the growth of or to destroy fungi and/or yeast.

In one or more embodiments, the antifungal agent is an agent that is useful in the treatment of a superficial fungal infection of the skin, dermatophytosis, microsporum, trichophyton and epidermophyton infections, candidiasis, oral candidiasis (thrush), candidiasis of the skin and genital mucous membrane, candida paronychia, which inflicts the nail and nail bed and genital and vaginal candida, which inflict genitalia and the vagina.

Suitable antimycotics include but are not limited to allylamines, amorolfine, amphotericin B, azole compounds, bifonazole, butoconazole, chloroxine, clotrimazole, ciclopirox olamine, clotrimazole, econazole, elubiol, fenticonazole, fluconazole, flucytosine (5FC), griseofulvin, itraconazole, ketoconazole, mafenide acetate, miconazole, naftifine, natamycin, tolnaftate, nystatin, polyenes, oxiconazole, sulbentine, sulconazole, terbinafine, terconazole, tioconazole, undecylenic acid and derivatives, esters, salts and mixtures thereof.

In an embodiment of the present invention, the active agent is an antipruritic. Suitable antipruritics include but are not limited to menthol, methdilazine, trimeprazine, urea and derivatives, esters, salts and mixtures thereof.

In an embodiment of the present invention, the active agent is an additional antipsoriatic agent. Suitable additional antipsoriatic agents include but are not limited to 6-aminonicotinamide, 6-aminonicotinic acid, 2-aminopyrazinamide, anthralin, 6-carbamoylnicotinamide, 6-chloronicotinamide, 2-carbamoylpyrazinamide, corticosteroids, 6-dimethylaminonicotinamide, dithranol, 6-formylaminonicotinamide, 6-hydroxy nicotinic acid, 6-substituted nicotinamides, 6-substituted nicotinic acid, 2-substituted pyrazinamide, tazarotene, thionicotinamide, trichothecene mycotoxins and derivatives, esters, salts and mixtures thereof.

In an embodiment of the present invention, the active agent is an antirosacea agent. Suitable antirosacea agents include but are not limited to azelaic acid, metronidazole, sulfacetamide and derivatives, esters, salts and mixtures thereof. Certain nonsteroidal anti-inflammatory agents, such as salicylic acid, salycilates, piroxicam and diclofenac are also useful for the treatment of Rosacea.

In an embodiment of the present invention, the active agent is an antiseborrheic agent. Suitable antiseborrheic agents include but are not limited to glycolic acid, salicylic acid, selenium sulfide, zinc pyrithione, a dicarboxylic acid, such as azelaic acid and derivatives, esters, salts and mixtures thereof.

In an embodiment of the present invention, the active agent is an antiviral agent. Suitable antiviral agents include but are not limited to acyclovir, gancyclovir, ribavirin, amantadine, rimantadine nucleoside-analog reverse transcriptase inhibitors, such as zidovudine, didanosine, zalcitabine, tavudine, lamivudine and vidarabine, non-nucleoside reverse transcriptase inhibitors, such as nevirapine and delavirdine, protease inhibitors, such as saquinavir, ritonavir, indinavir and nelfinavir, and interferons and derivatives, esters, salts and mixtures thereof.

In an embodiment of the present invention, the active agent is a chemotherapeutic agent. Suitable chemotherapeutic agents include but are not limited to daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, XR9576 and derivatives, esters, salts and mixtures thereof.

In an embodiment of the present invention, the active agent is a corticosteroid. Suitable corticosteroids include but are not limited to alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, difluorosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters, salts and mixtures thereof.

In an embodiment of the present invention, the active agent is a hair growth regulator. Suitable hair growth regulators include but are not limited to N-acetylgalactosamine, N-acetylglucosamine, N-acetylmannosamine, acitretin, aminexil, ascomycin, asiatic acid, azelaic acid, benzalkonium chloride, benzethonium chloride, benzydamine, benzyl nicotinate, benzoyl peroxide, benzyl peroxide, betulinic acid, betulonic acid, calcium pantothenate, celastrol, cepharanthine, chlorpheniramine maleate, clinacycin hydrochloride, crataegolic acid, cromakalin, cyproterone acetate, diazoxide, diphenhydramine hydrochloride, dutasteride, estradiol, ethyl-2-hydroxypropanoate, finasteride, D-fucono-1,5-lactone, furoate, L-galactono-1,4-lactone, D-galactosamine, D-glucaro-1,4-lactone, D-glucosamine-3-sulphate, hinokitiol, hydrocortisone, 2-hydroxypropionic acid, isotretinoin, itraconazole, ketoconazole, latanoprost, 2-methyl propan-2-ol, minocyclin, minoxidil, mipirocin, mometasone, oleanolic acid, panthenol, 1,10-phenanthroline, phenyloin, prednisolone, progesterone, propan-2-ol, pseudoterins, resorcinol, selenium sulfide, tazarotene, triclocarbon, triclosan, triiodothyronine, ursolic acid, zinc pyrithione and derivatives, esters, salts and mixtures thereof.

In an embodiment of the present invention, the active agent is a hormone. Suitable hormones include but are not limited to methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5a-dihydrotestosterone, testolactone, 17a-methyl-19-nortestosterone, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5a-pregnan-3b,20a-diol sulfate, 5a-pregnan-3b,20b-diol sulfate, 5a-pregnan-3b-ol-20-one, 16,5a-pregnen-3b-ol-20-one, 4-pregnen-20b-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone, progestins and derivatives, esters, salts and mixtures thereof.

In an embodiment of the present invention, the active agent is a hydroxyacid. Suitable hydroxy acids include but are not limited to agaricic acid, aleuritic acid, allaric acid, altraric acid, arabiraric acid, ascorbic acid, atrolactic acid, benzilic acid, citramalic acid, citric acid, dihydroxytartaric acid, erythraric acid, galactaric acid, galacturonic acid, glucaric acid, glucuronic acid, glyceric acid, glycolic acid, gularic acid, gulonic acid, hydroxypyruvic acid, idaric acid, isocitric acid, lactic acid, lyxaric acid, malic acid, mandelic acid, mannaric acid, methyllactic acid, mucic acid, phenyllactic acid, pyruvic acid, quinic acid, ribaric acid, ribonic acid, saccharic acid, talaric acid, tartaric acid, tartronic acid, threaric acid, tropic acid, uronic acids, xylaric acid and derivatives, esters, salts and mixtures thereof.

In an embodiment of the present invention, the active agent is a keratolytic agent. The term "keratolytic agent" is used herein to mean a compound which loosens and removes the stratum corneum of the skin, or alters the structure of the keratin layers of skin. Keratolytic agents are used in the treatment of many dermatological disorders, which involve dry skin, hyperkeratiinization (such as prsoriasis), skin itching (such as xerosis), acne and rosacea. Suitable keratolytic agents include but are not limited to N-acetylcysteine, azelaic acid, cresols, dihydroxy benzene compounds, such as resorcinol and hydroquinone, alpha-hydroxy acids, such as lactic acid and glycolic acid, phenol, pyruvic acid, resorcinol, sulfur, salicylic acid, retinoic acid, isoretinoic acid, retinol, retinal, urea and derivatives, esters, salts and mixtures thereof.

In an embodiment of the present invention, the active agent is a lactam. Suitable lactams include but are not limited to L-galactono-1,4-lactam, L-arabino-1,5-lactam, D-fucono-1, 5-lactam, D-glucaro-1,4-lactam, D-glucurono-6,3-lactam, 2,5-tri-O-acetyl-D-glucurono-6,3-lactam, 2-acetamido-2-deoxyglucono-1,5-1-actam, 2-acetamido-2-deoxygalactono-1,5-lactam, D-glucaro-1,4:6,3-dilactam-, L-idaro-1,5-lactam, 2,3,5,tri-O-acetyl-D-glucaro-1,4-lactam, 2,5-di-O-acetyl-D-glucaro-1,4:6,3-dilactam, D-glucaro-1,5-lactam methyl ester, 2-propionoamide-2-deoxyglucaro-1,5-lactam and derivatives, esters, salts and mixtures thereof.

In an embodiment of the present invention, the active agent is a non-steroidal anti-inflammatory agent. Suitable non-steroidal anti-inflammatory agent include but are not limited to azelaic acid, oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof.

In an embodiment of the present invention, the active agent is insecticide. The term "insecticide, is used herein to mean a compound which kills, inhibits the growth of, impeded the proliferation of or repels insects. Insecticides include, for example, agents that can kill lice, flees, ticks, mites, scabies and mosquitos, as well as agents that repel such insects. Suitable insecticides include but are not limited to DDT, lindane, malathion, permethrin, allethrin, biopermethrin, transpermethrin, phenothrin, diethyl-m-toluamide, dimethyl phthalate, piperonyl butoxide, pyrethroids and derivatives, esters, salts and mixtures thereof.

In an embodiment of the present invention, the active agent is a vasodilator. Suitable vasodilators include but are not limited to agents that modulate the activity of the enzyme nitric oxide synthase, nicotinic acid, ethyl nicotinate, amyl nitrite, amyl nitrate, ethyl nitrite, butyl nitrite, isobutyl nitrite, glyceryl trinitrate, octyl nitrite, sodium nitrite, sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, troInitrate phosphate (triethanolamine trinitrate diphosphate), propatylnitrate, nitrite esters of sugars, nitrite esters of polyols, nitrate esters of sugars, nitrate esters of polyols, nicorandil, apresoline, diazoxide, hydralazine, hydrochlorothiazide, minoxidil, pentaerythritol, tolazoline, scoparone, a beta-adrenergic blocker, an alpha-adrenoceptor blocker, a prostaglandin, sildenafil, dipyridamole, catecholamine, isoproternol, furosemide, prostaglandin, prostacyclin, enalaprilat, morphine, acepromazine, prazosin (α-blocker), enalapril, Captopril, amlodipine, minoxidil, tadalafil, vardenafil, phenylephrin, etilefein, caffeine, capsaicin, an extract capsicum, achillea millefolium (Yarrow), allium sativum (garlic), amoracia rusticana (horseradish), berberis vulgaris (barberry), cimicifuga racemosa (black cohosh), coleus forskholii (coleus), coptis (goldenthread), crataegus (hawthorn), eleutherococcus senticosus (siberian ginseng), ginkgo biloba (ginkgo), melissa offiicnalis (lemon balm), olea europaea (olive leaf), panax ginseng (Chinese ginseng), petroselinum crispum (parsley), scutellaria baicalensis (baical skullcap), tilia europaea (linden flower), trigonella foenum-graecum (fenugreek), urtica dioica (nettles), valeriana officinalis (valerian), viburnum (cramp, bark, black haw), veratrum viride (American hellebore), verbena officinalis (vervain), xanthoxylum americanum (prickly ash), zing iber officinale (ginger), rauwolfia serpentina (Indian snakeroot), viscum album, wild yam, sasparilla, licorice, damiana, yucca, saw palmetto, gotu kola (centella asiatica), yohimbine and salts, hazel nut, brazil nut and walnut, and derivatives, esters, salts and mixtures thereof.

In an embodiment of the present invention, the active agent is a vasoconstrictor. Suitable vasodilators include but are not limited to ephedrine, epinephrine, phenylephrine, angiotensin, vasopressin; an extract ephedra sinica (ma huang), polygonum bistorta (bistort root), hamamelis virginiana (witch hazel), hydrastis canadensis (goldenseal), lycopus virginicus (bugleweed), aspidosperma quebracho (quebracho blanco), cytisus scoparius (scotch broom) and cypressand and derivatives, esters, salts and mixtures thereof.

In an embodiment of the present invention, the active agent is a retinoid. Suitable retinoids include but are not limited to retinol, retinal, retinoic acid, all-trans retinoic acid, isotretinoin, tazarotene, adapalene, 13-cis-retinoic acid, acitretin all-trans beta carotene, alpha carotene, lycopene, 9-cis-beta-carotene, lutein and zeaxanthin.

In an embodiment of the present invention, the active agent is a vitamin D analog. Suitable retinoids include but are not limited to calcipotriene, cholecalciferol, 25-hydroxycholecalciferol, 1α,25-dihydroxycholecalciferol, ergocalciferol, 1α,25-dihydroxyergocalciferol, 22,23-dihydroergocalciferol, 1,24,25-trihydroxycholecalciferol, previtamin $D_3$, tachysterol$_3$ (also termed tacalciol), isovitamin $D_3$, dihydrotachysterol$_3$, (1S)-hydroxycalciol, (24R)-hydroxycalcidiol, 25-fluorocalciol, ercalcidiol, ertacalciol, (5E)-isocalciol, 22,23-dihydroercalciol, (24S)-methylcalciol, (5E)-(10S)-10, 19-dihydroercalciol, (24S)-ethylcalciol and (22E)-(24R)-ethyl-22,23-didehydrocalciol. In a preferred embodiment, the vitamin D analog is calcipotriene, which is useful in the treatment of psoriasis.

In an embodiment of the present invention, the active agent is selected from the group consisting of an immunosuppressants and immunoregulating agents. Suitable immunosuppressants and immunoregulating agents include but are not limited to cyclic peptides, such as cyclosporine, tacrolimus, tresperimus, pimecrolimus, sirolimus (rapamycin), verolimus, laflunimus, laquinimod, imiquimod derivatives, esters, salts and mixtures thereof. In one or more embodiments, the immunomodulator is a calcineurin Inhibitor.

In an embodiment of the present invention, the active agent is a wart remover. Suitable wart removers include but are not limited to imiquimod, podophyllotoxin and derivatives, esters, salts and mixtures thereof.

In an embodiment of the present invention, the active agent is a photodynamic therapy (PDT) agent. Suitable PDT agents include but are not limited to modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitiser precursors, such as aminolevulinic acid and derivatives, esters, salts and mixtures thereof.

In an embodiment of the present invention, the active agent is an antioxidant or a radical scavenger. Suitable antioxidants and radical scavengers agents include but are not limited to ascorbic acid, ascorbyl esters of fatty acids, magnesium ascorbyl phosphate, sodium ascorbyl phosphate, ascorbyl sorbate, tocopherol, tocopheryl sorbate, tocopheryl acetate, butylated hydroxy benzoic acid, 6-hydroxy-2,5,7,8-tetramethylchroman-2-carboxylic acid, gallic acid, propyl gallate, uric acid, sorbic acid, lipoic acid, diethylhydroxylamine, amino-guanidine, glutathione, dihydroxy fumaric acid, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and polyunsaturated oils, containing omega-3 and omega-6 fatty acids (e.g., linoleic and linolenic acid, gamma-linoleic acid, eicosapentaenoic acid and docosahexaenoic acid and derivatives, esters, salts and mixtures thereof.

In an embodiment of the present invention, the active agent is a self-tanning agent, such as dihydroxyacetone.

In an embodiment of the present invention, the active agent is an agent, capable of treating hyperhidrosis. Suitable hyperhidrosis agents include but are not limited to anticholinergic drugs, boric acid, tannic acid, resorcinol, potassium permanganate, formaldehyde, glutaraldehyde, methenamine, a Lewis acid, aluminum chloride, aluminum chlorohydrates, zirconium chlorohydrates, aluminum-zirconium-Glycine (AZG) complex, aluminum hydroxybromide, a glycopyrrolate compound, a 5-alpha-reductase inhibitor, finasteride, epristeride, flutamide, spironolactone, saw palmetto extract, cholestan-3-one, a mono- and dicarboxylic acid having 4 to 18 carbon atoms, botulinum toxin, a 5-HT2C receptor antagonist, a 5-HT2C receptor antagonist, ketanserin, ritanserin, mianserin, mesulergine, cyproheptadine, fluoxetine, mirtazapine, olanzapine and ziprasidone.

In an embodiment of the present invention, the active agent is a sunscreen agent. Suitable sunscreen agents include but are not limited to titanium dioxide, zinc oxide, zirconium oxide, iron oxide, p-aminobenzoic acid and its derivatives (ethyl, isobutyl, glyceryl esters; p-dimethylaminobenzoic acid); anthranilic acid derivatives (i.e., o-amino-benzoates, methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid, o- and p-hydroxybiphenyldisulfonates, coumarin derivatives (7-hydroxy, 7-methyl, 3-phenyl), diazoles (2-acetyl-3-bromoindazole, phenyl benzoxazole, methyl naphthoxazole, quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

In an embodiment of the present invention, the active agent is a figure-forming agent and an agent, capable of treating cellulite. Suitable such agents include but are not limited to baldderwack extract, butcher's, broom, cayenne, dandelion, red clover, ginkgo biloba, horse chestnut, witch hazel and borage oil, caffeic acid, nicotinic acid, theophiline and pentoxyphilline and salts and derivatives thereof.

Several disorders of the skin, body cavity or mucosal surface (e.g., the mucosa or the cavity of the nose, mouth, eye, ear, vagina or rectum) involve a combination of etiological factors. For example, fungal and bacterial infections and that are inflamed and have symptoms of redness and/or itching warrant therapy that combines an anti-infective agent and an anti-inflammatory agent. Thus, in several cases, combining at least two active agents that treat different etiological factors results in a synergistic effect and consequently higher success rate of the treatment.

In certain cases, the composition contains two active agents, where each of the active agents require a different pH environment in order to remain stable. For example, corticosteroids are typically stable at acidic pH values (they have a maximum stability at a pH of about 4-6) and of vitamin D analogues are typically stable at basic pH values (they have a maximum stability at pH values above about 8). In order to circumvent the problem of instability it is preferred that the composition is substantially non-aqueous or preferably waterless. The term "substantially non-aqueous" is intended to indicate that the composition has a water content below about 5%, preferably below about 2%, such as below about 1.5%. The formulation can then be modulated by a modulating agent addative that provides, for example, an artificial pH closer to the more sensitive of the two sensitive actives or alternatively closer to the more pH sensitive of the two actives. On a pragmatic level formulating the composition with an artificial pH close to that of skin may be an advantage.

In one or more embodiments the active pharmaceutical or cosmetic agent is an agent which is sensitive to pH such that it is more stable at a certain pH or pH range and tends to react or break down or isomerise at a different pH or pH range. In a preferred embodiment the active agent includes the following non limiting examples: steroids (most are stable at acidic ph of about 4.5); antibiotics, such as tetracycline's which are stable at acidic ph (e.g. oxytetracycline, clindamycin,); penicillinic and cephalosporinic antibiotics, (such as, ampicillin, benzylpenicillin, carbenicillin, cephydroxil, cefotaxime, cephalotin, and cephradine); triamcinolone; nystatin (stable at about ph 7.0); sulfacetamide; and amphotericin; vitamins are generally ph sensitive and examples are ascorbic acid which is stable in slightly acidic conditions and vitamin D analogues that are stable at basic pH, and nicotine amide; NSAID's such as aspirin and indomethacin; atropine; piloarpine; procaine amide; aztrenam; barbiturates; captopril nucletide derivatives such as cytarabineepinephrine; parabens such as ethylparaben methlparaben; anticancer agents such as fluorouracil and iodoxuridine; morphine analgesic; prostaglandins and thiamine HCl.

Fields of Applications

The foamable carrier of the present invention is suitable for treating any infected surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

By selecting a suitable active agent, or a combination of at least two active agents, the foamable composition of the present invention is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition of the present invention is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present invention, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment of the present invention, the composition is useful for the treatment of wound, ulcer and burn. This use is particularly important since the composition of the present invention creates a thin, semi-occlusive layer, which coats the damaged tissue, while allowing exudates to be released from the tissue.

The composition of the present invention is also suitable for administering a hormone to the skin or to a mucosal membrane or to a body cavity, in order to deliver the hormone into the tissue of the target organ, in any disorder that responds to treatment with a hormone.

In light of the hygroscopic nature of the water-free composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

Substantially Alcohol-Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

Shakability

'Shakability' means that the composition contains some or sufficient flow to allow the composition to be mixed or remixed on shaking. That is, it has fluid or semi fluid properties. In some very limited cases it may still be possible to have a foamable composition which is flowable but not apparently shakable.

Breakability

A breakable foam is thermally stable or substantially so, yet breaks under sheer force. The breakable foam of the present invention is not "quick breaking", i.e., it does not readily collapse upon exposure to body temperature environment. Sheer-force breakability of the foam is clearly advantageous over thermally induced breakability, (due to, for example, the presence of alcohol) since it allows comfortable application and well directed administration to the target area.

Chemical Instability and Stability

By chemical instability of one or more active agents is meant that at least one of the one or more active agents is susceptible to one or more of inter alia reaction, breakdown, ionization or oxidation or the rate thereof is increased when incorporated into a pharmaceutical or cosmetic carrier that is non aqueous or substantially non aqueous and not comprising a modulating agent.

Conversely by chemical stability of one or more active agents is meant that at least one of the one or more active agents is less susceptible to one or more of inter alia reaction, breakdown, ionization or oxidation or the rate thereof is impeded when incorporated into a pharmaceutical or cosmetic carrier that is non aqueous or substantially non aqueous and comprising a modulating agent.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. patent application Ser. No. 11/732,547, filed on Apr. 4, 2007, entitled ANTI-INFECTION AUGMENTATION OF FOAMABLE COMPOSITIONS AND KIT AND USES THEREOF; U.S. Provisional Patent Application No. 60/789,186, filed on Apr. 4, 2006, KERATOLYTIC ANTIFUNGAL FOAM; U.S. Provisional Patent Application No. 0/815948, filed on Jun. 23, 2006, entitled FOAMABLE COMPOSITIONS COMPRISING A CALCIUM CHANNEL BLOCKER, A CHOLINERGIC AGENT AND A NITRIC OXIDE DONOR; U.S. Provisional Patent Application No. 60/818,634, filed on Jul. 5, 2006, entitled DICARBOXYLIC ACID FOAMABLE VEHICLE AND PHARMACEUTICAL COMPOSITIONS THEREOF; U.S. Provisional Patent Application No. 60/843,140, filed on Sep. 8, 2006, entitled FOAMABLE VEHICLE AND VITAMIN PHARMACEUTICAL COMPOSITIONS THEREOF, all of which are incorporated herein by reference in their entirety. More particularly any of the active ingredients; the solvents; the surfactants; foam adjuvants; polymeric agents, penetration enhancers; preservatives, humectants; moisturizers; and other excipients as well as the propellants listed therein can be applied herein and are incorporated by reference.

The invention is described with reference to the following examples. This invention is not limited to these examples and experiments. Many variations will suggest themselves and are within the full intended scope of the appended claims.

Methodology

The formulas of the present invention may be made in the following general way with appropriate adjustments for each formulation as will be appreciated by someone skilled in the art. Polymers, if any, are mixed, swelled and solubilized in the waterless medium, when necessary, with appropriate heat until it forms a clear solution. Stabilizing surfactants added usually with heat, until a homogeneous mixture is obtained, the mixture is then allowed to cool. The remainder of the ingredients, are then added with mixing until they have dissolved in the medium. The active agent is usually added at the end once the modulating agent has been incorporated. For foam the canisters are then filled with the above waterless formula, sealed and crimped with a valve and pressurized with the propellant.

A general procedure for preparing foamable compositions is set out in WO 2004/037225, which is incorporated herein by reference.

Waterless Foam
1. Dissolve the polymers, if any, in the main solvent with heating or cooling as appropriate for specific polymer. Add the all other ingredients and heat to 75° C. to melt and dissolve the various ingredients.
2. Cool to below 40° C. and add sensitive ingredients with mild mixing.
3. Cool to room temperature.

Note that for substantially waterless foam a small amount of water is added before step 2.

Oily Waterless Foam
1. Mix all ingredients excluding polymers and heat to 75° C. to melt and dissolve and obtain homogeneous mixture.
2. Mix well and cool to below 40° C. and add the polymers, if any, and sensitive ingredients with moderate mixing.
3. Cool to room temperature.

Note that for substantially waterless foam a small amount of water is added before step 2.

Oily Foam with Phospholipids
1. Swell the phospholipids in the main oily solvent under mixing for at least 20 minutes until uniform suspension is obtained.
2. Add all other ingredients excluding polymers and heat to 75° C. to melt and dissolve and obtain homogeneous mixture.
3. Mix well and cool to below 40° C. and add the polymers, if any, and sensitive ingredients with moderate mixing.
4. Cool to room temperature.
5. In case of polymers dissolved or organic solvent, dissolve the polymers in the solvent with heating or cooling as appropriate for specific polymer and add to the oily mixture under vigorous mixing at ~40° C.

Note that for substantially waterless foam a small amount of water is added step 5.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Canisters Filling and Crimping

Each aerosol canister is filled with PFF and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing
Propellant Filling

Pressurizing is carried out using a hydrocarbon gas or gas mixture. Canisters are filled and then warmed for 30 sec in a warm bath at 50° C. and well shaken immediately thereafter.

Closure Integrity Test.

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Tests

By way of non limiting example the objectives of hardness, collapse time and FTC stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can affect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 min.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000CP, the viscosity at 1 RPM may be measured, although the figures are of a higher magnitude.

Conductance

The conductance meter is calibrated. The electrode is inserted into a sufficient volume of composition and the conductance reading is recorded. Measurements with foamable compositions are made prior to addition of propellant.

FTC (Freeze Thaw Cycles)

To check the foam appearance under extreme conditions of repeated cycles of cooling, heating, (first cycle) cooling, heating (second cycle) etc., commencing with −100° C. (24 hours) followed by +400° C. (24 hours) measuring the appearance and again repeating the cycle for up to three times.

Focus Group

Five healthy volunteers selected at random were give a sample of foam formulation and applied it to the skin on their forearm and were asked to complete a questionnaire.

Chemical Stability

The amount of active agent present is analysed in foam expelled from various pressurized canisters containing foam formulations using HPLC. Analysis is carried out at zero time and at appropriate time intervals thereafter. The canisters are stored in controlled temperature incubators at 5 C, at 25 C, at, 40 C and at 50 C. At appropriate time intervals canisters are removed and the amount of active agent in the foam sample is measured.

Analysis

About 1 g of foam or pre-foam formulation is dissolved in 0.1% acetic acid in methanol (diluent), to which internal standard (1S) solution is added. BMV, BMV-21 and are extracted by heating, cooling and centrifugation of the sample solution. The clear layer is analyzed by HPLC using a C-18 column; elution is performed with a mobile phase containing acetonitrile:water 55:45. The content of BMV and BMV-21 is calculated using the respective peak area ratio against average peak area ratio of BMV standard (0.2 mg/mL) to the IS present in the standard solution at the same concentration as in samples. The details of the method conditions are as follows: the column type is Acquity BEH C-18, 1.7 μm, 50×2.1 mm in 40° C., the flow is 0.5 mL/min, the detector: UV, at 254 nm injection volume is 4 μL.; the diluents is 0.1% acetic acid in water:acetonitrile, 45:55 (v/v) and the mobile phase content is water:acetonitrile, 45:55 (v/v). The run time is 4 min.

The method can be carried out by HPLC using a different but appropriate column of the same type.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10MP) equipped with Sigma Macro Lens (ref: APO MACRO 150 mm F2.8 EX DG HSM). Pictures obtained are cropped to keep a squared region of 400 pixels×400 pixels.

Stock Compositions

Non-limiting examples of how stock solutions are made up with and without API are illustrated. Other stock solutions may be made using the same methodology by simply varying adding or omitting ingredients as would be appreciated by one of the ordinary skills in the art.

EXAMPLES

The invention is described with reference to the following examples. For the purpose of the Examples below it was sufficient to apply a vacuum only at the crimping stage although for long term stability preferably any vacuum should be applied during manufacture as well at a sufficient pressure so that any oxygen remaining in the formulation is virtually negligible. This invention is not limited to these examples and experiments. Many variations will suggest themselves and are within the full intended scope of the appended claims.

Example 1

A Waterless Steroid Foamable Composition with Out a Modulating Agent

The components of this waterless foamable composition and the results of the measurements of the stability of the active agent are set our below:

| | Material chemical name | % W/W |
|---|---|---|
| | Propylene glycol | 31.60 |
| | Glycerin anhydrous | 37.40 |
| | Stearyl alcohol | 1.00 |
| | Hydroxypropyl cellulose | 1.50 |
| | Laureth-4 | 2.00 |
| | Glyceryl Monostearate/PEG 100 Stearate | 1.50 |
| Stock solution | Betamethasone 17-Valerate | 0.12 |
| | Propylene glycol | 24.88 |
| | Total | 100.00 |

| Time point | % of BMV-17 (w/w) | % BMV-21 of BMV 0.12% (w/w) |
|---|---|---|
| ACCELORATED CHEMICAL STABILITY TESTS FOR FOAM | | |
| ZT | 0.120 | 0.32 |
| 2 weeks, 40° C. | 0.079 | 33.98 |
| 1 month, 40° C. | 0.066 | 40.07 |

| ACCELERATED CHEMICAL STABILITY TESTS FOR PRE-FOAM FORMULATION | | |
| --- | --- | --- |
| ZT | 0.120 | 0.63 |
| 2 weeks, 50° C. | 0.059 | 51.33 |
| 1 month, 50° C. | 0.036 | 41.77 |

Comment: Significant amounts of BMV-17 break down into its unwanted isomer BMV-21 within a relatively short period of time in the absence of a Modulating agent. For foam, a propellant, which is a mixture of propane, butane and isobutane was added at 8% by weight of the total composition.

Example 2

Waterless Steroid Foamable Compositions where the Modulating Agent is a Citric Acid/Sodium Citrate buffer The components of these waterless foamable compositions and the results of measurements of the properties of the resultant foams and of the stability of the active agent are set our below:

a) At 0.1% Sodium Citrate

| Material chemical name | | % W/W |
| --- | --- | --- |
| Propylene glycol | | 31.00 |
| Glycerin anhydrous | | 37.40 |
| Stearyl alcohol | | 1.00 |
| Hydroxypropyl cellulose | | 1.50 |
| Laureth-4 | | 2.00 |
| Glyceryl Monostearate/PEG 100 Stearate | | 1.50 |
| Citric acid | | 0.50 |
| Sodium citrate | | 0.10 |
| Stock solution | Betamethasone 17-Valerate | 0.12 |
| | Propylene glycol | 24.88 |
| Total | | 100.00 |
| Results | | |
| Quality | | good |
| Color | | white |
| Odor | | No odor |
| Hardness [g] | | 66.98 |
| Collapse time at 36° C. [sec] | | >300 |

| Time point | % of BMV-17 (w/w) | % BMV-21 of BMV 0.12% (w/w) |
| --- | --- | --- |
| ACCELERATED CHEMICAL STABILITY TESTS FOR FOAM | | |
| ZT | 0.117 | 0.90 |
| 2 weeks, 40° C. | 0.118 | 0.42 |
| 1 month, 40° C. | 0.111 | 0.47 |
| ACCELERATED CHEMICAL STABILITY TESTS FOR PRE-FOAM FORMULATION | | |
| ZT | 0.118 | 0.95 |
| 2 weeks, 50° C. | 0.115 | 1.34 |
| 1 month, 50° C. | 0.109 | 1.40 |

Comment: In the presence of a modulating agent BMV-17 does not significantly break down into its unwanted isomer BMV-21 over a period of a month of accelerated stability tests indicating that the formula will be stable in the long term. The presence of a classical buffer in the waterless composition of the present invention is effective in a non classical way in providing a chemically stable environment for the active agent. It will be noted that the formulation produced good quality breakable foam with typical physical parameters of a polar waterless foam. For foam, a propellant, which is a mixture of propane, butane and isobutane was added at 8% by weight of the total composition.

b) At 0.4% Sodium Citrate

| Material chemical name | | % W/W |
| --- | --- | --- |
| Propylene glycol | | 31.00 |
| Glycerin anhydrous | | 37.40 |
| Stearyl alcohol | | 1.00 |
| Hydroxypropyl cellulose | | 1.50 |
| Laureth-4 | | 2.00 |
| Glyceryl Monostearate/PEG 100 Stearate | | 1.50 |
| Citric acid | | 0.50 |
| Sodium citrate | | 0.40 |
| Stock solution | Betamethasone 17-Valerate | 0.12 |
| | Propylene glycol | 24.88 |
| Total | | 100.00 |

| Time point | % of BMV-17 (w/w) | % BMV-21 of BMV 0.12% (w/w) |
| --- | --- | --- |
| CHEMICAL STABILITY TESTS FOR FOAM | | |
| ZT | 0.122 | 0.00 |
| 2 weeks, 40° C. | 0.117 | 0.82 |
| 1 month, 40° C. | 0.117 | 1.89 |
| CHEMICAL STABILITY TESTS FOR PRE-FOAM FORMULATION | | |
| ZT | 0.122 | 0.00 |
| 2 weeks, 50° C. | 0.114 | 3.33 |
| 1 month, 50° C. | 0.109 | 8.44 |

Comment: In the presence of a modulating agent BMV-17 does not significantly break down into its unwanted isomer BMV-21 over a period of two weeks of accelerated stability study. After a month minimal breakdown is seen indicating that the lower level of 0.1% w/w sodium citrate is preferable. For foam, a propellant, which is a mixture of propane, butane and isobutane was added at 8% by weight of the total composition.

Example 3

A Waterless Steroid Foamable Composition where the Modulating Agent is Stearic Acid The components of this waterless foamable composition and the results of measurement of the stability of the active agent are set our below:

| Material chemical name | | % W/W |
| --- | --- | --- |
| Propylene glycol | | 30.60 |
| Glycerin anhydrous | | 37.40 |
| Stearyl alcohol | | 1.00 |
| Hydroxypropyl cellulose | | 1.50 |
| Laureth-4 | | 2.00 |
| Glyceryl Monostearate/PEG 100 Stearate | | 1.50 |
| Stearic acid | | 1.00 |
| Stock solution | Betamethasone 17-Valerate | 0.12 |
| | Propylene glycol | 24.88 |
| Total | | 100.00 |

| Time point | % of BMV-17 (w/w) | % BMV-21 of BMV 0.12% (w/w) |
| --- | --- | --- |

STABILITY TESTS FOR FOAM

| | | |
|---|---|---|
| ZT | 0.113 | 1.32 |
| 2 weeks, 40° C. | 0.112 | 2.20 |
| 1 month, 40° C. | 0.096 | 2.41 |

STABILITY TESTS FOR PRE-FOAM FORMULATION

| | | |
|---|---|---|
| ZT | 0.115 | 0.73 |
| 2 weeks, 50° C. | 0.109 | 4.80 |
| 1 month, 50° C. | 0.093 | 5.78 |

Comment: In the presence of a modulating agent BMV-17 does not significantly break down into its unwanted isomer BMV-21 over a period of two weeks of accelerated stability. After a month only very minimal additional breakdown is seen indicating that stability is likely to be improved with a higher level of Stearic Acid and that the formula will be stable in the long term. For foam, a propellant, which is a mixture of propane, butane and isobutane was added at 8% by weight of the total composition.

Example-4

A Waterless Steroid Foamable Composition with a Penetration Enhancer DMI in the absence of an added Modulating Agent The components of this waterless foamable composition and the results of measurements of the properties of the resultant foam and of the stability of the active agent are set our below:

a) Composition and Physical Results

| Ingredient | % w/w |
|---|---|
| Stearyl alcohol | 1.00 |
| Laureth-4 | 2.00 |
| Glyceryl stearate & PEG-100 stearate | 1.50 |
| Propylene glycol | 45.88 |
| Hydroxypropyl cellulose | 1.50 |
| Glycerin anhydrous | 33.00 |
| Dimethyl isosorbide | 15.00 |
| Betamethasone 17-valerate | 0.12 |
| Total: | 100.00 |
| Propellant: Mixture of propane, butane, isobutane* | 8.00 |
| Results | |
| Quality | good |
| Color | white |
| Odor | no odor |
| Density [g/mL] | 0.089 |
| Hardness [g] | 94.610 |
| Expansion time [sec] | 90 sec |
| Collapse time at 36° C. [sec] | >300 | b) Betamethasone Valerate Waterless Results Showing Stability at Three Months

| | T-0 | T-3 | Temp |
|---|---|---|---|
| (w/w)% | 0.117 | 0.113 | 25 C. |
| | 0.117 | 0.113 | 40 C. |
| Percentage of original | 100.000 | 96.581 | 25 C. |
| | 100.000 | 96.581 | 40 C. |

Comment: The above formula, in retrospect, was noted to have contained significant levels of residues of fatty acids, which were present in the raw materials. Nevertheless, the active ingredient did not significantly break down over a period of three months of accelerated stability indicating that the formula will be stable in the long term. Thus, the presence of acidic residues unexpectedly contributed to the stability of the active ingredient and it is postulated that the stabilizing effect in the above formula is a combination of the absence of water coupled with the presence of acidic residues in the formulation and weakly acidic properties of the surfactants. In contrast the formula of Example 1 utilizing pure grade raw materials with practically no acidic residues undergoes a relatively rapid and serious breakdown.

Example 5

A Waterless Vitamin D3 Derivative Foamable Composition where the Modulating Agent is Triethoanolamine The components of these waterless foamable compositions and the results of measurements of the properties of the resultant foams and of the stability of the active agent are set our below:

A. Where the waterless solvent is a combination of two polyethylene glycols:

| Ingredient name (INCI, CTFA) | Concentration (% w/w) |
|---|---|
| Calcipotriol | 0.005 |
| Polyethylene glycol 400 | 65 |
| Polyethylene glycol 200 | 32.925 |
| Hydroxypropyl cellulose | 0.5 |
| Steareth-2 | 1.5 |
| Triethanolamine | 0.07 |

Results T-0

| | |
|---|---|
| Quality | Good |
| Color | White |
| Odor | No odor |
| Density | 0.096 |

B. Where the waterless solvent is a combination of two polyethylene glycols and propylene glycol:

| Ingredient name (INCI, CTFA) | Concentration (% w/w) |
|---|---|
| Calcipotriol | 0.005 |
| Polyethylene glycol 400 | 65 |
| Polyethylene glycol 200 | 27 |

-continued

| Ingredient name (INCI, CTFA) | Concentration (% w/w) |
|---|---|
| Propylene glycol | 4.895 |
| Hydroxypropyl cellulose | 1.5 |
| Steareth-2 | 1.5 |
| Triethanolamine | 0.1 |
| Results T-0 | |
| Quality | Good |
| Color | White |
| Odor | No odor |
| Density | 0.096 |

C. Where the waterless solvent is propylene glycol:

| Ingredient name (INCI, CTFA) | Concentration (% w/w) |
|---|---|
| Calcipotriol | 0.005 |
| Propylene glycol | 87.895 |
| Stearyl alcohol | 2 |
| Hydroxypropyl cellulose | 2 |
| Laureth-4 | 2 |
| Glyceryl monostearate | 2 |
| Ceteareth-20 | 1 |
| PPG-15 Stearyl ether | 3 |
| Triethanolamine | 0.1 |

| Ingredient name (INCI, CTFA) | Concentration (% w/w) |
|---|---|
| Results T-0 | |
| Quality | Good |
| Color | White |
| Odor | No odor |
| Density | 0.064 |

Comment: The above three formulations demonstrate waterless breakable foams of good quality in which the active ingredient is sensitive to the presence of water and light and is stabilized by the absence of water coupled with the presence of a modulating agent triethanolamine. As will be appreciated from the results the physical characteristics are little varied following variations in the waterless solvent. Moreover, it can be seen that waterless foamable pharmaceutical and cosmetic compositions of good quality can be achieved with minimal ingredients comprising a waterless solvent, a surfactant, a polymeric agent, a propellant and an effective amount of an active ingredient. For foam, a propellant, which is a mixture of propane, butane and isobutane was added at 8% by weight of the total composition. In the above examples the propellant was AP70.

Example 6

A Waterless Ascorbic Acid Foamable Composition

The components of these waterless foamable compositions and the results of measurements of the properties of the resultant foam and of the stability of the active agent are set our below:

| Ingredient name (INCI, CTFA) | 1 | 2 | 3 | 4 |
|---|---|---|---|---|
| Propylene glycol | 88.00 | 78.00 | 46.00 | 78.00 |
| Glycerin anhydrous | | | 33.00 | 10.00 |
| Stearyl Alcohol | 2.00 | 1.00 | 1.00 | 2.00 |
| Hydroxypropyl Cellulose | 2.00 | 1.50 | 1.50 | 2.00 |
| Laureth-4 | 2.00 | 2.00 | 2.00 | 2.00 |
| Glyceyl Monostearate/ PEG 100 Stearate | | | 1.50 | |
| GMS NE | 2.00 | 1.00 | | 2.00 |
| Macrogol Cetostearyl ether | 1.00 | 1.50 | | 1.00 |
| PPG-15 stearyl ether | 3.00 | | | 3.00 |
| Dimethyl isosorbide | | 15.00 | 15.00 | |
| total | 100.00 | 100.00 | 100.00 | 100.00 |
| Ingredient name (INCI, CTFA) | % w/w | % w/w | % w/w | % w/w |
| Stock Gel Phase preparation | 95.00 | 95.00 | 95.00 | 95.00 |
| Ascorbic Acid | 5.00 | 5.00 | 5.00 | 5.00 |
| Propellant | 8.00 | 8.00 | 8.00 | 8.00 |
| RESULTS | | | | |
| FOAM QUALITY | GOOD | GOOD | GOOD | GOOD |
| COLOR | WHITE | WHITE | WHITE | WHITE |
| ODOR | NO ODOR | ODOR | NO ODOR | ODOR |
| SHAKABILITY | MODERATE | MODERATE | MODERATE | MODERATE |
| DENSITY | 0.08 | 0.09 | 0.10 | 0.08 |
| COLLAPSE TIME | >300 | >300 | >300 | >300 |
| HARDNESS | Not measured | Not measured | 52.25 | 36.04 |

Comments; the above formulations demonstrate the preparation of good quality foam containing ascorbic acid as active ingredient is not significantly influenced by the addition of a secondary solvent or the presence of a penetration enhancer Dimethyl isosorbide. To an extent ascorbic acid may act as its own modulating agent. Another modulating agent can be used to modify the artificial pH to be of the order of the pH at which ascorbic acid is most stable.

Example 7

Waterless Lidocaine HCl-Prilocaine Base Foamable Composition

The components of this waterless foamable composition and the results of measurements of the properties of the resultant foam and of the stability of the active agent are set our below:

| Material chemical name | % W/W |
|---|---|
| Propylene glycol | 46.00 |
| Hydroxypropylcellulose EF | 1.50 |
| Stearyl alcohol | 1.00 |
| Laureth-4 | 2.00 |
| Glyceryl Stearate (and) PEG-100 Stearate | 1.50 |
| Lidocaine HCl | 2.50 |
| Prilocaine base | 2.50 |
| Glycerin anhydrous | 28.00 |
| Dimethyl isosorbide | 15.00 |
| Total: | 100.00 |
| Mixture of Propane/Butane/Isobutane | 8.00 |
| RESULTS | |
| FOAM QUALITY | GOOD |
| COLOR | WHITE |
| ODOR | NO ODOR |
| SHAKABILITY | GOOD |
| COLLAPSE TIME | >300 |
| HARDNESS | 85.88 |

Comments; the above formulations demonstrate the preparation of good quality foam containing anesthetics as active ingredient is not significantly influenced by the addition of a secondary solvent or the presence of a penetration enhancer Dimethyl isosorbide. To an extent lidocaine and prilocaine may act as its own modulating agent. Another modulating agent can be used to modify the artificial pH to be of the order of the pH at which lidocaine and prilocaine are respectively most stable.

Example 8

A Minimal Waterless Carrier

The components of this waterless foamable composition and the results of measurements of the properties of the resultant foam and of the stability of the active agent are set our below:

| Material chemical name | % W/W |
|---|---|
| Propylene glycol | 96.00 |
| Hydroxypropyl cellulose | 2.00 |
| Steareth 2 | 2.00 |
| Total | 100.00 |
| Results | |
| quality | excellent |
| color | white |
| odor | no odor |

Comment: this carrier produces an excellent foam. Addition of an active agent such as active steroids in low concentrations of the order of 0.01 to 0.5% for example BMV at 0.12% w/w. together with a modulating agent should have minimal effect on the physical characteristics of the resultant foam.

Example 9

Demonstration of Excellent Minimal Foams Produced with Two Different Surfactants Steareth 2 and Montanov 68 (Cetearyl Alcohol and Cetearyl Glucoside)

The components of these waterless foamable compositions and the results of measurements of the properties of the resultant foams and of the stability of the active agent are set our below:

| Material chemical name | % W/W | % W/W | % W/W |
|---|---|---|---|
| Propylene glycol | 96.00 | 95.28 | 97.50 |
| Hydroxypropyl cellulose | 2.00 | 2.00 | 0.50 |
| Steareth 2 | 2.00 | 2.00 | |
| Citric acid | | 0.50 | |
| Sodium citrate | | 0.10 | |
| Cetearyl Glucoside and Cetearyl Alcohol | | | 2.00 |
| Betamethasone 17-Valerate | | 0.12 | |
| Results | | | |
| Total | 100.00 | 100.00 | 100.00 |
| quality | excellent | excellent | excellent |
| color | white | white | white |
| odor | no odor | no odor | no odor |
| shakability | shakable | shakable | shakable |

Comments; the above formulations demonstrate the preparation of excellent quality foams using two different non ionic surfactants and that the addition of buffer or active agent has no significant effect on foam quality. For foam, a propellant, which is a mixture of propane, butane and isobutane was added at 8% by weight of the total composition.

Example 10

Examples of Foams Containing a Steroid Active Agent with Carbomer (Synthetic High Molecular Weight Crosslinked Polymers of Acrylic Acid) as the Polymeric Agent The components of these waterless foamable compositions and the results of measurements of the properties of the resultant foams and of the stability of the active agent are set our below:

| Material chemical name | % W/W | % W/W | % W/W | % W/W | % W/W | % W/W | | |
|---|---|---|---|---|---|---|---|---|
| Propylene glycol | 97.50 | 97.45 | 97.60 | 97.575 | 97.50 | 97.45 | 97.60 | 97.60 |
| Steareth 2 | 2.00 | 2.00 | 2.00 | 2.00 | | | | |
| Carbomer 934 | 0.50 | 0.50 | 0.20 | 0.20 | 0.50 | 0.50 | 0.20 | 0.20 |
| triethanolamine | | | 0.20 | 0.20 | | | 0.20 | 0.20 |
| Cetearyl Glucoside and Cetearyl Alcohol | | | | | 2.00 | 2.00 | | |
| Methyl glucose sesquistearate | | | | | | | 2.00 | |
| Span 60 | | | | | | | | 2.00 |
| Clobetasol propionate | | 0.05 | | | | 0.05 | | |
| Flucinolone acetonide | | | | 0.025 | | | | |
| Total | 100.00 | 100.00 | 100.00 | 100.00 | 100.00 | 100.00 | | |

Results

| Quality E = excellent G = good | .E | E | E | E | E | eE | .G | .G |
|---|---|---|---|---|---|---|---|---|
| Color | White | white | White | white | white | white | white | white |
| Odor | no odor | no odor | no odor | no odor | no odor | no odor | no odor | no odor |
| Shakability | yes. | yes | .yes | .yes | .yes | .yes | .yes | yes |

Comments; the above formulations demonstrate the preparation of excellent quality foam using Carbomer (synthetic high molecular weight crosslinked polymers of acrylic acid) Carbomer is acidic in nature and can stabilize an active agent atone or in combination with an organic base such as triethanolamine. For foam, a propellant, which is a mixture of propane, butane and isobutane was added at 8% by weight of the total composition.

Example 10

Chemical Stability a) Stock Solutions 1 and 2

| chemical name | Stock 1 | Stock 2 |
|---|---|---|
| Stearyl alcohol | 1.00 | |
| Laureth-4 | 2.00 | |
| Glyceryl stearate & PEG-100 stearate | 1.50 | |
| Propylene glycol | 36.00 | 9.88 |
| Hydroxypropyl cellulose | 1.50 | |
| Glycerin anhydrous | 33.00 | |
| Steareth 2 | | |
| Dimethyl isosorbide | 15.00 | |
| Betamethasone 17-valerate | | 0.12 |
| Total | 90.00 | 10.00 |

Comments: 90 mls of Stock 1 was combined with 10 mls of stock 2 to produce the basic formulations of 3, 4 and 5 below to which only a few drops of acidic Modulating Agent was added as indicated below.

b) 46% Waterless PG Formulations with BMV with different acidic Modulating Agents including one where the modulating agent is a second active agent

| chemical name | 003 | 004 | 005 |
|---|---|---|---|
| Stearyl alcohol | 1.00 | 1.00 | 1.00 |
| Laureth-4 | 2.00 | 2.00 | 2.00 |
| Glyceryl stearate & PEG-100 stearate | 1.50 | 1.50 | 1.50 |
| Propylene glycol (PG) | 45.88 | 45.88 | 45.88 |
| Hydroxypropyl cellulose | 1.50 | 1.50 | 1.50 |
| Glycerin anhydrous | 33.00 | 33.00 | 33.00 |
| Dimethyl isosorbide | 15.00 | 15.00 | 15.00 |
| Betamethasone 17-valerate (BMV) | 0.12 | 0.12 | 0.12 |
| Lactic acid* | To ph 4-4.5 | | |
| L-Glutamic acid* | | To ph 4-4.5 | |
| Azelaic acid* | | | To ph 4-4.5 |
| Total | 100.00 | 100.00 | 100.00 |
| Propellant (AP-70) | 8.00 | 8.00 | 8.00 |
| foam quality | Good | Good | Good |
| Color | White | White | White |
| Odor | No | No | No |
| assay (T-0) FOAM | 0.1183 | 0.1183 | 0.1177 |
| assay (T-1M) 5 C FOAM | 0.1180 | 0.1182 | 0.1181 |
| assay (T-1M) 25 C FOAM | 0.1175 | 0.1185 | 0.1180 |
| assay (T-1M) 40 C FOAM | 0.1158 | 0.1156 | 0.1165 |
| assay (T-1M) 50 C PFF | 0.1148 | 0.1165 | 0.1158 |

*Only a few drops were required to achieve the required pH, which was sufficient to provide a stabilizing effect.

Comments: All the modulated formulations provided foam of good quality, in which the active agent BMV was shown to be stable to degradation in a wide range of temperature from 5 C to 50 C over a period of a month. The pre foam formulation was also found to be stable for 1 month.

Example 11

EDTA

| chemical name | 006 | 007 |
|---|---|---|
| Propylene glycol | 97.90 | 98.90 |
| Hydroxypropyl cellulose |  | 1.00 |
| Steareth 2 | 2.00 |  |
| EDTA | 0.10 | 0.10 |
| Total | 100.00 | 100.00 |
| Propellant (AP-70) | 8.00 | 8.00 |
| foam quality | Good | Good |
| Color | White | White |
| Odor | No | No |

Comments: The formulation is modulated with EDTA and provided foam of good quality.

Example 12

Lysine

| chemical name | 008 |
|---|---|
| Propylene glycol | 98.00 |
| Steareth 2 | 2.00 |
| L-lysine | To ph 7 |
| Total | 100.00 |
| Propellant (AP-70) | 8.00 |
| foam quality | Good |
| Color | White |
| Odor | No |

Comments: The formulation modulated with a basic Modulating Agent provided foam of good quality,

Example 13

BMV a) Minimum Ingredients;

| chemical name | 009 | 010 |
|---|---|---|
| Stearyl alcohol | 1.00 |  |
| Laureth-4 | 2.00 |  |
| Glyceryl stearate & PEG-100 stearate | 1.50 |  |
| Propylene glycol | 45.88 | 97.88 |
| Hydroxypropyl cellulose | 1.50 |  |
| Glycerin anhydrous | 33.00 |  |
| Steareth 2 |  | 2.00 |
| Dimethyl isosorbide | 15.00 |  |
| Betamethasone 17-valerate | 0.12 | 0.12 |
| Total | 100.00 | 100.00 |
| Propellant (AP-70) | 8.00 | 8.00 |
| Viscosity | 4990.94 | 3711.21 |
| foam quality | Good | Good |
| Color | White | White |
| Odor | No | No |
| Density | 0.07 | 0.05 |
| Collapse time | >300/G | .300/G |
| BUBBLE SIZE (μm) | 150 | 139 |
| BUBBLE SIZE (above 500 μm) | 3.4 | 3.7 |
| Conductivity | 0.41 μS | 0 μS |
| Conductivity (+1 drop of Lactic acid) | 0.55 μS | 0.05 μS |

Comments: It is surprisingly possible to produce good quality foam without a polymeric agent. Nevertheless, the presence of polymeric agent can be not only helpful but important and sometimes critical for foam stability. Prophetically, small amounts of modulating agent may be added to the formulations without significant effect on the resultant foam. Remarkably, despite that these formulations are waterless, nevertheless a single drop of lactic acid results in a significant increase of conductivity. Also as can be seen herein the use of modulating agents is just as applicable for formulations with minimal ingredients as it is with complex formulations, perhaps the main difference being that with complex formulations the there are more ingredients which increases the risk that one may contain a small impurity that can result in destabilization of the active ingredient. On the other hand formulations with few ingredients may have higher levels of a destabilizing impurity merely because say 90% of the formulation comprises an ingredient having the impurity albeit at low levels. Either way the importance of the presence of a small amount of modulating agent in a waterless formulation cannot be ignored or underestimated.

b) Focus Group (5)

|  |  | Sum | Avg | STDV | TOTAL |
|---|---|---|---|---|---|
| MAPG009P | ease of application | 21 | 4.2 | 0.45 | 180 |
|  | foam Texture | 20 | 4 | 0.00 |  |
|  | foam stability on hand | 24 | 4.8 | 0.45 |  |
|  | absorbance (1 min.) | 17 | 3.4 | 0.55 |  |
|  | spreadability | 21 | 4.2 | 0.45 |  |
|  | greasy feeling (after 1-2 min.) | 16 | 3.2 | 1.10 |  |
|  | shiny look (after 1-2 min.) | 18 | 3.6 | 1.14 |  |
|  | stickiness (after 1-2 min.) | 17 | 3.4 | 1.14 |  |
|  | odor | 10 | 2 | 1.73 |  |
|  | total satisfaction | 16 | 3.2 | 1.10 |  |
| MAPG010P | ease of application | 21 | 4.2 | 0.84 | 201 |
|  | foam Texture | 20 | 4 | 0.71 |  |
|  | foam stability on hand | 22 | 4.4 | 0.55 |  |
|  | absorbance (1 min.) | 19 | 3.8 | 1.10 |  |
|  | spreadability | 21 | 4.2 | 0.84 |  |
|  | greasy feeling (after 1-2 min.) | 19 | 3.8 | 1.30 |  |
|  | shiny look (after 1-2 min.) | 18 | 3.6 | 1.14 |  |
|  | stickiness (after 1-2 min.) | 18 | 3.6 | 1.14 |  |
|  | odor | 22 | 4.4 | 0.55 |  |
|  | total satisfaction | 21 | 4.2 | 0.84 |  |

Comments: The total satisfaction was surprisingly found to be significantly greater with the formulation with minimal ingredients.

Example 14

Carbopol and TEA

| chemical name | 011 | 012 |
|---|---|---|
| Propylene glycol | 99.00 | 97.00 |
| Carbopol 934 | 1.00 | 1.00 |
| Steareth 2 | | 2.00 |
| Triethanolamine (TEA) | neutralization (1 drop) | neutralization (1 drop) |
| Total | 100.00 | 100.00 |
| Propellant (AP-70) | 8.00 | 8.00 |
| Viscosity | | 13485.12 |
| foam quality | P | Good |
| Color | White | White |
| Odor | No | No |
| Density | | 0.08 |
| Collapse time | | >300/G |
| BUBBLE SIZE (μm) | | 72 |
| BUBBLE SIZE (above 500 μm) | | 0.0 |

Comments: The formulation modulated with an acidic polymer and a basic Modulating Agent TEA provided foam of good quality, Carbomer is a cross-linked polymer of acrylic acid with a high molecular weight.

Example 15

Stearic Acid

| chemical name | 013 | 014 |
|---|---|---|
| Stearic acid | 5.00 | 3.00 |
| Isostearic acid | | 3.00 |
| Propylene glycol | 95.00 | 94.00 |
| Total | 100.00 | 100.00 |
| Propellant (AP-70) | 8.00 | 8.00 |
| Viscosity | 1887.60 | |
| foam quality | Good | P |
| Color | White | White |
| Odor | No | No |
| Density | 0.30 | |
| Collapse time | >300/G | |

Comments: Stearic acid a waxy solid acts as a foam adjuvant, thickener and Modulating Agent to produce good quality foam. The selection of Modulating Agent is not per se obvious with a waterless formulation. For example, the addition of isostearic acid results in poor foam presumably but without being bound by any theory suggested due to it being a liquid wax and not having the thickening effect of its closely related counterpart stearic acid plus its isostearic acids asymmetrical shape even though they both are CI8.

What is claimed is:

1. A waterless composition comprising one or more active agents and a carrier for topical delivery of the one or more active agents suitable for stabilizing at least one of said one or more active agents, said carrier comprising:
    a) about 25% to about 98% of at least one polar solvent selected from the group consisting of a polyol, a polyethylene glycol, and combinations thereof;
    b) a modulating agent;
    c) about 0.01% to about 5% by weight of at least one polymeric agent;
    d) a surface active agent; and
    e) a foam adjuvant selected from the group consisting of a fatty alcohol having 15 or more carbons in its carbon chain, a fatty acid having 16 or more carbons in its carbon chain and mixtures of any two or more thereof;
        wherein the at least one active agent is chemically unstable in the carrier in the absence of a modulating agent;
        wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent; and
        wherein if the waterless composition is packaged in an aerosol container and a liquefied or compressed gas propellant is added at a concentration of about 3% to about 25% by weight of the waterless composition, then the composition will be capable upon release from the aerosol container to expand to form a breakable foam that collapses upon application of shear force.

2. The waterless composition of claim 1 further comprising one or more agents that additionally are capable of a function selected from the group consisting of chelating an available metal ion, impeding ionization, and impeding oxidation.

3. The waterless composition of claim 1, wherein the polymeric agent is selected from the group consisting of a locust bean gum, sodium alginate, sodium caseinate, an egg albumin, a gelatin agar, a carrageenin gum, a xanthan gum, a quince seed extract, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, a methylhydroxyethylcellulose, a hydroxyethyl carboxymethyl cellulose, a carboxymethyl cellulose, a cationic cellulose, a PEG 1000, a PEG 4000, a PEG 6000, a PEG 8000 and a carbomer.

4. The waterless composition of claim 3, wherein the polymeric agent is about 0.2% to about 3% by weight of a gelling agent.

5. The waterless composition of claim 1 wherein the modulating agent is between about 5% to about 0.01% by weight of the composition and wherein if the active agent itself has a modulating effect, the amount of active agent used to obtain an effective modulating effect is less than the amount of active agent used to obtain an effective therapeutic effect.

6. The waterless composition of claim 5 wherein the modulating agent is between about 1% to about 0.02% by weight of the composition.

7. The waterless composition of claim 1 wherein the modulating agent is between about 0.6% to about 0.04% by weight of the composition.

8. A foamable waterless composition comprising:
    a. a therapeutically effective concentration of one or more active agents;
    b. a carrier for topical delivery of the one or more active agents suitable for stabilizing at least one of said one or more active agents, comprising i. about 25% to about 98% of at least polar solvent selected from the group consisting of (1) a polyol; and (2) a polyethylene glycol (PEG);
ii. 0% to about 75% of a secondary polar solvent;
iii. a modulating agent
iv. about 0.01% to about 5% by weight of at least one polymeric agent and mixtures of any two or more thereof, wherein the polymeric agent is selected from the group consisting of a locust bean gum, sodium alginate, sodium caseinate, an egg albumin, a gelatin agar, a carrageenin gum, a xanthan gum, a quince seed extract, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, a methylhydroxyethylcellulose, a hydroxyethyl carboxymethyl cellulose, a carboxymethyl cellulose, a cationic cellulose, a PEG 1000, a PEG 4000, a PEG 6000, a PEG 8000 and a carbomer;
v. a surface active agent;
vi. a foam adjuvant selected from the group consisting of a fatty alcohol having 15 or more carbons in its carbon chain, a fatty acid having 16 or more carbons in its carbon chain and mixtures of any two or more thereof; and
vii. a liquefied or compressed gas propellant at a concentration of about 3% to about 25% by weight of the foamable waterless composition wherein the gas propellant is essentially free of chlorofluorocarbons;
wherein the at least one active agent is chemically unstable in the carrier in the absence of a modulating agent;
wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent
wherein the carrier is shakable or flowable; and
wherein the composition is stored in an aerosol container and upon release expands to form a breakable foam that collapses upon application of shear force.

9. The foamable waterless composition of claim 8, wherein the breakable foam is of about good quality.

10. The foamable waterless composition of claim 8, wherein the modulating agent is selected from the group consisting of sodium citrate, citric acid, lactic acid, glutamic acid, ascorbic acid, azelaic acid, stearic acid, triethanolamine, lysine, lidocaine, prilocalne, carbomer, formic acid, acetic acid, propionic acid, butyric acid, butyric acid, caproic acid, caprylic acid, nonanoic acid, capric acid, lauric acid, myristic acid, valproic acid, and mixtures of any two or more thereof.

11. The foamable waterless composition of claim 8, wherein the polyol is selected from the group consisting of a diol; a triol; at least one diol and at least one triol, wherein the ratio between the diol and triol is between 9:1 and 1:1; a saccharide; and mixtures of any two or more thereof.

12. The foamable waterless composition of claim 11, wherein the diol is selected from the group consisting of propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol; and or
wherein the triol is selected from the group consisting of glycerin, butane-1,2,3-triol, butane-1,2,4-triol and hexane-1,2,6-triol.

13. The foamable waterless composition of claim 8, wherein the PEG is selected from the group consisting of a PEG 200, a PEG 300, a PEG 400, a PEG 600, a PEG 1000, a PEG 4000, a PEG 6000 and a PEG 8000.

14. The foamable waterless composition of claim 8, wherein the carrier comprises one or more PEGs in a concentration to provide viscosity of less than 12,000 CPs.

15. The foamable waterless composition of claim 8, wherein the carrier comprises a mixture of at least one polyol and at least one PEG.

16. The foamable waterless composition of claim 8, wherein the secondary polar solvent is selected from the group consisting of dimethyl isosorbide, tetrahydrofurfuryl alcohol polyethyleneglycol ether, DMSO, a pyrrolidone, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid.

17. The foamable waterless composition of claim 8, wherein the carrier comprises (1) at least one polar solvent selected from a diol, a triol and PEG, and (2) at least one secondary polar solvent.

18. The foamable waterless composition of claim 8, wherein the ratio between the polyol and/or PEG and the secondary polar solvent is between 9:1 and 1:4.

19. The foamable waterless composition of claim 8, wherein the composition is substantially alcohol-free.

20. The foamable waterless composition of claim 8, wherein the modulating agent is selected from the group consisting of an alpha hydroxy acid, an aliphatic beta hydroxy acid, an aromatic acid, an aromatic hydroxy acid, an alpha ketoacid, an aliphatic carboxylic acid, a branched aliphatic carboxylic acid, a short chain carboxylic acid, a fatty acid, an omega-3 fatty acid, an omega-6 fatty acid, an omega-9 fatty acid, a dicarboxylic acid, a branched dicarboxylic acid, an unsaturated dicarboxylic acid, an amino acid, a dimer or oligomer of amino acids, a retinoid, a nitrogen-containing organic compound, a primary, secondary, tertiary and quaternary amine, an amide, an amine oxide and a lactam.

21. The foamable waterless composition of claim 20,
wherein the alpha hydroxy acid and beta hydroxyl acid are selected from the group consisting of alpha-hydroxybutyric acid, alpha-hydroxyisobutyric acid, alpha-hydroxyisocaproic acid, alpha-hydroxyisovaleric acid, atrolactic acid, beta-hydroxybutyric acid, beta-phenyl lactic acid, beta-phenylpyruvic acid, citric acid, pyruvic acid, galacturonic acid, glucoheptonic acid, glucoheptono 1,4-lactone, gluconic acid, gluconolactone, glucuronic acid, glucuronolactone, glycolic acid, lactic acid, mandelic acid, mucic acid, pyruvic acid, saccharic acid, saccharic acid 1,4-lactone, tartaric acid and tartronic acid, 3-Hydroxybutanoic acid, quinic acid, isocitric acid, tropic acid, trethocanic acid, chlorolactic acid, citramalic acid, agaricic acid, aleuritic acid, pantoic acid, lactobionic acid, piscidic acid, hexylosonic acid or the anhydride thereof, and salicylic acids and derivatives thereof;
wherein the aromatic acid is selected from the group consisting of benzoic acid, toluic acid, dimethyl benzoic acid and phthalic acid;
wherein the alpha ketoacid has the molecular structure of (Ra)COCOO(Rb);

wherein Ra and Rb are independently selected from the group consisting of H and saturated or unsaturated, isomeric or non-isomeric, straight, branched, or cyclic C1-C25 alkyl, aralkyl, or aryl groups, wherein Ra may be optionally substituted with an F, Cl, Br, I, OH, CHO, COOH, or alkoxy group having 1 to 9 carbon atoms;

wherein the aliphatic carboxylic acid is selected from the group consisting of formic acid, acetic acid, propionic acid, butyric acid, butyric acid, caproic acid, caprylic acid, nonanoic acid, capric acid, lauric acid, myristic acid, palmitic acid, stearic acid, arachidic acid, behenic acid, octacosanoic acid, oleic acid, linoleic acid, alpha-linolenic acid, arachidonic acid, eicosapentaenoic acid, docosahexaenoic acid, erucic acid, valproic acid and 12-hydroxy stearic acid;

wherein the dicarboxylic acid is selected from the group consisting of oxalic acid, malonic acid, succinic acid, glutaric acid, adipic acid, pimelic acid, suberic acid, azelaic acid, sebacic acid, dodecanedioic acid, brassylic acid, thapsic acid, 14-methylnonacosanedioic acid, 14,15-dimethyltriacontanedioic acid (C30) undecylenic acid, maleic acid and fumaric acid; wherein the carbon atom skeleton of the branched dicarboxylic acid is substituted with at least one group selected from the group consisting of R, F, Cl, Br, OH, OR, SH, CHO, COOH, and NRaRb, and wherein R, Ra and Rb are independently selected from the group consisting of H, saturated or unsaturated, isomeric or non-isomeric, straight, branched, or cyclic C1-C25 alkyl, aralkyl, or aryl groups;

wherein the branched dicarboxylic acid is selected from the group consisting of aspartic acid, alpha-ketoglutaric acid, adipic acid 2-amino, aconitic acid, benzene dicarboxylic acid, citramalic acid, citric acid, cystathionine, glucuronic acid, glutamic acid, itaconic acid, malic acid, mucic acid, oxalacetic acid, diamino pimelic acid, saccharic acid, dimethyl succinic acid, tartaric acid and tartronic acid;

wherein the carboxylic acid is selected from the group consisting retinoic acid, isotretinoin, ascorbic acid, isoascorbic acid, ethanesulfonic acid, glycerophosphoric acid, acetohydroxamic acid, aconitic acid, alpha-ketocaproic acid, aminomalonic acid, hippuric acid, hydrochloric acid, methanesulfonic acid, oxalic acid, phosphoric acid, sorbic acid, iminodiacetic acid and carnitine; and wherein the amino acid is selected from the group consisting of glycine, alanine, valine, leucine, isoleucine, serine, threonine, cysteine, methionine, aspartic acid, asparagine, glutamic acid, glutamine, arginine, lysine, histidine, phenylalanine, tyrosine, tryptophan, praline, B-alanine (3-alanine), 4-aminobutyrate (GABA), 3-cyanoalanine (B-cyanoalanine), 2-aminobutyric acid, 2-methylene-4-aminobutyric acid, 3-methylene-4-aminobutyric acid, 2-aminoisobutyric acid, 5-aminolevulinic acid, 2-amino-4-methylhexanoic acid (homoisoleucine), 2-amino-4-methylhex-4-enoic acid, 2-amino-4-methylhex-5-ynoic acid, 2-amino-3-methylpentanoic acid, 2-aminoadipic acid, 4-ethylideneglutamic acid, 3-aminoglutaric acid, 2-aminopimelic acid, N4-ethylasparagine, N4-methylasparagine, erythro-4-methylglutamic acid, 4-methyleneglutamic acid, 4-methyleneglutamine, N5-methylglutamine, N5-ethylglutamine (theanine), N5-isopropylglutamine, 2-amino-4-(aminoxy)butyric acid (canaline), 2,4-diaminobutyrate, N4-acetyl-2,4-diaminobutyrate, N4-lactyl-2,4-diaminobutyrate, N4-oxalyl-2,4-diaminobutyrate, 2,3-diaminopropionic acid, N3-acetyl-2,3-diaminopropionic acid, N3-methyl-2,3-diaminopropionic acid, N3-oxalyl-2,3-diaminopropionic acid, N6-acetyllysine, N6-methyllysine, N6-trimethyllysine (laminine), ornithine (2,5-diaminopentanoic acid), saccharopine (N6-(2'-glutamyl)lysine, 2,6-diaminopimelic acid, N4-(2-hydroxyethyl)asparagine, erythro-3-hydroxyaspartic acid, 4-hydroxyarginine, 4-hydroxycitrulline, threo-4-hydroxyglutamic acid, 3,4-dihydroxyglutamic acid, 3-hydroxy-4-methylglutamic acid, 3-hydroxy-4-methyleneglutamic acid, 4-hydroxy-4-methylglutamic acid, 4-hydroxy-glutamine, N5-(2-hydroxyethyl)glutamine, 5-hydroxynorleucine, threo-4-hydroxyhomoarginine, homoserine, O-acetylhomoserine, O-oxalylhomoserine, O-phosphohomoserine, 4-hydroxyisoleucine, 5-hydroxymethylhomocysteine, threo-3-hydroxyleucine, 5-hydroxyleucine, 2-hydroxylysine, 4-hydroxylysine, 5-hydroxylysine, N6-acetyl-5-hydroxylysine, N6-trimethyl-5-hydroxylysine, 4-hydroxyornithine, mimosine, 4-hydroxynorvaline, 5-hydroxynorvaline, 2-amino-4,5-dihydroxypentanoic acid, 2-amino-4-hydroxypimelic acid, 4-hydroxyvaline, O-acetylserine, O-phosphoserine, pipecolic acid, (piperidine-2-carboxylic acid), 3-hydroxypipecolic acid, trans-4-hydroxypipecolic acid, trans-5-hydroxypipecolic acid, 5-hydroxy-6-methylpipecolic acid, 4,5-dihydroxypipecolic acid, trans-3-hydroxyproline, trans-4-hydroxyproline, trans-4-hydroxymethylproline, azetidine-2-carboxylic acid, N-(3-amino-3-carboxypropyl)azetidine-2-carboxylic acid, 4,5-dehydropipecolic acid (baikiain), 3-amino-3-carboxypyrrolidone (cucurbitine), 2-(cyclopent-2'-enyl)glycine, 5-hydroxytryptophan, albizziine (2-amino-3-ureidopropionic acid), arginosuccinic acid, canavinosuccinic acid, citrulline, homoarginine, homocitrulline, indospicine, O-ureidohomoserine, 6-hydroxykynurenine, 3-(4-aminophenyl)alanine, 3-(3-aminomethylphenyl)alanine, 3-(3-carboxyphenyl)alanine, 3-carboxytyrosine, 3-(3-hydroxymethylphenyl)alanine, 3-(3-hydroxyphenyl)alanine, 3-(3,4-dihydroxyphenyl)alanine (L-DOPA), 2-(phenyl)glycine, 2-(3-carboxyphenyl)glycine, 2-(3-carboxy-4-hydroxyphenyl)glycine, 2-(3-hydroxyphenyl)glycine, 2-(3,5-dihydroxyphenyl)glycine, 4-aminopipecolic acid, guvacine, 2-amino-4-(isoxazolin-5-one)-2-yl)butyric acid, lathyrine, tetrahydrolathyrine and ornithin and dimers or oligomers thereof.

22. The foamable waterless composition of claim 20, wherein the modulating agent is a nitrogen-containing organic compound selected from the group consisting of primary amines, methylamine and ethylamine; an ethanolamine, monoethanolamine, monoisopropanolamines, a diamine, ethylenediamine, 1,2-diaminopropane, a dialkylamine, dimethylamine, diethylamine, diethanolamine, diisopropanolamine, N-methylethanolamine, N-ethylethanolamine, a tertiary amine, a trialkylamine, triethylamine, triethylamine, triethanolamine, N-methyldiethanolamine and tri-isopropanolamine.

23. The foamable waterless composition of claim 8, wherein the polymeric agent is a cellulose polymer or a carbomer.

24. The foamable waterless composition of claim 8, wherein the polymeric agent is dispersible in the polyol or in the mixture of a polyol and an additional polar solvent.

25. The foamable waterless composition of claim 8, wherein the surface active agent comprises at least one surfactant selected from the group consisting of a polyoxyethylene fatty ether, a polyoxyethylene fatty ester, a carbohydrate ester and a sucrose ester, glyceryl stearate, PEG-100 stearate, steareth-2, steareth-20, steareth-21, ceteareth 2, PEG-100 stearyl ether, cetearyl glucoside, methyl glucose sesquistearate, sorbitan monostearate, GMS NE, span 20, glyceryl stearate and PEG 100 stearate, glyceryl stearate and PEG 100 stearate and laureth4; steareth 2, PEG 100 searate and laureth4, and cetearyl glucoside and cetearyl alcohol.

26. The foamable waterless composition of claim 8, wherein the surface active agent comprises a non-ionic surface active agent.

27. The foamable waterless composition of claim 26, wherein the surface active agent further comprises an ionic surfactant, selected from the group consisting of a cationic surfactant, a zwitterionic surfactant, an amphoteric surfactant and an ampholytic surfactant.

28. The foamable waterless composition of claim 26, wherein the surface active agent comprises a mixture of at least one non-ionic surfactant and at least one ionic surfactant in a ratio selected from
 a. about 100:1 to about 6:1
 b. about 1:1 to about 20:1.

29. The foamable waterless composition of claim 8, further comprising a hydrophobic solvent.

30. The foamable waterless composition of claim 29, wherein the hydrophobic solvent is selected from the group consisting of a mineral oil, isopropyl palmitate, isopropyl isostearate, diisopropyl adipate, diisopropyl dimerate, a maleated soybean oil, octyl palmitate, cetyl lactate, cetyl ricinoleate, tocopheryl acetate, an acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, an olive oil, a corn oil, a soybean oil, a canola oil, a cottonseed oil, a coconut oil, a sesame oil, a sunflower oil, a borage seed oil, a *Syzygium aromaticum* oil, a hempseed oil, a herring oil, a cod-liver oil, a salmon oil, a flaxseed oil, a wheat germ oil, an evening primrose oil, an essential oil, a silicone oil, a dimethicone, a cyclomethicone, a polyalkyl siloxane, a polyaryl siloxane, a polyalkylaryl siloxane, a polyether siloxane copolymer, and a poly(dimethylsiloxane)-(diphenyl-siloxane) copolymer.

31. The foamable waterless composition of claim 8, wherein the foam adjuvant is selected from the group consisting of cetyl alcohol, stearyl alcohol, behenyl alcohol, stearic acid and any two or more thereof.

32. The foamable waterless composition of claim 8, further comprising an additional component selected from the group consisting of an anti perspirant, an anti-static agent, a buffering agent, a bulking agent, a chelating agent, a colorant, a conditioner, a deodorant, a diluent, a dye, an emollient, a fragrance, a humectant, an occlusive agent, a penetration enhancer, a perfuming agent, a permeation enhancer, a preservative, a skin penetration enhancer, a sunscreen, a sun blocking agent, a sunless tanning agent, and a vitamin.

33. The foamable waterless composition of claim 8, wherein the one or more active agents are selected from the group consisting of active herbal extracts, acaricides, age spot and keratose removing agents, allergen, analgesics, local anesthetics, antiacne agents, antiallergic agents, antiaging agents, antiinfective, antibacterials, antibiotics, antiburn agents, anticancer agents, antidandruff agents, antidepressants, antidermatitis agents, antiedemics, antifungal, antihistamines, antihelminths, antihyperkeratolyte agents, antiinflammatory agents, antiirritants, antilipemics, antimicrobials, antimycotics, antiproliferative agents, antiparasitic agents, antioxidants, anti-wrinkle agents, antipruritics, antipsoriatic agents, antirosacea agents antiseborrheic agents, antiseptic, antiswelling agents, antiviral agents, anti-yeast agents, agents that control yeast, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, nonsteroidal anti-inflammatory agents, oxidizing agents, pediculicides, photodynamic therapy agents, retinoids, sanatives, scabicides, self tanning agents, steroids, skin whitening agents, asoconstrictors, vasodilators, vitamins, vitamin D derivatives, flavonoids, wound healing agents and wart removers.

34. The foamable waterless composition of claim 33, wherein the steroid is selected from the group consisting of alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chloroprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, difluorosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters and salts thereof;
 wherein the antifungal is selected from the group consisting of a polyene, natamycin, nystatin; an allylamine, naftifine, terbinafine; an imidazole, bifonazole, clotrimazole, econazole, fenticonazole, ketocanazole, miconazole, oxiconazole; a diazole, a triazoles, fluconazole, itraconazole, terconazole, tolnaftate, ciclopirox, undecylenic acid, sulbentine, griseofulvin, Amphotericin B, flucytosine (5FC), a morpholine compound, amorolfine, and the related morpholines and analogs, derivatives and salts thereof, and any combination thereof at a therapeutically effective concentration; and
 wherein the antibacterial is selected from the group consisting of a beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bis-biguanide, a polymeric biguanide, a naturally occurring antibiotic compound and analogs, derivatives, salts, ions and complexes thereof.

35. The foamable waterless composition of claim 8, wherein the one or more active agents are unstable in the presence of water.

36. The foamable waterless composition of claim 8, wherein the one or more active agents are stable at an acidic pH range and the modulating agent is acidic.

37. The foamable waterless composition of claim 8, wherein the active agent is an ester, which undergoes hydrolysis at basic pH.

38. The foamable waterless composition of claim 8, wherein the one or more active agents undergo rearrangement at basic pH.

39. The foamable waterless composition of claim 8, wherein the one or more active agents are stable at a basic pH range and the modulating agent is basic.

40. The foamable waterless composition of claim 39, wherein the active agent is selected from vitamin D, a vitamin D analog, a vitamin D derivative.

41. The foamable waterless composition of claim 8, wherein the modulating agent is a nitrogen-containing modulating agent.

42. The foamable waterless composition of claim 8, wherein the modulating agent is triethanolamine and the active agent is calcipotriol.

43. The foamable waterless composition of claim 8, wherein the modulating agent is selected from the group consisting of sodium citrate, citric acid, lactic acid, glutamic acid, azaleic acid, ascorbic acid, stearic acid, formic acid, acetic acid, propionic acid, butyric acid, butyric acid, caproic acid, caprylic acid, nonanoic acid, capric acid, lauric acid, myristic acid, valproic acid, and mixtures of any two or more thereof and the active agent is betamethasone valerate.

44. The foamable waterless composition of claim 8, wherein the modulating agent is selected from the group consisting of carbomer, and triethanolamine, and mixtures thereof and the active agent is selected from the group consisting of clobetosol proprionate and flucinoline acetonide.

45. The foamable waterless composition of claim 8, wherein the one or more active agents are stable at about neutral pH range and the modulating agent is neutral.

46. The foamable waterless composition of claim 8, wherein the modulating agent is a pharmaceutical or cosmetic active agent.

47. The foamable waterless composition of claim 8, comprising (1) a corticosteroid; and (2) and active agent selected from the group of an antifungal agent, an antimicrobial agent, an antiviral agent, an anti-acne agent, a vitamin D3 derivative, calcipotriol, and antipsoriasis agent, a keratolytic agent and an antiacne agent.

48. The foamable waterless composition of claim 8, comprising (1) a keratolytic agent; and (2) an active agent selected from the group of a corticosteroid, an antifungal agent, an antimicrobial agent, an antiviral agent, an anti-acne agent, a vitamin D3 derivative, calcipotriol, an antipsoriasis agent, an immunomodulator, an immunosuppressant and an antiacne agent.

49. A method of treating a disorder of mammalian subject, comprising:
administering a composition to a target site, the composition comprising:
one or more active agents and a waterless carrier for topical delivery of the one or more active agents, wherein the waterless carrier is suitable for stabilizing at least one of said one or more active agents, said waterless carrier comprising:
a) about 25% to about 98% of at least polar solvent selected from the group consisting of (1) a polyol; and (2) a polyethylene glycol (PEG) solvent;
b) a modulating agent;
c) about 0.01% to about 5% by weight of at least one polymeric agent;
d) a surface active agent; and
e) a foam adjuvant selected from the group consisting of a fatty alcohol having 15 or more carbons in its carbon chain, a fatty acid having 16 or more carbons in its carbon chain and mixtures of any two or more thereof;
wherein the at least one active agent is chemically unstable in the carrier in the absence of a modulating agent;
wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent; and
wherein if the composition is packaged in an aerosol container and a liquefied or compressed gas propellant is added at a concentration of about 3% to about 25% by weight of the composition, then the composition will be capable upon release from the aerosol container to expand to form a breakable foam that collapses upon application of shear force.

50. A method of treating a disorder of mammalian subject, comprising:
administering a foamable composition to a target site, the composition comprising:
a foamable waterless composition comprising:
a. a therapeutically effective concentration of one or more active agents;
b. a carrier for topical delivery of the one or more active agents suitable for stabilizing at least one of said one or more active agents, comprising
i. about 25% to about 98% of at least polar solvent selected from the group consisting of (1) a polyol; and (2) a polyethylene glycol (PEG);
ii. 0% to about 75% of a secondary polar solvent;
iii. a modulating agent;
iv. about 0.01% to about 5% by weight of at least one polymeric agent;
v. a surface active agent;
vi. a foam adjuvant selected from the group consisting of a fatty alcohol having 15 or more carbons in its carbon chain, a fatty acid having 16 or more carbons in its carbon chain and mixtures of any two or more thereof; and
vii. a liquefied or compressed gas propellant at a concentration of about 3% to about 25% by weight of the foamable waterless composition wherein the gas propellant is essentially free of chlorofluorocarbons;
wherein the at least one active agent is chemically unstable in the carrier in the absence of a modulating agent;
wherein the modulating agent is capable of and is selected to modulate or adjust the artificial pH of the carrier to an artificial pH or to provide an artificial pH buffering effect such that the chemical stability of the at least one active agent is increased as compared to its stability in the carrier without the modulating agent;

wherein the carrier is shakable or flowable; and
wherein the foamable waterless composition is stored in an aerosol container and upon release expands to form a breakable foam that collapses upon application of shear force; and
wherein the polymeric agent is selected from the group consisting of a locust bean gum, sodium alginate, sodium caseinate, an egg albumin, a gelatin agar, a carrageenin gum, a xanthan gum, a quince seed extract, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, a methylhydroxyethylcellulose, a hydroxyethyl carboxymethyl cellulose, a carboxymethyl cellulose, a cationic cellulose, a PEG 1000, a PEG 4000, a PEG 6000, a PEG 8000 and a carbomer.

51. The method of claim 50, wherein the target site is selected from the group consisting of the skin, a body cavity, a mucosal surface, the nose, the mouth, the eye, the ear canal, the respiratory system, the vagina and the rectum.

52. The method of claim 50, wherein the disorder is selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, postoperative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, calluses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; and wherein the active agent is suitable for treating said disorder.

53. The foamable waterless composition of claim 8, comprising a solid, semi solid or waxy surfactant wherein the amount of surfactant or combination of surfactants is between about 0.05% to about 10%.

54. The foamable waterless composition of claim 8, comprising a solid, semi solid or waxy surfactant which is soluble in oil and having a HLB or weighted average HLB of less than about 12.

55. A foamable waterless composition comprising:
  a. a therapeutically effective concentration of one or more active agents;
  b. a carrier for topical delivery of the one or more active agents suitable for stabilizing at least one of said one or more active agents, comprising:
    i. about 25% to about 98% of at least polar solvent selected from the group consisting of (1) a polyol; and (2) a polyethylene glycol;
    ii. 0% to about 75% of a secondary polar solvent;
    iii. a modulating agent;
    iv. about 0.01% to about 5% by weight of at least one polymeric agent;
    v. a surface active agent;
    vi. a foam adjuvant selected from the group consisting of a fatty alcohol having 15 or more carbons in its carbon chain, a fatty acid having 16 or more carbons in its carbon chain and mixtures of any two or more thereof; and
    vii. a liquefied or compressed gas propellant at a concentration of about 3% to about 25% by weight of the foamable waterless composition, wherein the gas propellant is essentially free of chlorofluorocarbons;
  wherein the at least one active agent is chemically unstable in the carrier in the absence of a modulating agent;
  wherein the modulating agent comprises one or more agents that are capable of impeding said destabilization and or are capable of stabilizing the active agent by chelating a metal ion such that the modulating agent is capable of reducing in the carrier the availability of metal ions so the stability of at least one active agent is improved when compared to its stability in the carrier without the modulating agent;
  wherein the carrier is shakable or flowable; and
  wherein the composition is stored in an aerosol container and upon release expands to form a breakable foam that collapses upon application of shear force; and
  wherein the polymeric agent is selected from the group consisting of a locust bean gum, sodium alginate, sodium caseinate, an egg albumin, a gelatin agar, a carrageenin gum, a xanthan gum, a quince seed extract, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, a methylhydroxyethylcellulose, a hydroxyethyl carboxymethyl cellulose, a carboxymethyl cellulose, a cationic cellulose, a PEG 1000, a PEG 4000, a PEG 6000, a PEG 8000 and a carbomer.

56. The foamable waterless composition of claim 55 further comprising one or more agents that additionally are capable of impeding said destabilization and or are capable of stabilizing the active agent primarily by modulating or adjusting the artificial pH of the carrier such that the modulating agent is capable of producing in the carrier an artificial pH or an artificial pH buffering effect at about a pH or pH range in which the stability of at least one active agent is improved when compared to its stability in the carrier without the modulating agent and or by impeding ionization and or by impeding oxidation.

57. The foamable waterless composition of claim 55, wherein the modulating agent is a chelating agent.

58. The foamable waterless composition of claim 57, wherein the chelating agent is sufficiently soluble or functional in the polar solvent to enable it to "mop up" or "lock" metal ions.

59. The foamable waterless composition of claim 57, wherein the chelating agent is selected from the group consisting of ethylenediaminetetraacetic acid ("EDTA") and salts thereof, disodium EDTA, tetrasodium EDTA, calcium disodium EDTA; diethylenetriaminepentaacetic acid ("DTPA") and salts thereof; hydroxyethlethylenediaminetriacetic acid ("HEDTA") and salts thereof; and nitrilotriacetic acid ("NTA") and salts thereof; acetyl trihexyl citrate, aminotrimethylene phosphonic acid, beta-alanine diacetic acid, bismuth citrate, calcium disodium edta, citric acid, cyclohexanediamine tetraacetic acid, diammonium citrate, dibutyl oxalate, diethyl oxalate, diisobutyl oxalate, diisopropyl oxalate, dilithium oxalate, dimethyl oxalate, dipotassium edta, dipotassium oxalate, dipropyl oxalate, disodium edta, disodium edta-copper, disodium pyrophosphate, edta, etidronic acid, hedta, methyl cyclodextrin, oxalic acid, pentapotassium, triphosphate, pentasodium aminotrimethylene phosphonate, pentasodium pentetate, pentasodium triphosphate, pentetic acid, phytic acid, potassium citrate, sodium citrate, sodium dihydroxyethylglycinate, sodium gluceptate, sodium gluconate, sodium hexametaphosphate, sodium metaphosphate, sodium metasilicate, sodium oxalate, sodium trimetaphosphate, tea-edta, tetrahydroxypropyl ethylenediamine, tetrapotassium etidronate, tetrapotassium pyrophosphate, tetrasodium edta, tetrasodium etidronate, tetrasodium pyrophosphate, tripotassium edta, trisodium edta, trisodium hedta, trisodium nta, trisodium phosphate, malic acid, fumaric acid, maltol, succimer, penicillamine, dimercaprol, and desferrioxamine mesilate.

60. A foamable waterless carrier for use with a therapeutically effective concentration of one or more active agents comprising:
    i. about 25% to about 98% of at least polar solvent selected from the group consisting of (1) a polyol; and (2) a polyethylene glycol; 0% to about 75% of a secondary polar solvent;
    ii. a modulating agent;
    iii. about 0.01% to about 5% by weight of at least one polymeric agent;
    iv. a surface active agent;
    v. a foam adjuvant selected from the group consisting of a fatty alcohol having 15 or more carbons in its carbon chain, a fatty acid having 16 or more carbons in its carbon chain and mixtures of any two or more thereof; and
    vi. a liquefied or compressed gas propellant at a concentration of about 3% to about 25% by weight of the foamable waterless carrier, wherein the gas propellant is essentially free of chlorofluorocarbons wherein at least one active agent if present is susceptible, to one or more of reaction, breakdown, ionization or oxidation;

wherein the modulating agent comprises one or more agents that are capable of impeding said destabilization and or are capable of stabilizing the active agent primarily by modulating or adjusting the artificial pH of the carrier such that the modulating agent is capable of producing in the waterless carrier an artificial pH or an artificial pH buffering effect at about a pH or pH range in which the stability of at least one active agent is improved when compared to its stability in the carrier without the modulating agent and or by chelating a metal ion such that the modulating agent is capable of reducing in the waterless carrier the availability of metal ions so the stability of at least one active agent is improved when compared to its stability in the carrier without the modulating agent;

wherein the foamable waterless carrier is shakable or flowable; and wherein the foamable waterless carrier is stored in an aerosol container and upon release expands to form a breakable foam that collapses upon application of shear force; and wherein the polymeric agent is selected from the group consisting of a locust bean gum, sodium alginate, sodium caseinate, an egg albumin, a gelatin agar, a carrageenin gum, a xanthan gum, a quince seed extract, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, a methylhydroxyethylcellulose, a hydroxyethyl carboxymethyl cellulose, a carboxymethyl cellulose, a cationic cellulose, a PEG 1000, a PEG 4000, a PEG 6000, a PEG 8000 and a carbomer.

61. The waterless composition of claim 4, wherein the concentration of the polymeric agent is selected such that the viscosity of the composition is less than 12,000 CPs, or less than 10,000 CPs.

62. The waterless composition of claim 1, wherein the modulating agent is an acid.

63. The waterless composition of claim 62, wherein the acid is a fatty acid selected from the group consisting of stearic acid, lauric acid, myristic acid, valproic acid, and mixtures of any two or more thereof.

\* \* \* \* \*

UNITED STATES PATENT AND TRADEMARK OFFICE
CERTIFICATE OF CORRECTION

| | | |
|---|---|---|
| PATENT NO. | : 8,795,693 B2 | Page 1 of 1 |
| APPLICATION NO. | : 11/947751 | |
| DATED | : August 5, 2014 | |
| INVENTOR(S) | : Tamarkin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1224 days.

Signed and Sealed this
Eleventh Day of August, 2015

Michelle K. Lee
*Director of the United States Patent and Trademark Office*